US008165896B2

(12) United States Patent
Jung et al.

(10) Patent No.: US 8,165,896 B2
(45) Date of Patent: *Apr. 24, 2012

(54) COMPLIANCE DATA FOR HEALTH-RELATED PROCEDURES

(75) Inventors: Edward K. Y. Jung, Bellevue, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 767 days.

This patent is subject to a terminal disclaimer.

(21) Appl. No.: 12/080,264

(22) Filed: Mar. 31, 2008

(65) Prior Publication Data

US 2008/0281636 A1 Nov. 13, 2008

Related U.S. Application Data

(63) Continuation-in-part of application No. 11/489,244, filed on Jul. 18, 2006, and a continuation-in-part of application No. 11/478,569, filed on Jun. 29, 2006, and a continuation-in-part of application No. 12/074,243, filed on Feb. 29, 2008.

(51) Int. Cl.
*G06F 19/00* (2011.01)
*G06Q 10/00* (2012.01)

(52) U.S. Cl. ............................................. 705/2; 705/3

(58) Field of Classification Search .................. 705/2, 3, 705/4

See application file for complete search history.

(56) References Cited

U.S. PATENT DOCUMENTS

| | | | |
|---|---|---|---|
| 3,970,996 A | 7/1976 | Yasaka et al. | |
| 4,156,620 A | 5/1979 | Clemens | |
| 4,164,320 A | 8/1979 | Irazoqui et al. | |
| 4,695,954 A | 9/1987 | Rose et al. | |
| 4,781,704 A | 11/1988 | Potter | |
| 4,843,377 A | 6/1989 | Fuller et al. | |
| 4,857,713 A | 8/1989 | Brown et al. | |
| 4,857,716 A | 8/1989 | Gombrich et al. | |
| 4,930,997 A | 6/1990 | Bennett | |
| 4,999,613 A | 3/1991 | Williamson et al. | |
| 5,026,084 A | 6/1991 | Pasfield | |
| 5,092,850 A | 3/1992 | Buma | |
| 5,947,937 A | 9/1999 | Urrutia et al. | |
| 6,024,699 A * | 2/2000 | Surwit et al. | 600/300 |
| 6,294,999 B1 | 9/2001 | Yarin et al. | |

(Continued)

OTHER PUBLICATIONS

U.S. Appl. No. 11/588,116, Jung et al.

(Continued)

*Primary Examiner* — Robert Morgan
*Assistant Examiner* — Sean K Hunter

(57) ABSTRACT

Exemplary embodiments provide a verification technique that facilitates administration of a health-related procedure to an intended recipient patient or group of patients. An interface template or signal protocol may be configured to establish suitable matching between the patient and various types of objects used to administer the health-related procedure. In some embodiments real-time monitoring data regarding administration of a health-related procedure to a recipient patient is posted to a patient data record that has restricted read/write access. In some instances the monitoring data is processed to determine compliance or non-compliance based on comparison of the health-related procedure with a predetermined benchmark standard.

35 Claims, 42 Drawing Sheets

U.S. PATENT DOCUMENTS

| | | | |
|---|---|---|---|
| 6,380,858 | B1 | 4/2002 | Yarin et al. |
| 6,454,705 | B1 | 9/2002 | Cosentino et al. |
| 6,523,009 | B1 | 2/2003 | Wilkins |
| 6,575,969 | B1 | 6/2003 | Ritmann, III et al. |
| 6,671,563 | B1 | 12/2003 | Engelson et al. |
| 6,699,193 | B2 | 3/2004 | Crutchfield et al. |
| 6,790,198 | B1 | 9/2004 | White et al. |
| 6,824,052 | B2 | 11/2004 | Walsh |
| 6,980,111 | B2 | 12/2005 | Nolte |
| 7,029,034 | B2 | 4/2006 | Newell |
| 7,039,628 | B2 | 5/2006 | Logan, Jr. |
| 7,321,862 | B2 | 1/2008 | Rosenfeld et al. |
| 7,411,509 | B2 | 8/2008 | Rosenfeld et al. |
| 7,853,455 | B2 | 12/2010 | Brown |
| 2001/0054155 | A1 | 12/2001 | Hagan et al. |
| 2002/0016719 | A1 | 2/2002 | Nemeth et al. |
| 2002/0022972 | A1 | 2/2002 | Costello |
| 2002/0032583 | A1* | 3/2002 | Joao .................................. 705/2 |
| 2002/0052763 | A1 | 5/2002 | Jung Richardson |
| 2002/0055858 | A1 | 5/2002 | Jackson |
| 2002/0065686 | A1 | 5/2002 | Monteleone et al. |
| 2002/0067270 | A1 | 6/2002 | Yarin et al. |
| 2002/0188259 | A1 | 12/2002 | Hickle et al. |
| 2003/0022141 | A1 | 1/2003 | Packard |
| 2003/0036683 | A1 | 2/2003 | Kehr et al. |
| 2003/0040700 | A1 | 2/2003 | Hickle et al. |
| 2003/0140928 | A1 | 7/2003 | Bui et al. |
| 2003/0208382 | A1 | 11/2003 | Westfall |
| 2003/0212579 | A1 | 11/2003 | Brown et al. |
| 2004/0010425 | A1 | 1/2004 | Wilkes et al. |
| 2004/0026501 | A1 | 2/2004 | Walsh |
| 2004/0045031 | A1 | 3/2004 | Gautier |
| 2004/0203692 | A1 | 10/2004 | Schwinke et al. |
| 2004/0254816 | A1 | 12/2004 | Myers |
| 2005/0060188 | A1 | 3/2005 | Valley |
| 2005/0119534 | A1 | 6/2005 | Trost et al. |
| 2005/0139651 | A1 | 6/2005 | Lim et al. |
| 2005/0165627 | A1 | 7/2005 | Fotsch et al. |
| 2005/0187789 | A1 | 8/2005 | Hatlestad et al. |
| 2005/0218152 | A1 | 10/2005 | Simon |
| 2005/0240304 | A1 | 10/2005 | York et al. |
| 2005/0251102 | A1 | 11/2005 | Hegland et al. |
| 2005/0258244 | A1 | 11/2005 | Mitchell et al. |
| 2006/0028727 | A1 | 2/2006 | Moon et al. |
| 2006/0058917 | A1 | 3/2006 | Vonk et al. |
| 2006/0061472 | A1 | 3/2006 | Lovoi et al. |
| 2006/0064087 | A1 | 3/2006 | Mirza et al. |
| 2006/0097516 | A1 | 5/2006 | Kozlowski et al. |
| 2006/0229918 | A1 | 10/2006 | Fotsch et al. |
| 2006/0265245 | A1 | 11/2006 | McCallie et al. |
| 2007/0016443 | A1 | 1/2007 | Wachman et al. |
| 2007/0018121 | A1 | 1/2007 | Leyman et al. |
| 2007/0043590 | A1 | 2/2007 | Lee |
| 2007/0061167 | A1 | 3/2007 | Brown |
| 2007/0233854 | A1 | 10/2007 | Bukovec et al. |
| 2007/0274574 | A1 | 11/2007 | Boult et al. |

OTHER PUBLICATIONS

U.S. Appl. No. 11/584,812, Jung et al.
U.S. Appl. No. 11/580,692, Jung et al.
U.S. Appl. No. 11/580,525, Jung et al.
U.S. Appl. No. 11/149,464, Jung et al.
"Acquiring, Organizing, and Displaying Medical Information"; *Insight*: A Tool for Viewing Data, Finding Answers, and Seeing Patterns; bearing a date of 2006; pp. 1-7.
Aller, MD, Raymond; "Positive patient identification: more than a double check"; System Review Series; bearing a date of Oct. 2005; pp. 26-34.
Avery, Catherine; "Quantum Leap in Medical Infomatics"; Washington Hospital Center Physician; vol. 10—No. 10; bearing a date of Dec. 2004-Jan. 2005; pp. 1, 10-11.
Beyea, Suzanne C.; "Patient identification—a crucial aspect of patient safety—Patient Safety First"; AORN Journal; bearing a date of Sep. 2003; pp. 1-3.
Beyea, Suzanne C.; "Systems that reduce the potential for patient identification errors"; AORN Journal; bearing a date of Sep. 2002; pp. 1-4.
"Convergence CT Introduces Inpatient Insight Hospital Patient-Level Data for Pharmaceutical Market Research and Clinical Trial Planning;" San Francisco—(Business Wire)—Nov. 13 2003; pp. 1; located at http://findarticles.com/p/articles/mi_m0EIN/is_2003_Nov_13/ai_n27.
"Former head of UHP's DUI unit ends appeal of alcohol-related conviction"; The Salt Lake Tribune; bearing a date of Mar. 3, 2008; pp. 1-2; located at http://www.sltrib.com/fdcp?1204574945509.
Greene, Jay; "Cover Story Essential news and information for physician business executives"; vol. 10/No. 10; bearing a date of Oct. 2006; pp. 1-7.
Holstein, William J.; "Patient Safety Through Technology"; Published Feb. 17, 2007, The New York Times; pp. 1-2.
McCarthy, Caroline; "Microsoft coughs up for health care software"; c/netnews.com; bearing a date of Jul. 27, 2006; pp. 1-2; located at http://news.com.com/2102-1014_3-6098696.html?tag=st.util.print.
Microsoft Executive Circle Case Study Detail; "Washington Hospital Center"; bearing a date of Jan. 20, 2004; pp. 1-5; located at http://www.microsoft.com/business/executivecircle/content/casestud. . . .
"PAR3 and Vitality, Inc. Join Forces to Improve Medication Adherence With Combined Solutions"; PAR3 Communications, Inc.; bearing a date of Aug. 28, 2007; pp. 1-2; located at http://www.prnewswire.ca/cgi-bin/stories.pl?ACCT=104&STORY. . . .
"Precision Dynamics' Bar Code System Solutions for Positive Patient Identification Featured at MUSE Conference"; Precision Dynamics Corporation; bearing a date of May 4, 2006; pp. 1-2.
Symbol Technologies, Inc.; "Safer Patient Care: Automated Medication Verification Solutions for Hospitals and Clinics"; bearing a date of 2003; pp. 1-3.
The Whittington Hospital NHS Trust; "Information for Staff to Accompany Patient Identification Policy"; bearing a date of Mar. 2003; pp. 1-14.
Versweyveld, Leslie; "Misys Insight clinical decision support tool integrates data from heterogeneous, enterprise-wide health care systems"; Virtual Medical Worlds Monthly; bearing a date of Jul. 23, 2002; pp. 1-3; located at http://www.hoise.com/vmw/02/articles/vmw/LV-VM-08-02-15.html.
White, Charlie; "Glowcap Ambient Pill Cap"; Bearing a date of May 29, 2007; pp. 1.

\* cited by examiner

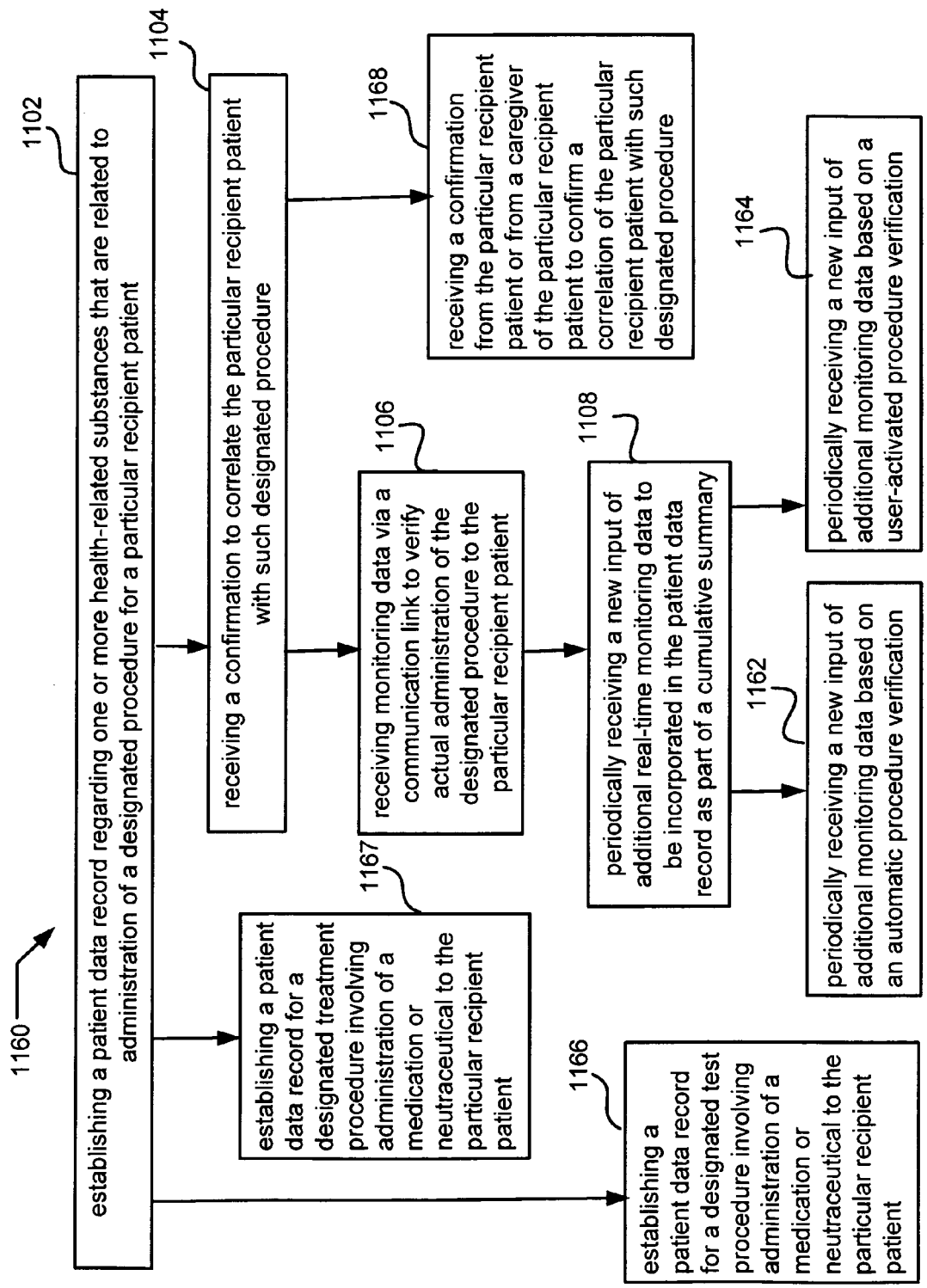

COMPLIANCE DATA FOR HEALTH-RELATED PROCEDURES

RELATED APPLICATIONS

For purposes of the USPTO extra-statutory requirements, the present application constitutes a continuation in part of U.S. patent application entitled ENHANCED COMMUNICATION LINK FOR PATIENT DIAGNOSIS AND TREATMENT, naming Edward K. Y. Jung, Royce A. Levien, Robert W. Lord, Mark A. Malamud, John D. Rinaldo, Jr. and Lowell L. Wood, Jr. as inventors, filed 18 Jul. 2006, Ser. No. 11/489,244, which is currently co-pending, or is an application of which a currently co-pending application listed as a Related Application is entitled to the benefit of the filing date.

For purposes of the USPTO extra-statutory requirements, the present application constitutes a continuation in part of United States patent application entitled VERIFICATION TECHNIQUE FOR PATIENT DIAGNOSIS AND TREATMENT, naming Edward K. Y. Jung, Royce A. Levien, Robert W. Lord, Mark A. Malamud, John D. Rinaldo, Jr. and Lowell L. Wood, Jr. as inventors, filed 29 Jun. 2006, Ser. No. 11/478,569, which is currently co-pending, or is an application of which a currently co-pending application listed as a Related Application is entitled to the benefit of the filing date.

For purposes of the USPTO extra-statutory requirements, the present application constitutes a continuation in part of United States patent application entitled DATA MAINTENANCE VIA PATIENT MONITORING TECHNIQUE, naming Edward K. Y. Jung, Royce A. Levien, Robert W. Lord, Mark A. Malamud, John D. Rinaldo, Jr. and Lowell L. Wood, Jr. as inventors, filed 29 Feb. 2008, Ser. No. 12/074,243, which is currently co-pending, or is an application of which a currently co-pending application listed as a Related Application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Systems and methods for providing diagnosis, treatment, testing, therapy, and other health-related procedures need additional safeguards to help assure proper maintenance and accessibility of an updated patient data record for a designated patient.

SUMMARY

Various embodiments and implementations are disclosed herein with respect to improved systems and methods for maintaining an updated patient data system for health-related procedures scheduled or completed for one or more patients.

Some patient data system embodiments may include a patient data record associated with a designated patient, a data input link coupled to the patient data record and configured to receive updated information based on real-time monitoring data regarding administration of a selected health-related procedure to the designated patient, and computerized apparatus configured to process a patient identifier for correlation with the selected health-related procedure. An additional possible system feature may include a comparison module operably coupled to the patient data record and the computer apparatus, wherein the comparison module is configured to determine compliance of the real-time monitoring data with a predetermined benchmark standard.

An exemplary process embodiment for maintaining updated patient compliance data may include establishing a patient data record regarding one or more health-related substances that are related to administration of a designated procedure for a particular recipient patient, receiving a confirmation to correlate the particular recipient patient with such designated procedure, and receiving monitoring data via a communication link to verify actual administration of the designated procedure to the particular recipient patient. An additional process feature may include periodically receiving a new input of additional real-time monitoring data to be incorporated in the patient data record as part of a cumulative summary.

Various process components may be incorporated in computer-readable media bearing instructions for executing and implementing the process steps. For example, such instructions may implement a process for maintaining an updated patient data record, wherein the process includes identifying a recipient patient scheduled for administration of a selected health-related procedure, maintaining a patient data record for such administration of the selected health-related procedure to the recipient patient, and processing and storing real-time monitoring data that includes confirmation of a patient identifier for the recipient patient as well as real-time verification of administration of the selected health-related procedure. An additional process feature may include making a comparison regarding a health-related procedure administered to a recipient patient to determine compliance with a predetermined benchmark standard.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 37-42 are flow charts illustrating other possible aspects of exemplary process embodiments.

DETAILED DESCRIPTION

Figure 1:
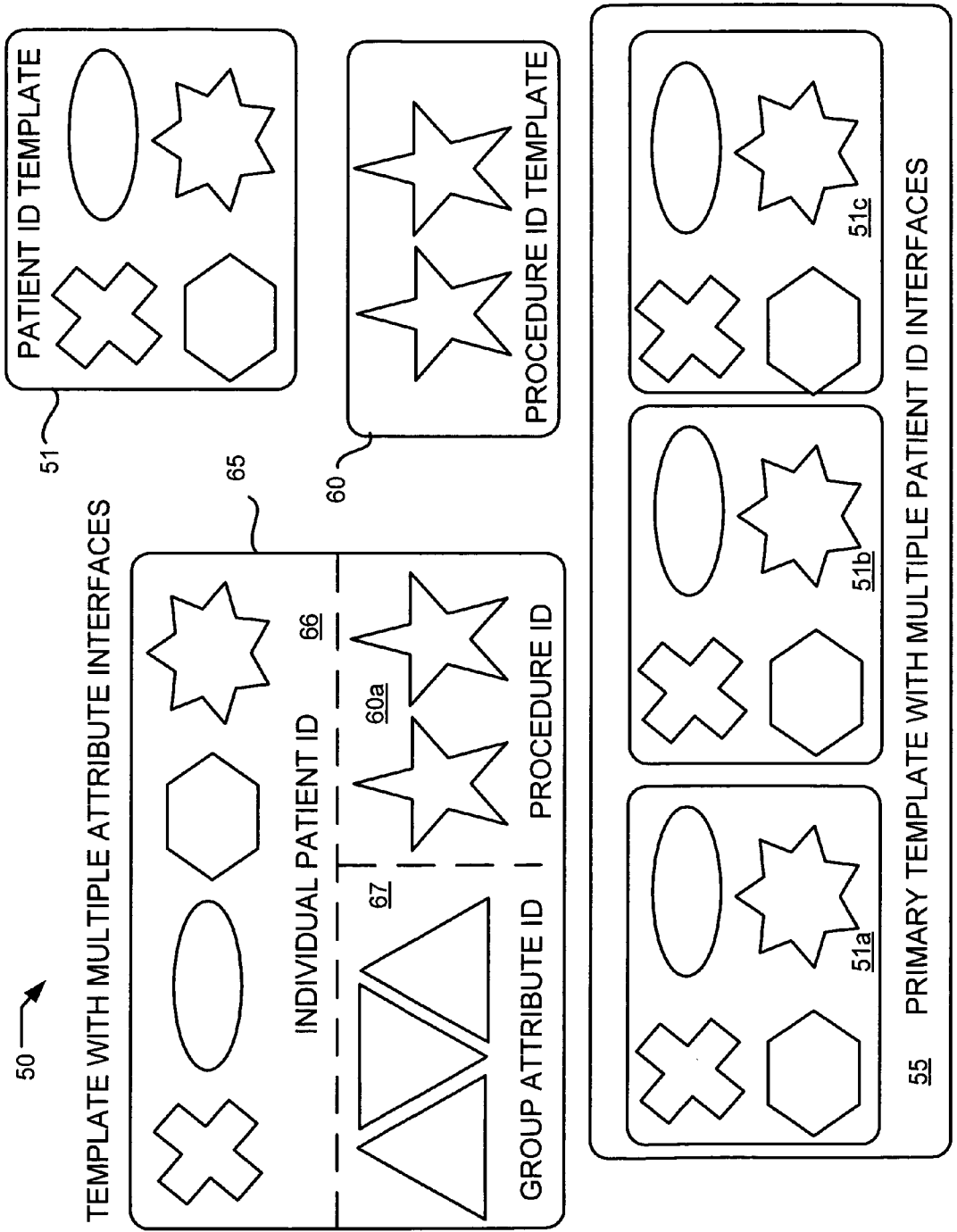
FIG. 1 is a schematic representation of exemplary patient verification features that may be incorporated in an interface template.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The patient identification techniques disclosed herein may be adapted for the administration of many types of health-related procedures. Accordingly it is not possible to recite a complete listing of such health-related procedures that may incorporate the various interface template aspects illustrated in the exemplary disclosed embodiments.

It will be further understood that patient identification issues involving administration of health-related procedures affect many types of persons and entities including but not limited to manufacturers, distributors, wholesalers, retailers, hospitals, hospices, convalescent homes, emergency care facilities, pharmacies, health insurance providers, HMOs, clinics, home nursing services, and the like. It is believed that the various aspects and implementations for the patient verification techniques disclosed herein can be adapted for the benefit of such persons and entities as well as for the benefit of their clients and patients.

The exemplary patient verification features 50 shown in FIG. 1 include a patient ID template 51, a primary template 55 with multiple patient ID interfaces, and another template 65 with multiple attribute interfaces. It will be understood that an exemplary template associated with a particular patient may be configured as an interface for verifiable matching engagement with secondary template associated with a health-related procedure.

The patient ID template 51 includes various interface elements (e.g., shown schematically as a four-part configuration) that collectively serve as an identifier for health-related issues involving a particular patient, or in some instances a group of patients. Such a patient interface configuration may be implemented in a primary version of an interface template associated with a particular patient (e.g., attached to a body part, attached to a patient identifier, located proximate to a patient, incorporated with a patient support structure, located remotely from the patient, etc.), and also implemented in a complementary secondary version of the interface template that may be associated with a selected procedure intended for the particular patient or group of patients.

The primary template 55 shows an exemplary implementation of a composite three interface template that may be located in proximity to the particular patient. It will be noted that such a unitary interface template may have practical advantages as compared to using three separate patient ID templates 51. However it will be noted that multiple unitary templates as well as a composite multiple interface template allow for possible simultaneous matching engagement with three different selected patient procedures, and also for matching engagement with secondary procedure ID templates associated with different components of a health-related procedure.

The procedure ID template 60 includes various interface elements (e.g., shown schematically as a twin-type configuration) that collectively serve as an identifier for health-related issues involving a specified type of patient procedure.

The template 65 is shown schematically with an individual patient ID interface 66, a procedure ID interface 60a, and a group attribute ID interface 67. The individual patient ID interface 66 includes a different layout of the four-part configuration shown in patient ID template 51, but both interface configurations 51, 66 may serve as an identifier for the same particular patient. It will be noted that the procedure ID interface 60a incorporates the same twin-type configuration as shown in procedure ID template 60 in order for both interface configurations of 60, 60a to serve as an identifier for the same health-related procedure.

The triplet-type interface configuration shown in group attribute ID 67 provides capability for a template configuration to serve as an identifier of several patients that share a health-related relationship or affiliation.

It will be understood from the illustrated embodiments disclosed herein that some implementations may provide a patient identifier attachable to a bodily part of the particular patient, which patient identifier includes or is physically coupled to the interface template. In some instances the patient identifier may be attachable to a support structure for the particular patient, which patient identifier includes or is physically coupled to the interface template.

Further possible embodiments may provide an interface template in proximity to the particular patient, or provide an interface template located remotely from the particular patient. Other possible implementations may provide a plurality of interface templates including a first attribute interface serving as an identifier of the particular patient and a second attribute interface serving as an identifier of the health-related procedure. Such interface templates may be complementary to matching interface template configurations associated with a particular health-related procedure.

Some embodiments may provide a plurality of complementary interface templates that include a first attribute interface serving as an identifier of the particular patient and a second attribute interface serving as an identifier of a group of patients having a same or similar type of health-related issue. Other possible system features may include a plurality of complementary interface templates having two or more attribute interfaces each serving as an identifier of the particular patient to enable verifiable matching engagement with multiple complementary interface templates associated with a health-related procedure.

Some embodiments may further provide a computer program product including instructions encoded on storage or transmission media, which instructions implement a process for verification of the matching engagement between the interface template associated with the particular patient and the complementary interface template associated with a health-related procedure to be rendered to the particular patient.

Additional embodiments may provide a computer program product including instructions encoded on storage or transmission media, which instructions implement a process for providing a status indication regarding whether the matching engagement has occurred between the interface template associated with the particular patient and the complementary interface template associated with a health-related procedure to be rendered to the particular patient.

Further possible embodiments may provide a computer program product including instructions encoded on storage or transmission media, which instructions implement a process for preventing activation of the health-related procedure in the absence of satisfactory matching engagement between the interface template associated with the particular patient and the complementary interface template associated with a health-related procedure to be rendered to the particular patient.

Figure 2:
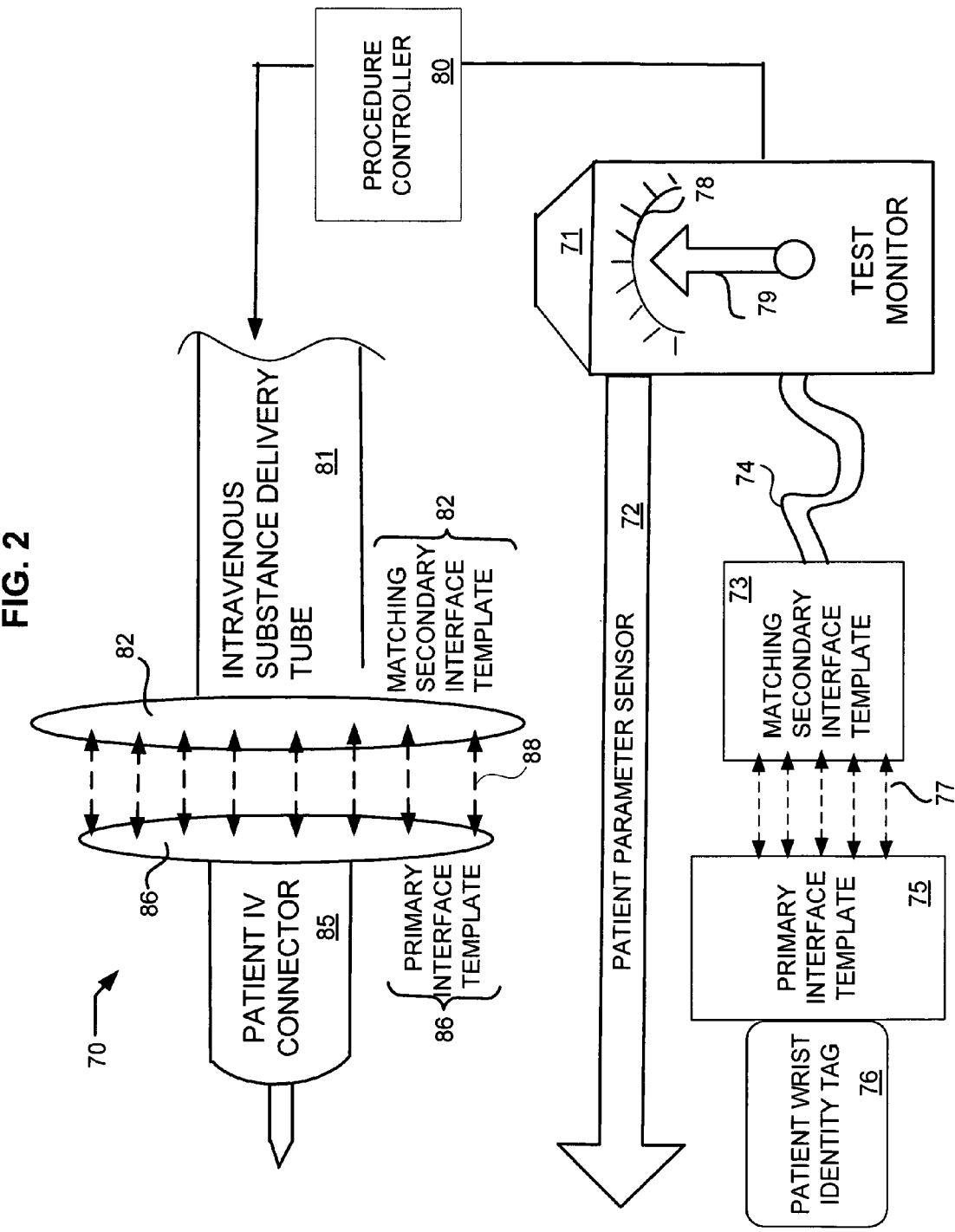
FIG. 2 is a schematic representation of exemplary embodiments that may be implemented in connection with a health-related procedure

The exemplary embodiments 70 of FIG. 2 disclose test monitor 71, patient parameter sensor 72, connector link 74, and procedure controller 80 operably coupled with intravenous substance delivery tube 81. A designated patient who is an intended recipient of the intravenous administration procedures may have a patient wrist identity tag 76 integral with or attachable to a primary interface template 75, and may also have a patient IV connector 85 integral with or attachable to primary interface template 86. The delivery of a health-related substance dosage to the designated patient via the intravenous substance delivery tube 81 may be coordinated by procedure controller 80 with output results generated by test monitor 71. The test monitor 71 may include an indicator arrow 79 that moves along a readout scale 78 to indicate an output result received from the patient parameter sensor 72.

The primary interface templates 75, 86 directly associated with the designated patient may be incorporated in a composite unit (e.g., see primary template 55 in FIG. 1), or may be incorporated in separate units (e.g., see patient ID template 51 in FIG. 1).

It will be noted that an implementation feature of the exemplary embodiments 70 includes a provision for both intravenous procedure components 71, 81 to have separate patient verification interconnections, respectively. Verification for usage of the test monitor 71 with the designated patient is accomplished by correlated interface engagement 77 between primary interface template 75 and matching secondary interface template 73. Verification for usage of the intravenous substance delivery tube 81 with such designated patient is accomplished by correlated interface engagement 88 between primary interface template 86 and matching secondary interface template 82.

Of course it will be understood that in some circumstances a health-related procedure may be configured to have a single patient verification interconnection linked to two or more components used to administer the procedure. In that regard the exemplary embodiments disclosed herein are for purposes of illustration only and are not intended to be limiting.

A substance administration device may be used in connection with administration of the selected procedure, wherein the secondary version of the interface template is associated with the substance administration device.

It will be understood from the various disclosures herein that an exemplary system embodiment may provide the secondary version of the interface template as an integral part of the substance administration device. A further implementation feature may provide a separate product component not integral with the substance administration device, wherein the separate product component includes the secondary version of the interface template as an integral part.

Some embodiments may include a status indicator that is operably coupled to the primary version or the secondary version of the interface template, wherein the status indicator confirms the satisfactory matching engagement between the primary and secondary versions of the interface template. A further system feature may include a control module operably coupled with the substance administration device to prevent activation of the substance administration device in the event there is no verifiable matching engagement between the primary and secondary versions of the interface template. In some instances the control module may be operably coupled with the substance administration device to allow activation of the substance administration device in the event there is confirmation of matching engagement between the primary and secondary versions of the interface template.

It will be understood that various features disclosed herein may be implemented with a diagnostic or testing or treatment device used in connection with administration of the selected health-related procedure, wherein the secondary version of the interface template is associated with such diagnostic or testing or treatment device.

Another exemplary implementation embodiment may include a health-related procedure that involves multiple components which may individually or collectively be integrated with or associated with the secondary version of the interface template.

Further exemplary implementations embodiments may include a patient identification system involving a health-related procedure for administering or dispensing substance dosages of various medications, dietary supplements, test fluids, anesthetics, treatment remedies, etc. (a complete listing is not reasonably possible). The related components used with such a procedure may be integrated with or associated with a complementary secondary version of the interface template.

Other implementations may provide a patient data record used in connection with administration of the selected health-related procedure, wherein the secondary version of the interface template is associated with the patient data record. In some instances a control module may include an access protocol to prevent read access to the patient data record in the event there is no verifiable matching engagement between the primary and secondary versions of the interface template. A further possible system feature may provide a control module that includes an access protocol to prevent write access to the patient data record in the event there is no verifiable matching engagement between the primary and secondary versions of the interface template.

Other possible data record aspects may include a control module having an access protocol to allow read access to the patient data record in the event there is confirmation of matching engagement between the primary and secondary versions of the interface template. Such access protocol may include one or more of the following type of output read access to the patient data record: hardcopy view, hardcopy printout, display monitor, remote access, text access, audio access, image access, fax access, hyperlinked access, and cross-reference link.

Another possible data record aspect may include a control module having an access protocol to allow write access to the patient data record in the event there is confirmation of matching engagement between the primary and secondary versions of the interface template. Such access protocol may allow one or more of the following type of input write access to the patient data record in the event there is confirmation of matching engagement between the primary and secondary versions of the interface template: handwritten, keyboarded, scanned, oral, faxed, remote transmittal, wireless transmittal, data modification, data deletion, hyperlinked data entry, and cross-reference link.

Figure 3:
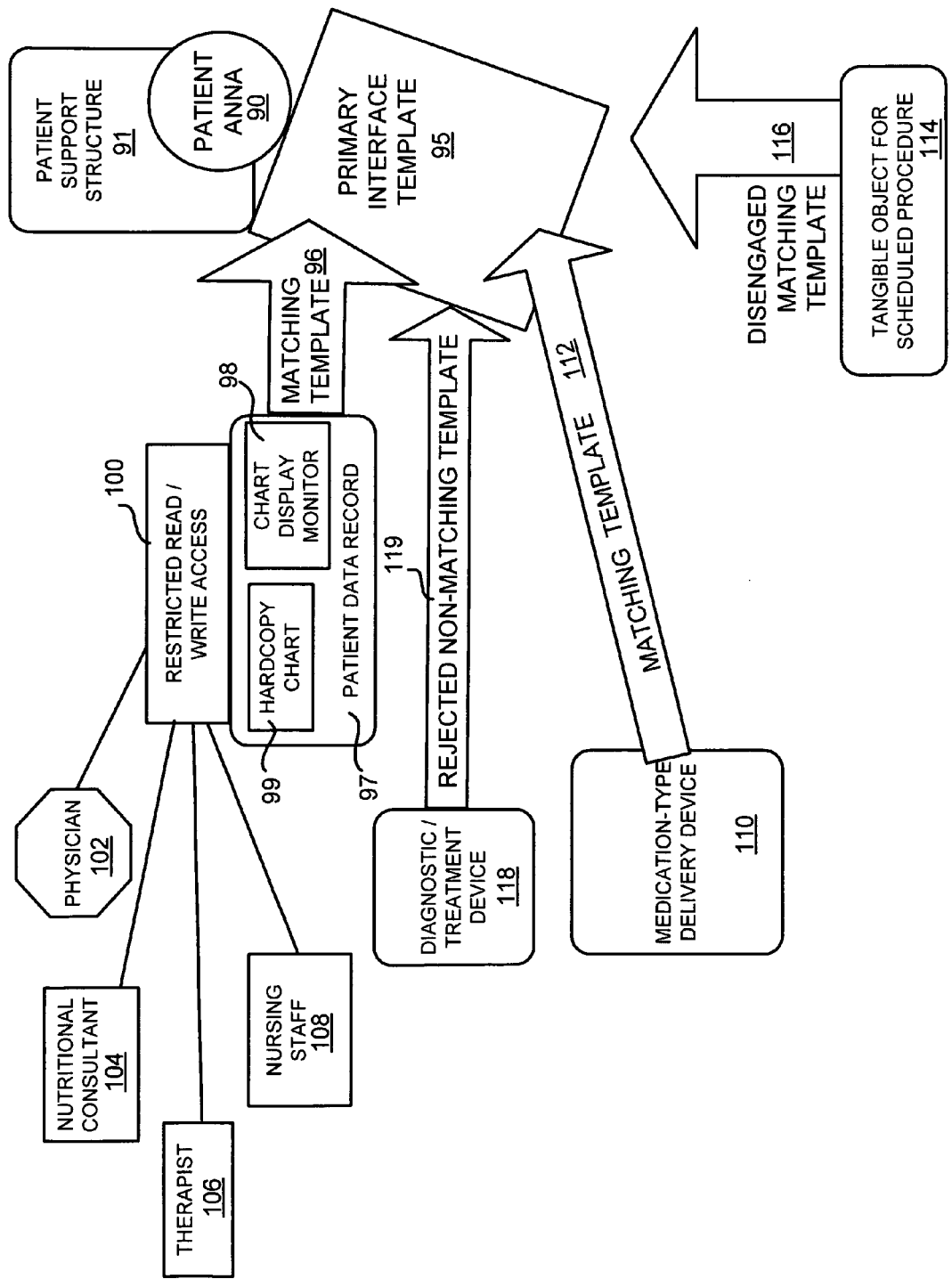
FIG. 3 is a schematic system diagram that illustrates various exemplary patient verification features.

Referring to the exemplary embodiments of FIG. 3, a patient Anna 90 may be temporarily or semi-permanently located with a patient support structure 91 (e.g., chair, bed, gurney, operating table, etc.). One or more primary interface templates 95 may be situated in proximity with patient Anna and/or in close proximity with her patient support structure 91.

It will be understood that health-related procedures can be administered to patient Anna 90 during confinement at a temporary care facility as well as during her daily life activities at a residence, home, work location, or traveling from one place to another. In that regard the exemplary patient verification arrangements disclosed herein are adaptable for use in many different types of patient environments.

An exemplary health-related procedure may include maintenance of a patient data record 97 that may be accessible to patient Anna 90 as well as to other authorized parties such as physician 102, nutritional consultant 104, therapist 106, and nursing staff 108. In order to help assure an acceptable assurance of data integrity, the patient data record 97 may include a restricted read/write access module 100. In some instances a verifiable engagement between Anna's primary interface template 95 and a matching template 96 associated with Anna's patient data record 97 may be required in order before allowing any "read" access (e.g., using hardcopy chart 99 or chart display monitor 98, etc.) or before allowing any "write" access (e.g., handwritten entry, keyboarded entry, scanned entry, etc.) to such patient data record 97.

An exemplary illustrated depiction in FIG. 3 shows the matching template 96 successfully linked together with primary interface template 95 based on a correlated interface engagement.

Other exemplary health-related procedures disclosed in the embodiments of FIG. 3 may involve the use of a medication-type delivery device 110, a tangible object for scheduled procedure 114, and a diagnostic/treatment device 118. Of course it will be understood that many other health-related procedures may also incorporate the patient verification techniques and features disclosed herein.

A further exemplary illustrated depiction in FIG. 3 shows the matching template 112 associated with medication-type deliver device 110 successfully linked together with primary interface template 95 based on a correlated interface engagement. It is noted that successful linkage involving primary patient interface templates may in some instances occur concurrently with multiple secondary interface templates (e.g., see templates 96, 112) associated with different health-related procedures.

Another exemplary illustrated depiction in FIG. 3 shows disengaged matching template 116 associated with tangible object for scheduled procedure 114 awaiting successful linkage with primary interface template 95.

An additional illustrated depiction in FIG. 3 shows an unsuccessful link attempted between non-matching template 119 that is associated with diagnostic/treatment device 118 and the primary interface template 95 that is associated with patient Anna 90.

Various implementation features may include providing an interface template associated with the particular patient, which interface template includes a customized interface configuration shaped for verifiable matching engagement with a complementary interface template associated with the health-related procedure. Some embodiments may provide one or more complementary interface templates associated with the health-related procedure. Some system features may provide multiple complementary interface templates that are each associated with a different product component, respectively. Another possible feature may provide one interface template associated with multiple product components.

Figure 4:
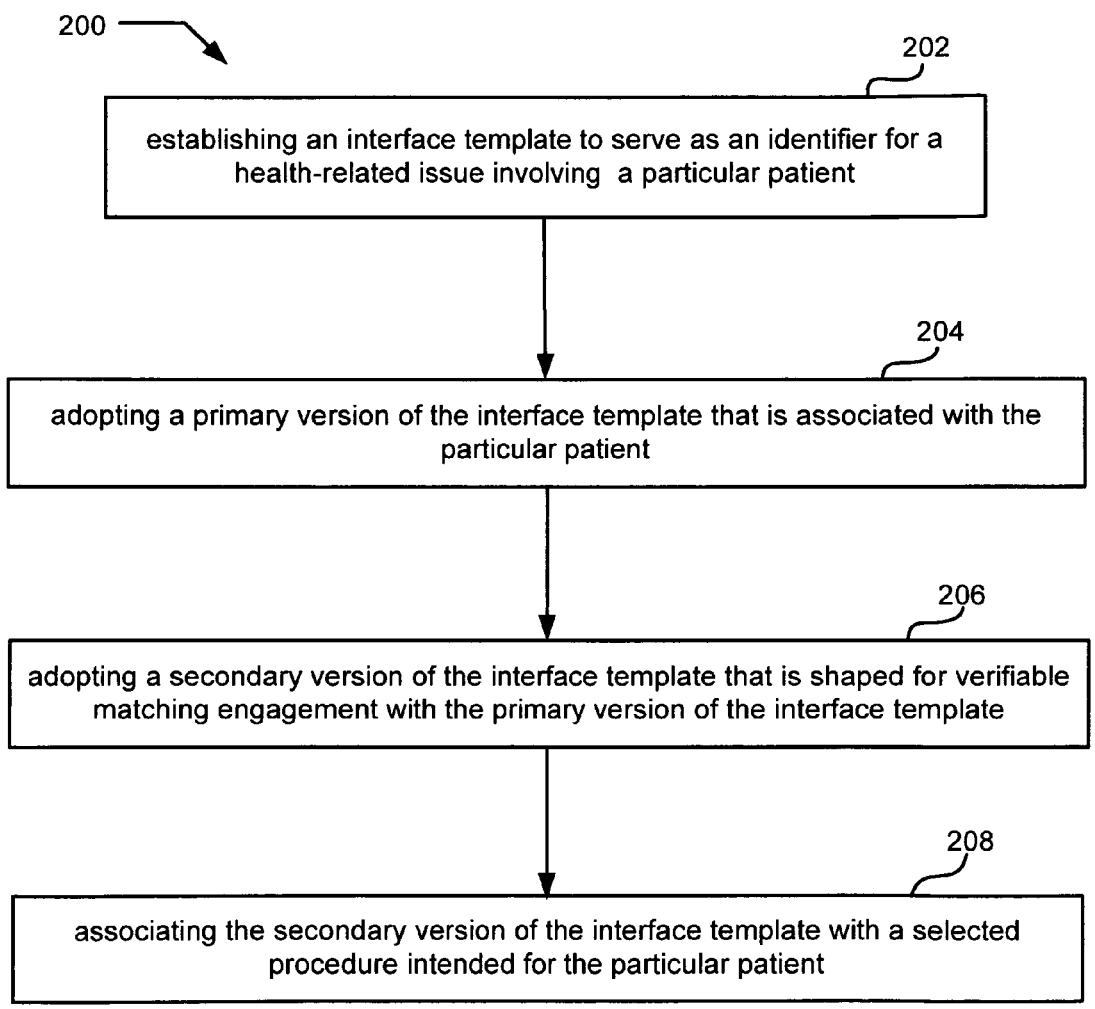
FIG. 4 is a high level flow chart for an exemplary process embodiment.

Referring to the high level flow chart of FIG. 4, an exemplary process embodiment 200 for patient verification includes establishing an interface template to serve as an identifier for a health-related issue involving a particular patient (block 202), adopting a primary version of the interface template that is associated with the particular patient (block 204), adopting a secondary version of the interface template that is shaped for verifiable matching engagement with the primary version of the interface template (block 206), and associating the secondary version of the interface template with a selected procedure intended for the particular patient (block 208).

Figure 5:
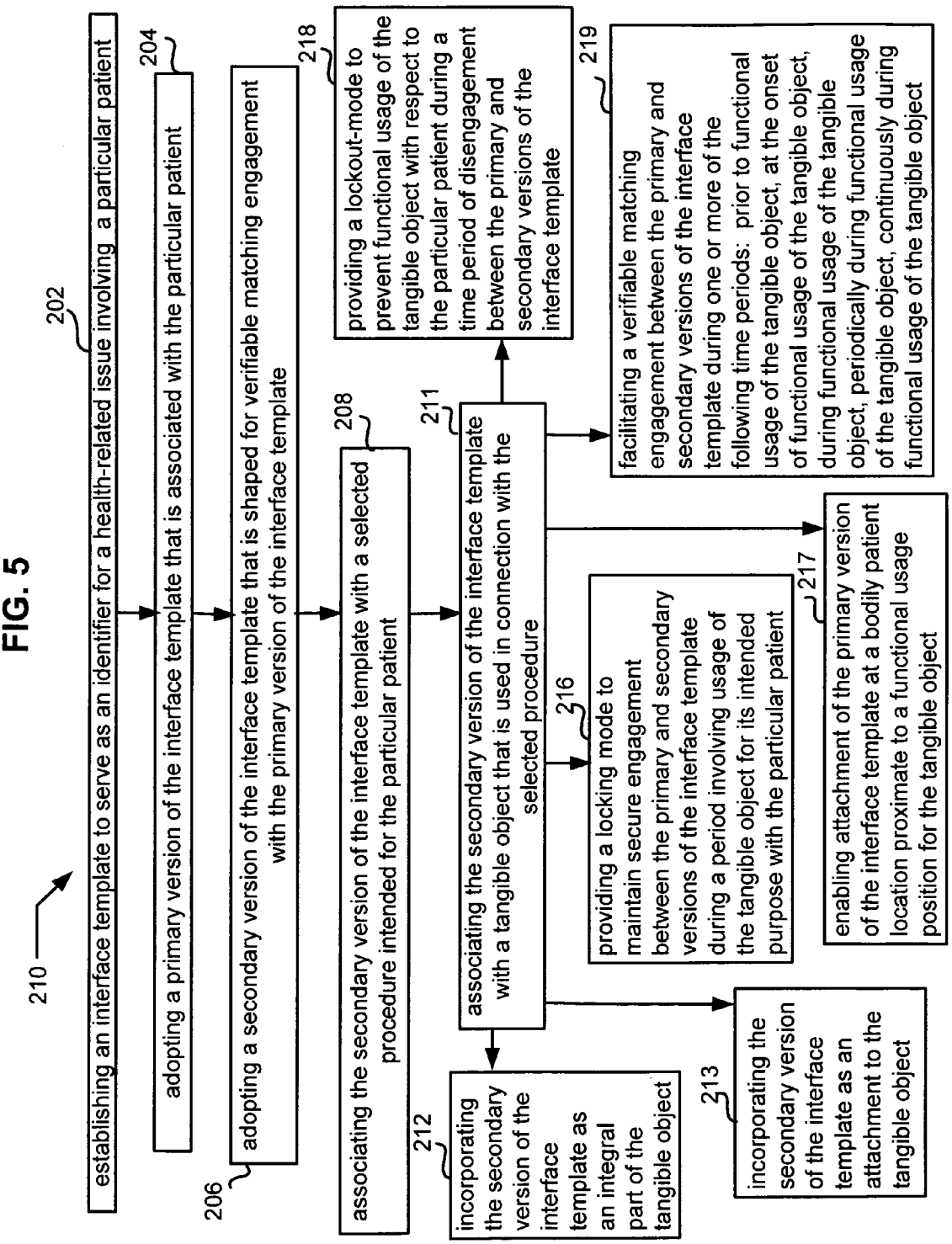
FIGS. 5-8 are flow charts showing more detailed aspects of various exemplary process embodiments.

The additional exemplary embodiment features 210 of FIG. 5 may include previously described process components 202, 204, 206, 208 in combination with associating the secondary version of the interface template with a tangible object that is used in connection with the selected procedure (block 211). Additional possible aspects may include incorporating the secondary version of the interface template as an integral part of the tangible object (block 212), and incorporating the secondary version of the interface template as an attachment to the tangible object (block 213).

Further possible features may include providing a locking mode to maintain secure engagement between the primary and secondary versions of the interface template during a period involving usage of the tangible object for its intended purpose with the particular patient (block 216), and enabling attachment of the primary version of the interface template at a bodily patient location proximate to a functional usage position for the tangible object (block 217).

FIG. 5 also discloses additional exemplary features including providing a lockout-mode to prevent functional usage of the tangible object with respect to the particular patient during a time period of disengagement between the primary and secondary versions of the interface template (block 218), and facilitating a verifiable matching engagement between the primary and secondary versions of the interface template during one or more of the following time periods: prior to functional usage of the tangible object, at the onset of functional usage of the tangible object, during functional usage of the tangible object, periodically during functional usage of the tangible object, continuously during functional usage of the tangible object (block 219).

Figure 6:
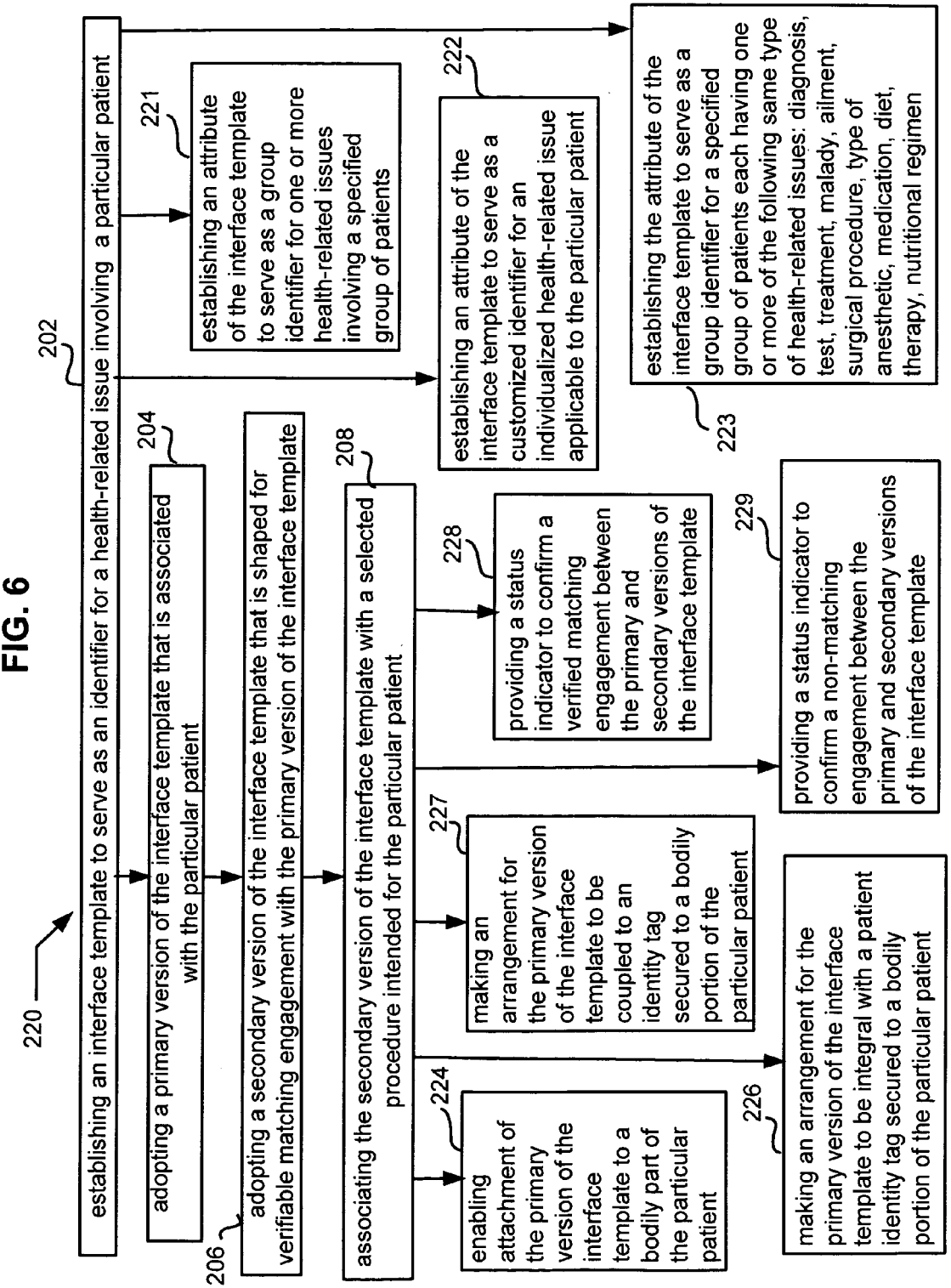

Referring to the exemplary embodiments 220 of FIG. 6, previously disclosed process components 202, 204, 206, 208 may be combined with other features relating to the primary version of the interface template. For example, possible aspects may include enabling attachment of the primary version of the interface template to a bodily part of the particular patient (block 224), making an arrangement for the primary version of the interface template to be integral with a patient identity tag secured to a bodily portion of the particular patient (block 226), and making an arrangement for the primary version of the interface template to be coupled to an identity tag secured to a bodily portion of the particular patient (block 227).

Other exemplary features may include providing a status indicator with an "ok" type of alert to indicate a verified matching engagement between the primary and secondary versions of the interface template (block 228), and providing a status indicator with a "warning" type of alert to indicate a non-matching engagement between the primary and secondary versions of the interface template (block 229).

Further possible implementation features shown in FIG. 6 may include establishing an attribute of the interface template to serve as a group identifier for one or more health-related issues involving a specified group of patients, (block 221), and establishing the attribute of the interface template to serve as a group identifier for a specified group of patients each having one or more of the following same type of health-related issues: diagnosis, test, treatment, malady, ailment, surgical procedure, type of anesthetic, medication, diet, therapy, and nutritional regimen (block 223), Another exemplary aspect may include establishing an attribute of the interface template to serve as a customized identifier for an individualized health-related issue applicable to the particular patient (block 222).

Figure 7:
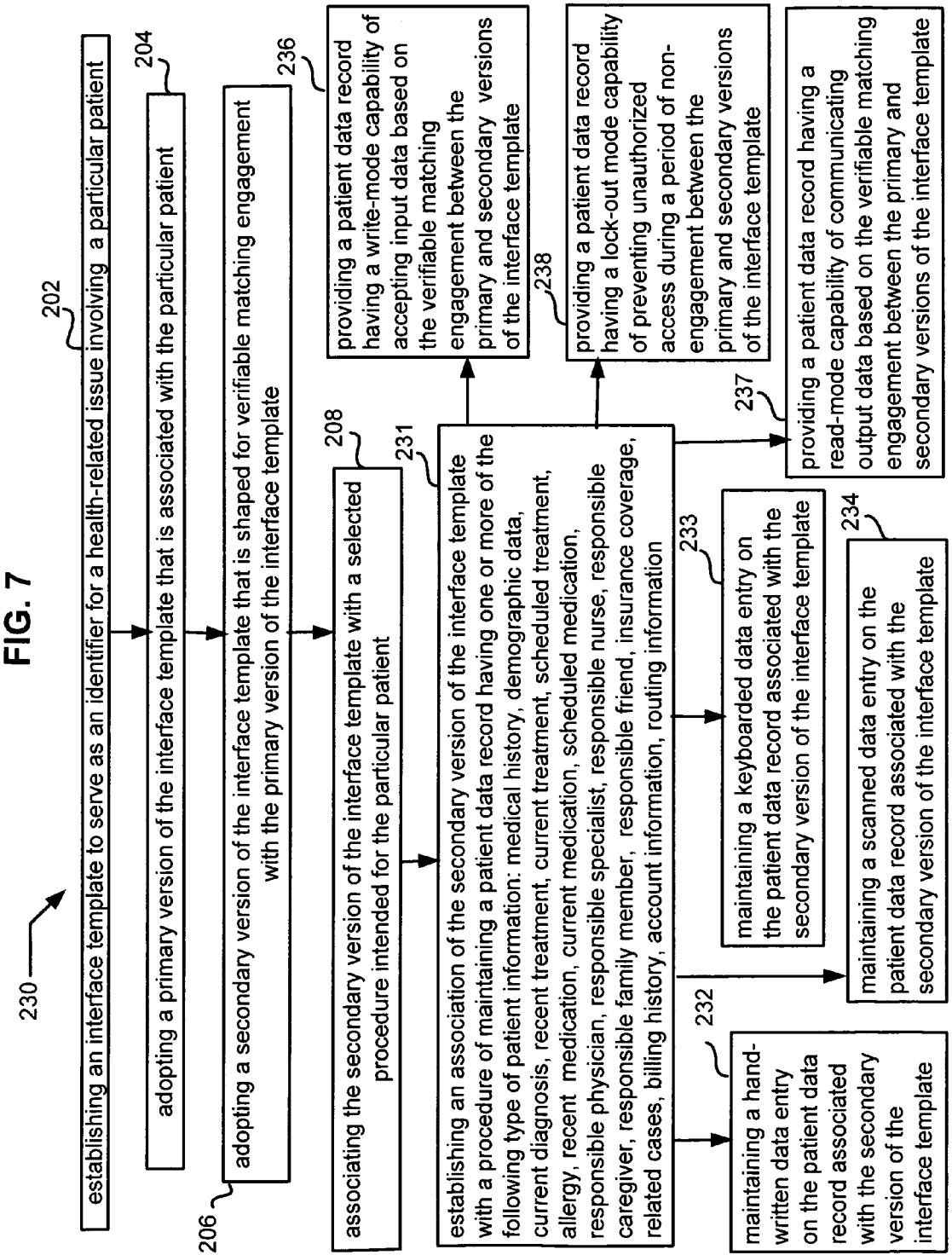

The exemplary process embodiments 230 shown in FIG. 7 may include previously described components 202, 204, 206, 208 along with establishing an association of the secondary version of the interface template with a procedure of maintaining a patient data record having one or more of the following type of patient information: medical history, demographic data, current diagnosis, recent treatment, current treatment, scheduled treatment, allergy, recent medication, current medication, scheduled medication, responsible physician, responsible specialist, responsible nurse, responsible caregiver, responsible family member, responsible friend, insurance coverage, related cases, billing history, account information, and routing information (block 231).

Further illustrated aspects that are possible include maintaining various types of data entries on the patient data record associated with the secondary version of the interface template, including a hand-written data entry (block 232), a keyboarded data entry (block 233), and a scanned data entry (block 234).

Further possible implementation features regarding the patient data record may include providing a patient data record having a write-mode capability of accepting input data based on the verifiable matching engagement between the primary and secondary versions of the interface template (block 236), and providing a patient data record having a read-mode capability of communicating output data based on the verifiable matching engagement between the primary and secondary versions of the interface template (block 237).

Another possible implementation feature may include providing a patient data record having a lock-out mode capability of preventing unauthorized access during a period of non-engagement between the primary and secondary versions of the interface template (block 238).

Figure 8:
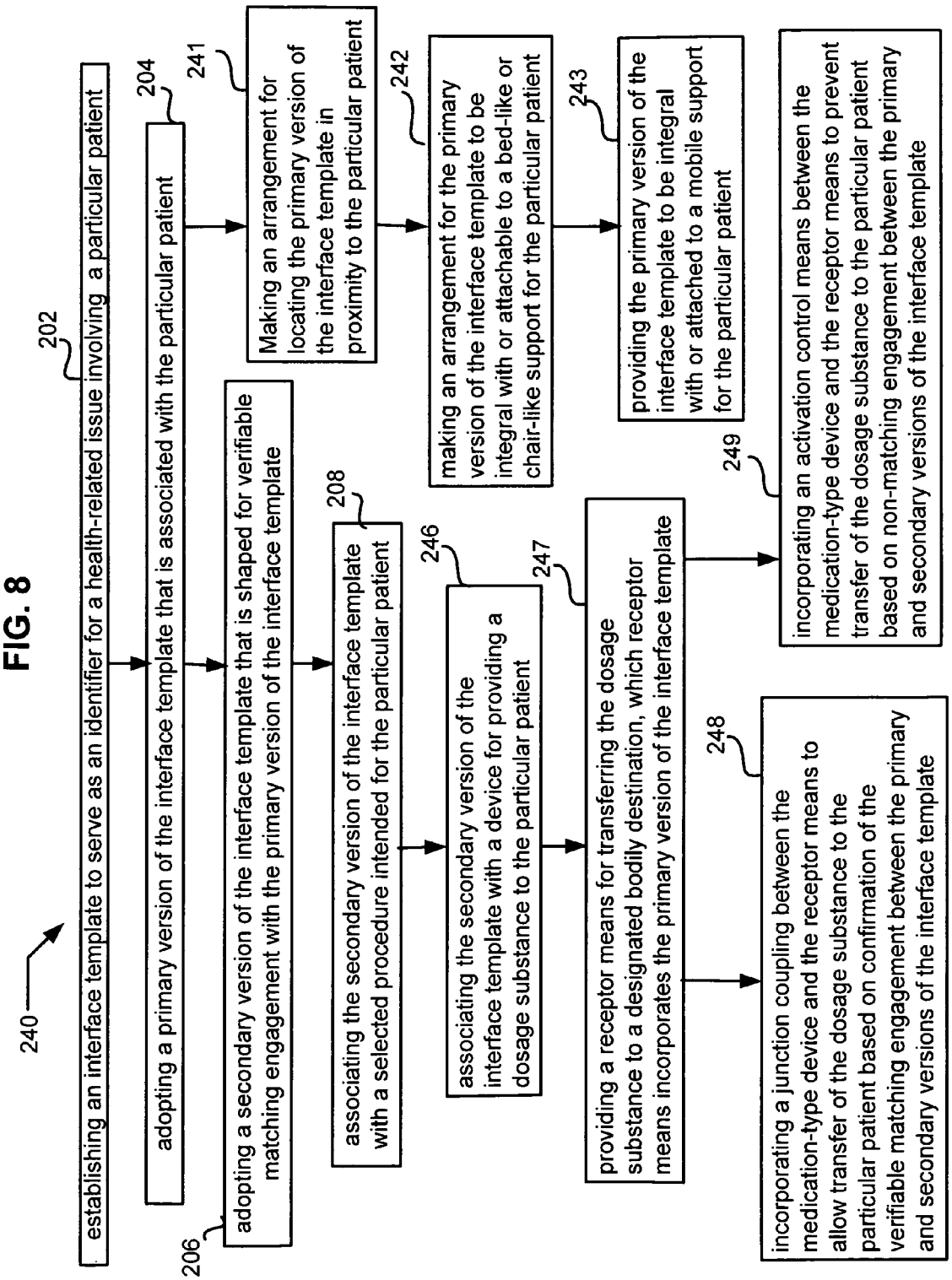

The detailed exemplary embodiment features 240 illustrated in FIG. 8 include previously described process components 202, 204, 206, 208 in combination with making an arrangement for locating the primary version of the interface template in proximity to the particular patient (block 241). Other possible aspects may include making an arrangement for the primary version of the interface template to be integral with or attachable to a bed-like or chair-like support for the particular patient (block 242). In some instances an exemplary embodiment feature may include providing the primary version of the interface template to be integral with or attached to a mobile support for the particular patient (block 243).

Other possible aspects shown in FIG. 8 include associating the secondary version of the interface template with a device for providing a dosage substance to the particular patient (block 246), providing a receptor means for transferring the dosage substance to a designated bodily destination, which receptor means incorporates the primary version of the interface template (block 247), and incorporating a junction coupling between the medication-type device and the receptor means to allow transfer of the dosage substance to the particular patient based on confirmation of the verifiable matching engagement between the primary and secondary versions of the interface template (block 248).

A further exemplary aspect may include incorporating an activation control means between the medication-type device and the receptor means to prevent transfer of the dosage substance to the particular patient based on non-matching engagement between the primary and secondary versions of the interface template (block 249).

Figure 9:
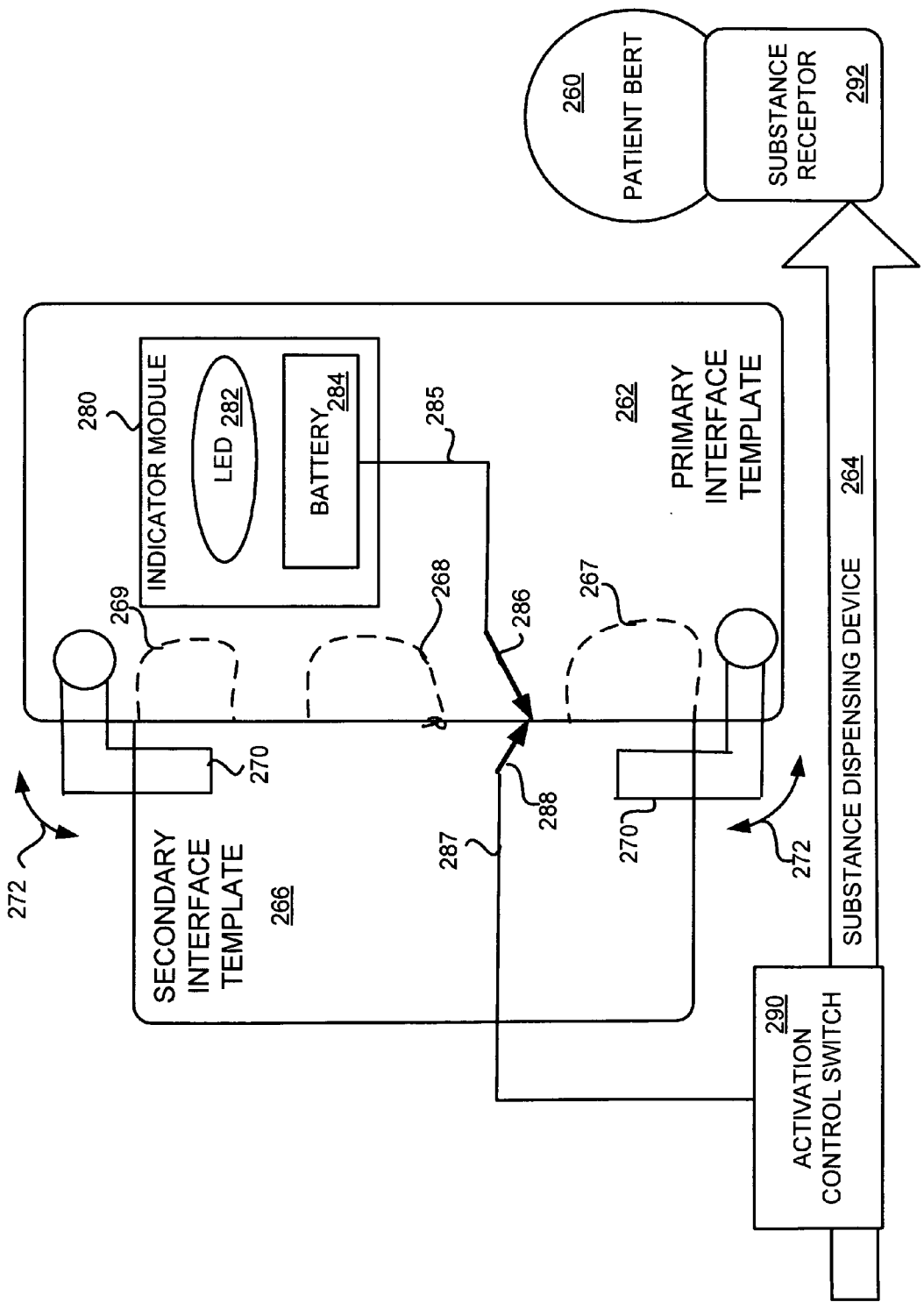
FIG. 9 is a schematic block diagram showing additional interface template embodiments.

The schematic block diagram of FIG. 9 illustrates an exemplary embodiment of a primary interface template 262 associated with patient Bert 260, and a matching secondary interface template 266 associated with substance dispensing device 264. The primary interface template 262 may include an indicator module 280 having a power source such as battery 284 and a status indicator such as light emitting diode (LED) 282. The primary interface template may also include a latching device such as pivotally mounted arms 270 that move back and forth (see arrows 272) between an unlatched position (with the primary interface template 262 and secondary interface template 266 disengaged—not shown) to a latched position with the primary interface template 262 and secondary interface template 266 in verifiable matching engagement (shown in FIG. 9).

Numerous types of matching interface shapes (e.g., pattern, projection, recess, matrix, contour, etc.) are possible for implementing a satisfactory matching engagement. In that regard, the illustrated version of the secondary interface template includes exemplary protrusions 267, 268, 269 (shown in phantom) that are shaped to form a customized pattern matching a complementary corresponding pattern (not shown) on the primary interface template 262.

A signal status line 285 connects battery 284 with a first conductive contact 286 on a surface portion of primary interface template 262. When full matching interface engagement occurs, a second conductive contact 288 is brought into adjacent relationship with the first conductive contact 286 to provide a closed circuit connection that establishes verification of a predetermined correct match-up between the substance dispensing device 264 and the intended recipient patient (or group of patients). Such verification may be confirmed by illumination of LED 282. Alternatively non-illumination of LED 282 is an indicator of non-engagement with the primary interface template 262.

Other functional consequences of such verified engagement may include a data entry provided to a patient data record (see patient data record 97 on FIG. 3), and transmission of a template engagement signal via status line 287 to activation control switch 290. Responsive to such template engagement signal, the activation control switch 290 serves as a junction coupling to enable delivery of a substance dosage via the substance dispensing device 264 to a substance receptor 292 for patient Bert 260. In the absence of such a template engagement signal, the activation control switch 290 remains closed to prevent delivery of any dosage through the substance dispensing device 264.

It will be understood that system embodiment features disclosed herein may be used with product components that include a device for dispensing a substance dosage for external administration to the particular patient, which device is associated with the interface template. In some instances the product components may include a device for dispensing a substance dosage for internal administration to the particular patient, which device is associated with the interface template.

Some embodiments may be implemented in a patient identification system for health-related procedures intended to be rendered to a specified group of patients having a same or similar type of health-related issue. An exemplary interface template may be associated with one or more product components, which interface template includes a customized interface configuration shaped for verifiable matching engagement with a complementary interface template associated with one or more of the patients in the specified group.

A possible group patient implementation aspect may provide a complementary interface template having a first attribute interface that includes a individualized ID configuration to serve as a customized identifier for a particular patient in the specified group, and also having a second attribute interface that includes a generic-type ID configuration to serve as an identifier for the specified group.

Another possible group aspect may provide a system having a complementary interface template that includes an attribute interface configuration to serve as an identifier associated with the health-related procedure.

Figure 10:
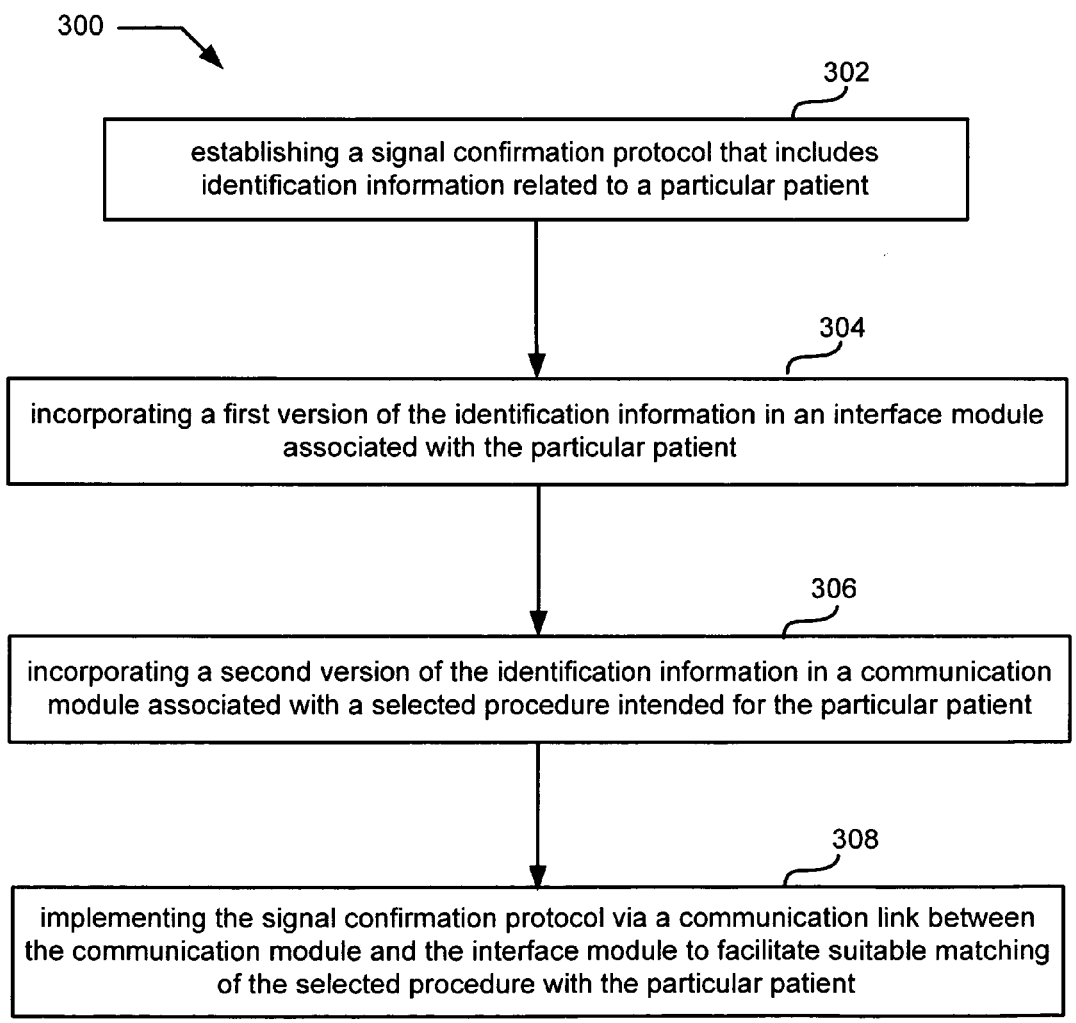
FIG. 10 is a high level flow chart for another exemplary process embodiment.

Referring to an exemplary embodiment 300 for a patient verification process shown in FIG. 10, possible components may include establishing a signal confirmation protocol that includes identification information related to a particular patient (block 302); incorporating a first version of the identification information in an interface module associated with the particular patient (block 304); incorporating a second version of the identification information in a communication module associated with a selected procedure intended for the particular patient (block 306); and implementing the signal confirmation protocol via a communication link between the communication module and the interface module to facilitate suitable matching of the selected procedure with the particular patient (block 308).

Figure 11:
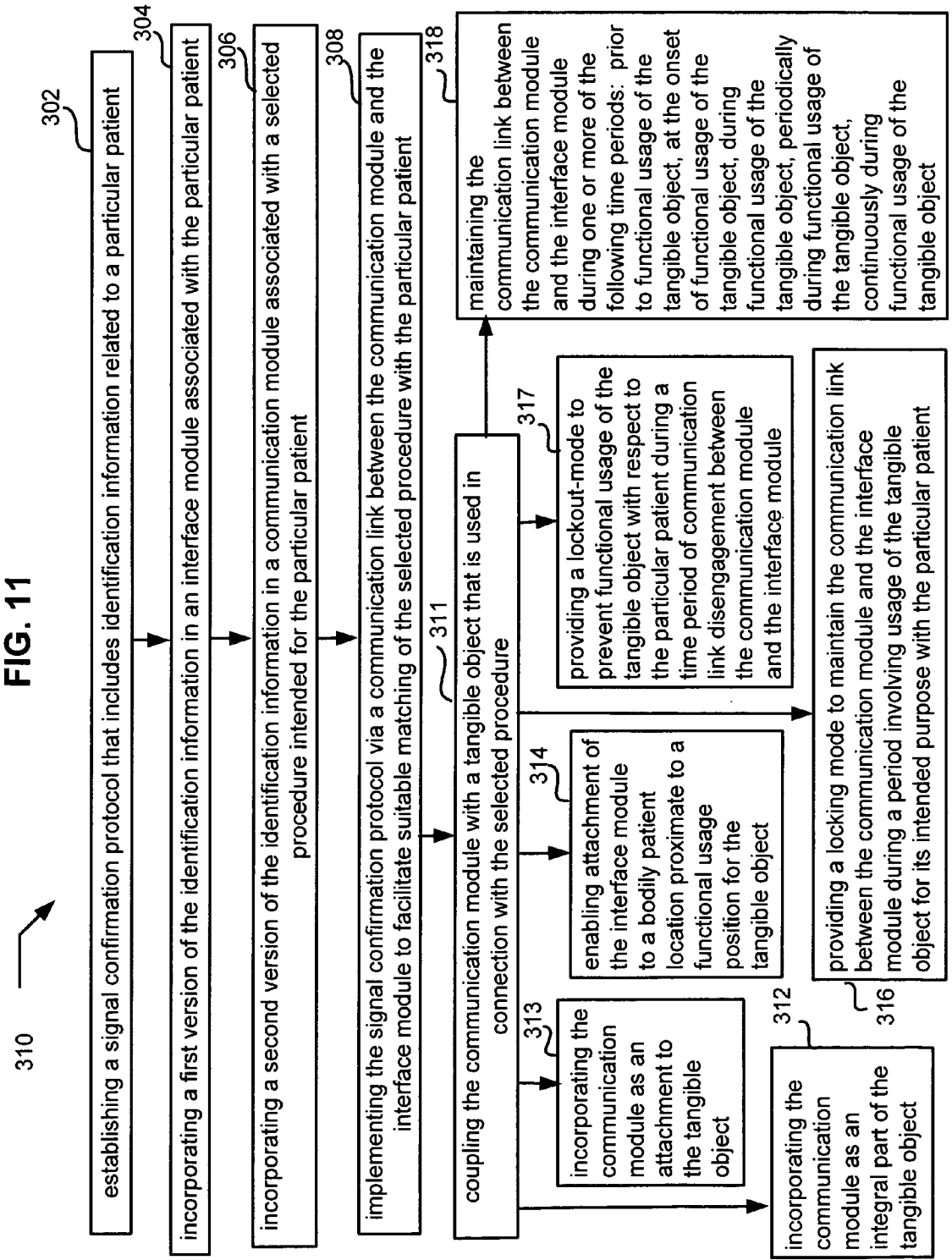
FIGS. 11-14 are flow charts that illustrate more detailed aspects of various exemplary patient verification process implementations.

The exemplary process embodiment features 310 illustrated in FIG. 11 include previously described components 302, 304, 306, 308 in combination with coupling the communication module with a tangible object that is used in connection with the selected procedure (block 311). Additional possible features may include incorporating the communication module as an integral part of the tangible object (block 312), and in some instances may include incorporating the communication module as an attachment to the tangible object (block 313).

Other possible aspects may include enabling attachment of the interface module to a bodily patient location proximate to a functional usage position for the tangible object (block 314), providing a locking mode to maintain the communication link between the communication module and the interface module during a period involving usage of the tangible object for its intended purpose with the particular patient (block 316), and providing a lockout-mode to prevent functional usage of the tangible object with respect to the particular patient during a time period of communication link disengagement between the communication module and the interface module (block 317).

Additional possible features illustrated in FIG. 11 include maintaining the communication link between the communication module and the interface module during one or more of the following time periods: prior to functional usage of the tangible object, at the onset of functional usage of the tangible object, during functional usage of the tangible object, periodically during functional usage of the tangible object, continuously during functional usage of the tangible object (block 318).

Figure 12:
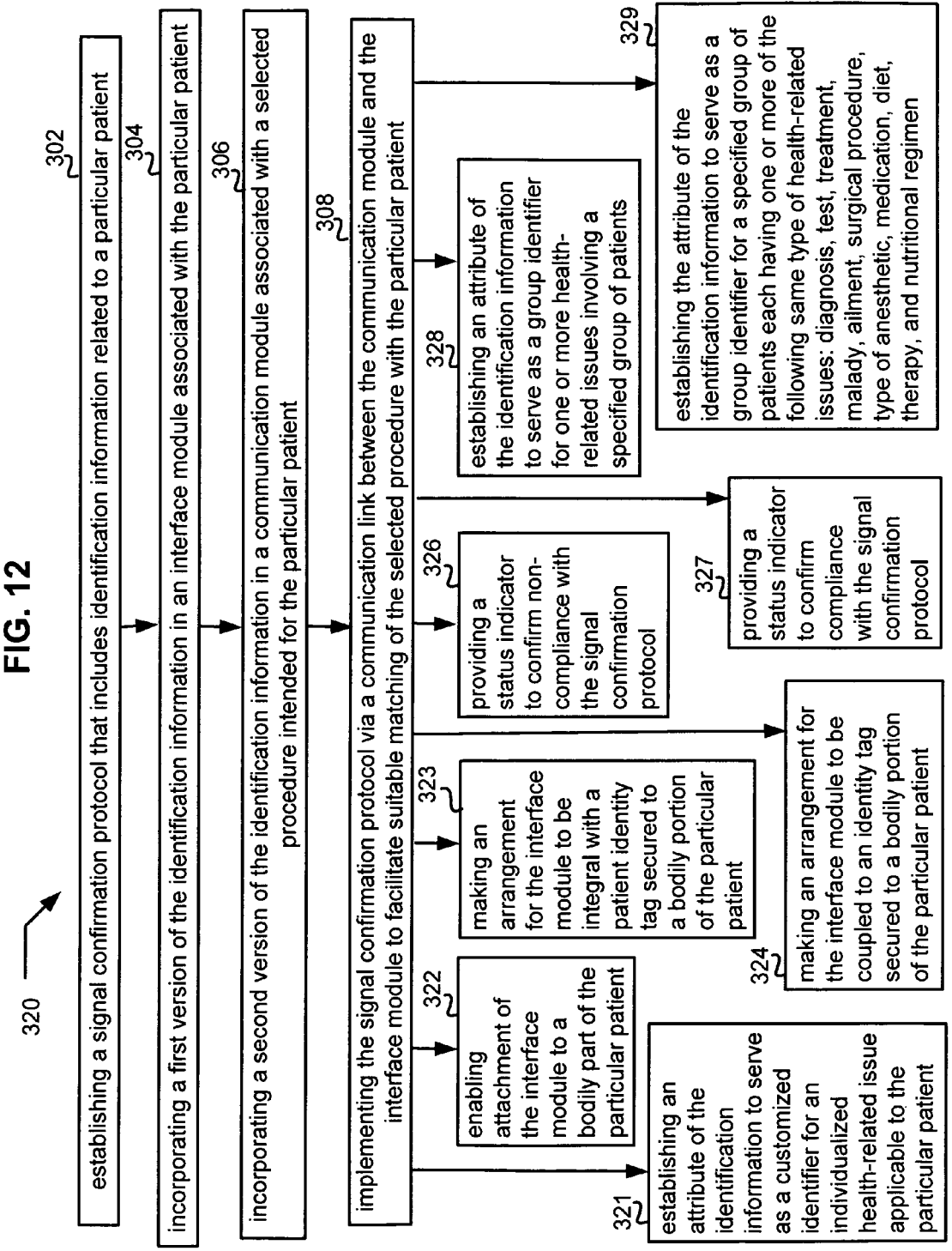

Referring to the illustrated exemplary features 320 of FIG. 12, previously described process components 302, 304, 306, 308 may be combined with other aspects such as establishing an attribute of the identification information to serve as an individualized health-related issue applicable to the particular patient (block 321).

Other possible aspects include enabling attachment of the interface module to a bodily part of the particular patient (block 322), making an arrangement for the interface module to be integral with a patient identity tag secured to a bodily portion of the particular patient (block 323), and making an arrangement for the interface module to be coupled to an identity tag secured to a bodily portion of the particular patient (block 324).

FIG. 12 also illustrates other possible process features including providing a status indicator to confirm compliance (block 327) as well as non-compliance (block 326) with the signal confirmation protocol.

Other possible implementation features may include establishing an attribute of the identification information to serve as a group identifier for one or more health-related issues involving a specified group of patients (block 328), and establishing the attribute of the identification information to serve as a group identifier for a specified group of patients each having one or more of the following same type of health-related issues: diagnosis, test, treatment, malady, ailment, surgical procedure, type of anesthetic, medication, diet, therapy, and nutritional regimen (block 329).

Figure 13:
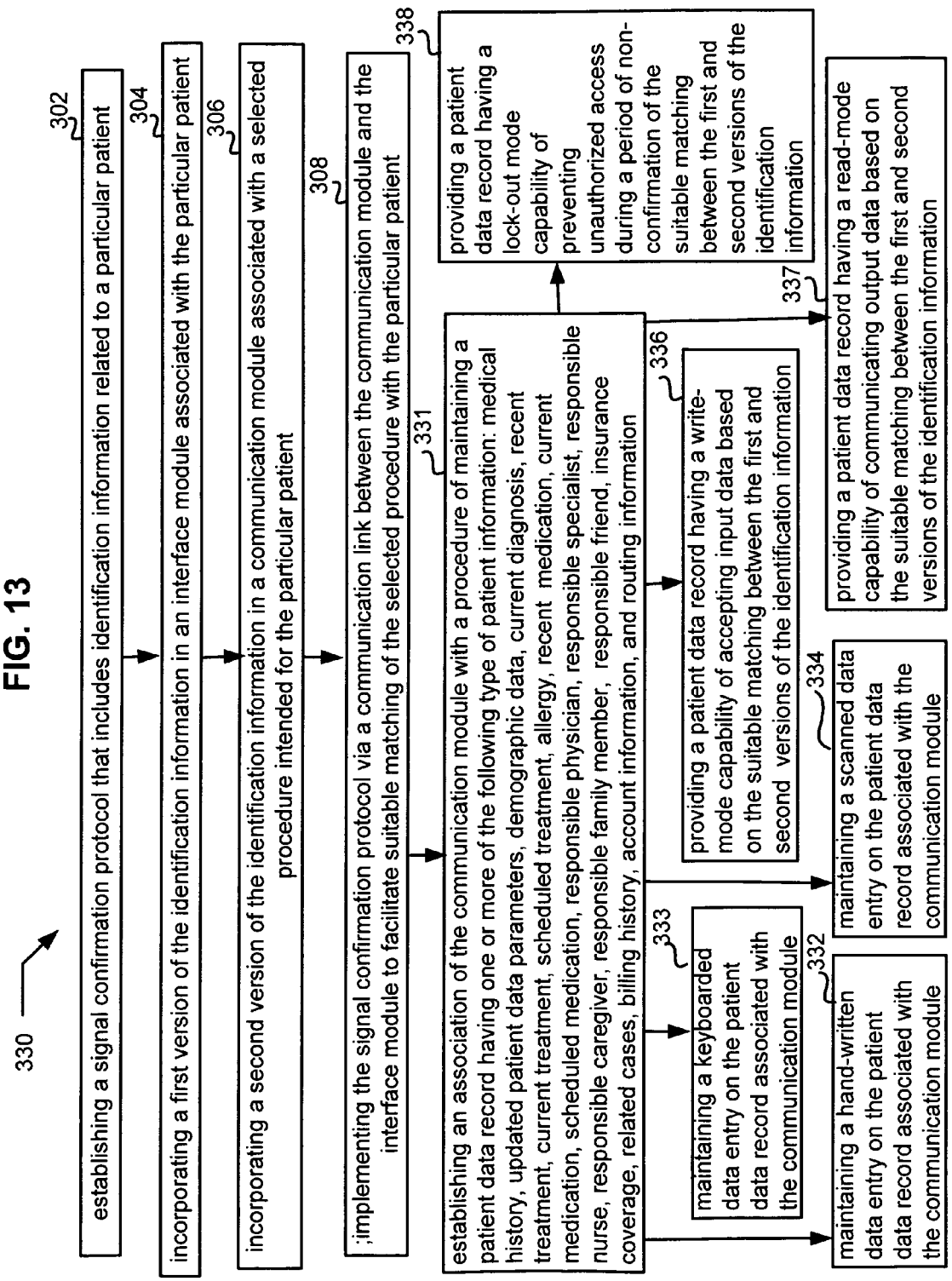

Referring to FIG. 13, various exemplary embodiment features 330 include previously described components 302, 304, 306, 308 along with other possible aspects related to patient data records. For example, some implementations may include establishing an association of the communication module with a procedure of maintaining a patient data record having one or more of the following type of patient information: medical history, updated patient data parameters, demographic data, current diagnosis, recent treatment, current treatment, scheduled treatment, allergy, recent medication, current medication, scheduled medication, responsible physician, responsible specialist, responsible nurse, responsible caregiver, responsible family member, responsible friend, insurance coverage, related cases, billing history, account information, and routing information (block 331).

Other possible aspects include maintaining a hand-written data entry (block 332) or a keyboarded data entry (block 333) or a scanned data entry (block 334) on the patient data record associated with the communication module. Further possible aspects include providing a patient data record having a write-mode capability of accepting input data (block 336) or a read-mode capability of communicating output data (block 336) based on the suitable matching between the first and second versions of the identification information.

Another possible feature includes providing a patient data record having a lock-out mode capability of preventing unauthorized access during a period of non-confirmation of the suitable matching between the first and second versions of the identification information (block 338).

Figure 14:
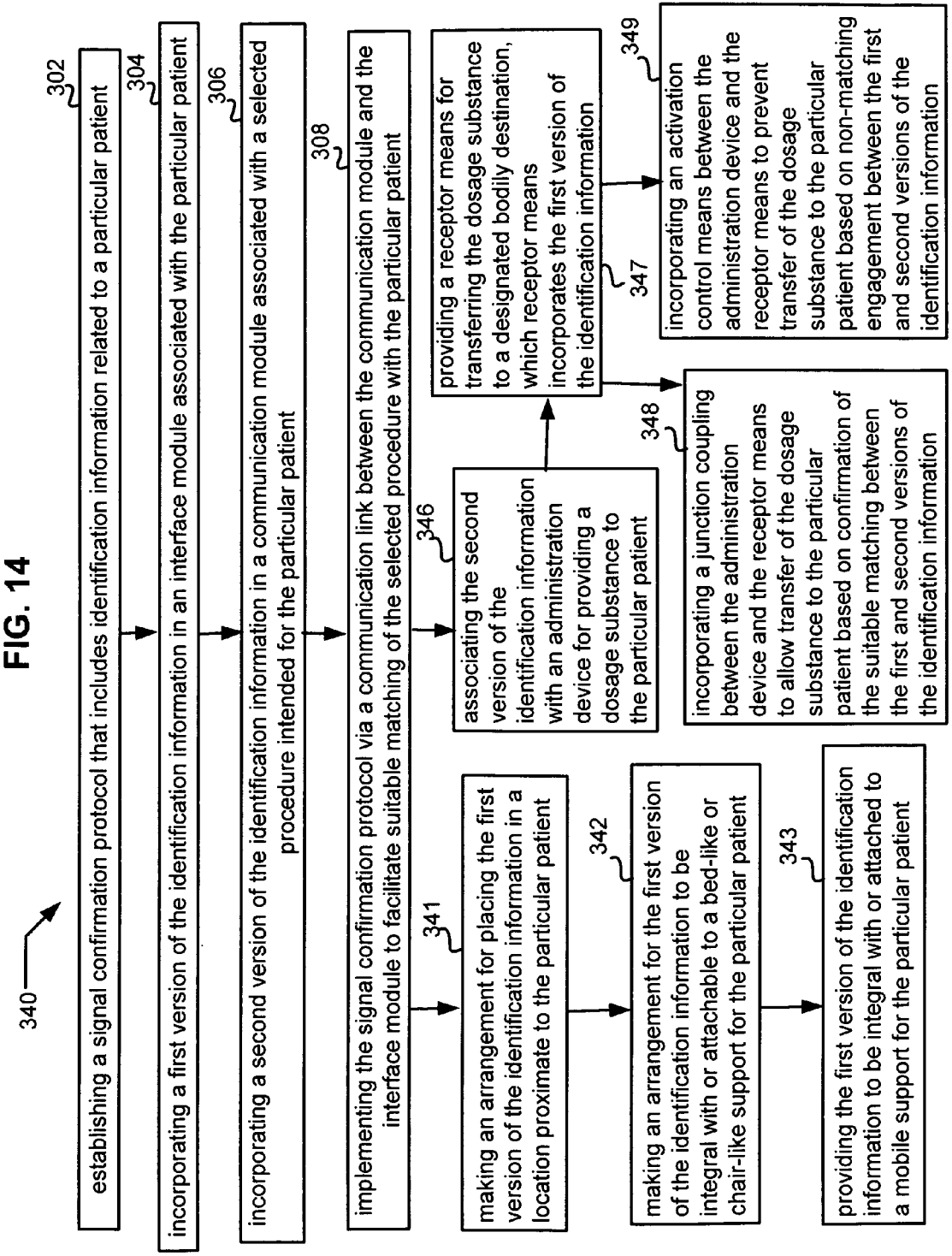

The detailed embodiment features 340 illustrated in FIG. 14 include previous described process components 302, 304, 306, 308 in combination with possible aspects related to various versions of identification information. For example, possible implementation aspects may include making an arrangement for placing a first version of the identification information in a location proximate to the particular patient (block 341), making an arrangement for the first version of the identification information to be integral with or attachable to a bed-like or chair-like support for the particular patient (block 342), and providing the first version of the identification information to be integral with or attached to a mobile support for the particular patient (block 343).

Additional possible features may include associating a second version of the identification information with an administration device for providing a dosage substance to the particular patient (block 346), and providing a receptor means for transferring the dosage substance to a designated bodily destination, which receptor means incorporates the first version of the identification information (block 347).

Other exemplary features may include incorporating a junction coupling between the administration device and the receptor means to allow transfer of the dosage substance to the particular patient based on confirmation of the suitable matching between the first and second versions of the identification information (block 348), and incorporating an activation control means between the administration device and the receptor means to prevent transfer of the dosage substance to the particular patient based on non-matching engagement between the first and second versions of the identification information (block 349).

It will be understood that the signal confirmation protocol may be implemented via various types of communication links (e.g., local link, remote link, wireless link, wired link, conductive link, non-conductive link, etc.), and such communication link may be temporarily or permanently established between an interface module associated with a particular patient and a communication module associated with a selected procedure intended for the particular patient. It will be further understood that such communication links may be dedicated or shared, depending on the circumstances. The exemplary embodiments are disclosed for purposes of illustration only, and are not intended to be limiting.

Figure 15:
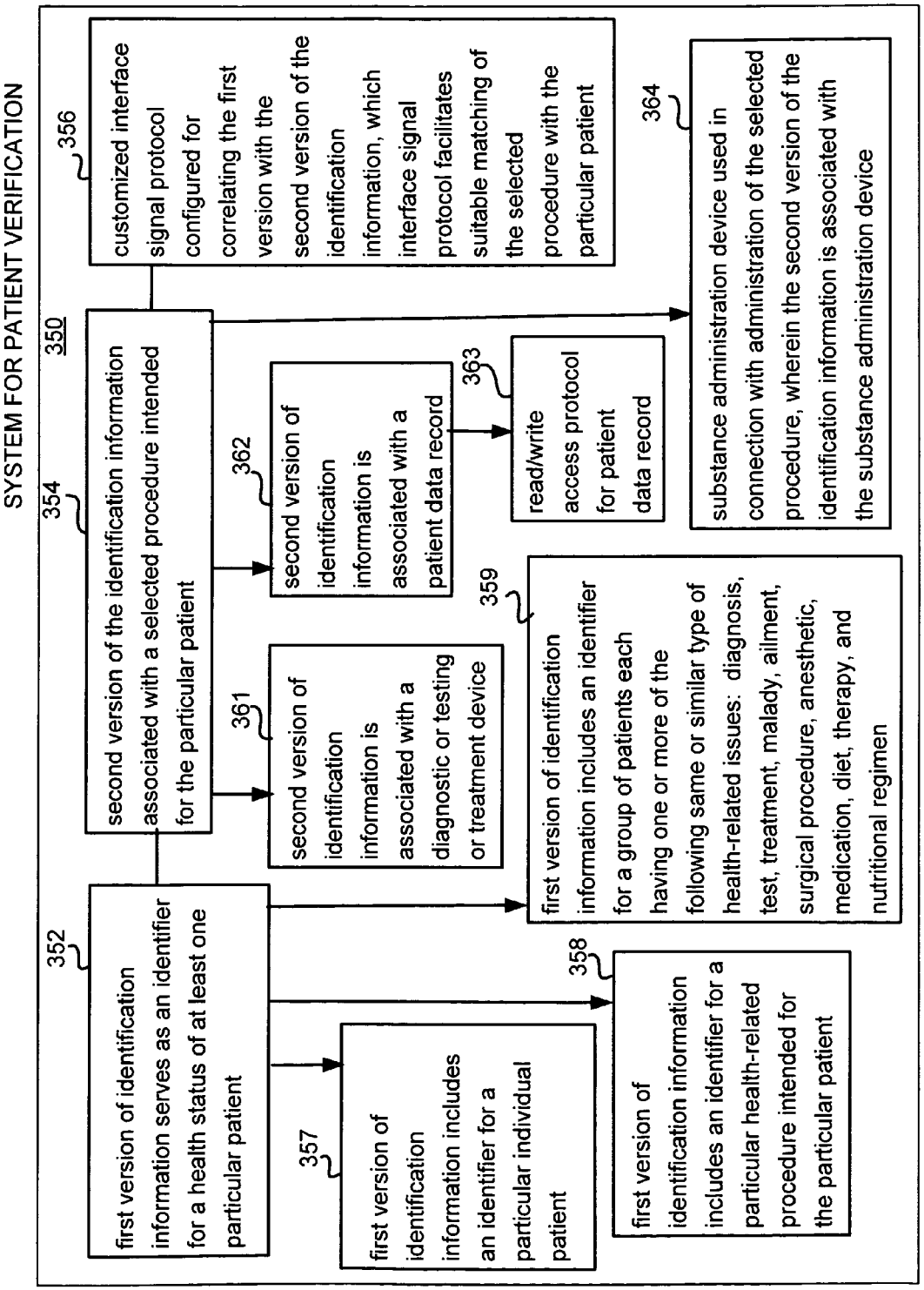
FIG. 15 is a schematic block diagram for a patient verification system.

The schematic block diagram of FIG. 15 illustrates an exemplary system for patient verification 350 that includes a first version of identification information that serves as an identifier for a health status of at least one particular patient (block 352), a second version of the identification information that is associated with a selected procedure intended for the particular patient (block 354); and a customized interface signal protocol configured for correlating the first version with the second version of the identification information, which interface signal protocol facilitates suitable matching of the selected procedure with the particular patient (block 356).

Additional possible system components may provide a first version of identification information that includes an identifier for a particular individual patient (block 357), and in some instances an identifier for a particular health-related procedure intended for the particular patient (block 358). Further possible system components may provide first version of identification information includes an identifier for a group of patients each having one or more of the following same or similar type of health-related issues: diagnosis, test, treatment, malady, ailment, surgical procedure, anesthetic, medication, diet, therapy, and nutritional regimen (block 359).

Other possible system features may provide a second version of identification information associated with a diagnostic or testing or treatment device (block 361), wherein the diagnostic or testing or treatment device may be used in connection with administration of a selected procedure intended for a particular patient. It will be understood that a related implementation features may provide the second version of the identification information as an attachment to or as an integral part of the diagnostic or testing or treatment device.

Further possible system aspects may provide a separate product component not integral with the diagnostic or testing or treatment device, wherein the separate product component includes the second version of the identification information as an attachment to or as an integral part of the diagnostic or testing or treatment device.

Another possible system feature may provide a status indicator that is operably coupled to the first version or the second version of the identification information, wherein the status indicator confirms suitable matching of the selected procedure with the particular patient.

A further possible system feature may provide a control module configured to prevent activation of the diagnostic or testing or treatment device in the event there is an absence of suitable matching of the selected procedure with the particular patient. In some implementations a control module may be configured to allow activation of the diagnostic or testing or treatment device in the event there is confirmation of suitable matching of the selected procedure with the particular patient.

A further possible system feature may provide a second version of identification information associated with a patient data record (block 362), wherein the patient data record may be used in connection with administration of a selected procedure intended for a particular patient. A possible related feature may include a read/write access protocol (block 363) for the patient data record.

Other related system features regarding a patient data record may include the second version of the identification information as an attachment to or as an integral part of the patient data record. A further system aspect may provide a separate product component not integral with the patient data record, wherein the separate product component includes the second version of the identification information as an attachment to or as an integral part of the patient data record.

Further system aspects may include a status indicator that is operably coupled to the first version or the second version of the identification information, wherein the status indicator confirms the suitable matching of the patient data record with the particular patient. Some implementation may include a control module configured to prevent activation of the patient data record in the event there is an absence of suitable matching of the patient data record with the particular patient. An additional possible implementation feature may include a control module configured to allow activation of the patient data record in the event there is confirmation of suitable matching of the selected procedure with the particular patient.

Additional aspects related to patient data records may include an access protocol to prevent read access to the patient data record in the event there is an absence of suitable matching of the selected procedure with the particular patient. Such an access protocol may in some instances prevent write access to the patient data record in the event there is an absence of suitable matching of the selected procedure with the particular patient.

Other possible implementation features may include an access protocol configured to allow read access to the patient data record in the event there is confirmation of suitable matching of the selected procedure with the particular patient. In some instances the access protocol may be configured to allow write access to the patient data record in the event there is correlation between the first and second versions of the identification information.

It will be understood that an exemplary access protocol may allow one or more of the following type of input write access to the patient data record in the event there is correlation between the first and second versions of the identification information: handwritten, keyboarded, scanned, oral, faxed, remote transmittal, wireless transmittal, data modification, data deletion, hyperlinked data entry, and cross-reference link.

Some exemplary embodiments may include an access protocol that provides one or more of the following type of output read access to the patient data record: hardcopy view, hardcopy printout, display monitor, remote access, text access, audio access, image access, fax access, hyperlinked access, and cross-reference link.

FIG. 15 shows another possible system aspect that provides a first version of identification information including an identifier for a group of patients each having one or more of the following same or similar type of health-related issues: diagnosis, test, treatment, malady, ailment, surgical procedure, anesthetic, medication, diet, therapy, and nutritional regimen (block 359).

A further possible system aspect may include a substance administration device used in connection with administration of the selected procedure, wherein a second version of identification information is associated with the substance administration device (block 364). It will be understood that additional system aspects related to a substance administration device may provide a second version of the identification information as an integral part of the substance administration device. Some implementations may include a separate product component not integral with the substance administration device, wherein the separate product component includes the second version of the identification information as an integral part.

Additional possible system features may include a status indicator that is operably coupled to a first version or a second version of the identification information, wherein the status indicator confirms the correlation between the first and second versions of the identification information.

Some exemplary system embodiments may include a control module operably coupled with the substance administration device to prevent activation of the substance administration device in the event there is an absence of correlation between first and second versions of the identification information. In some instances a control module may be operably coupled with the substance administration device to allow activation of the substance administration device in the event there is confirmation of correlation between first and second versions of the identification information.

Figure 16:
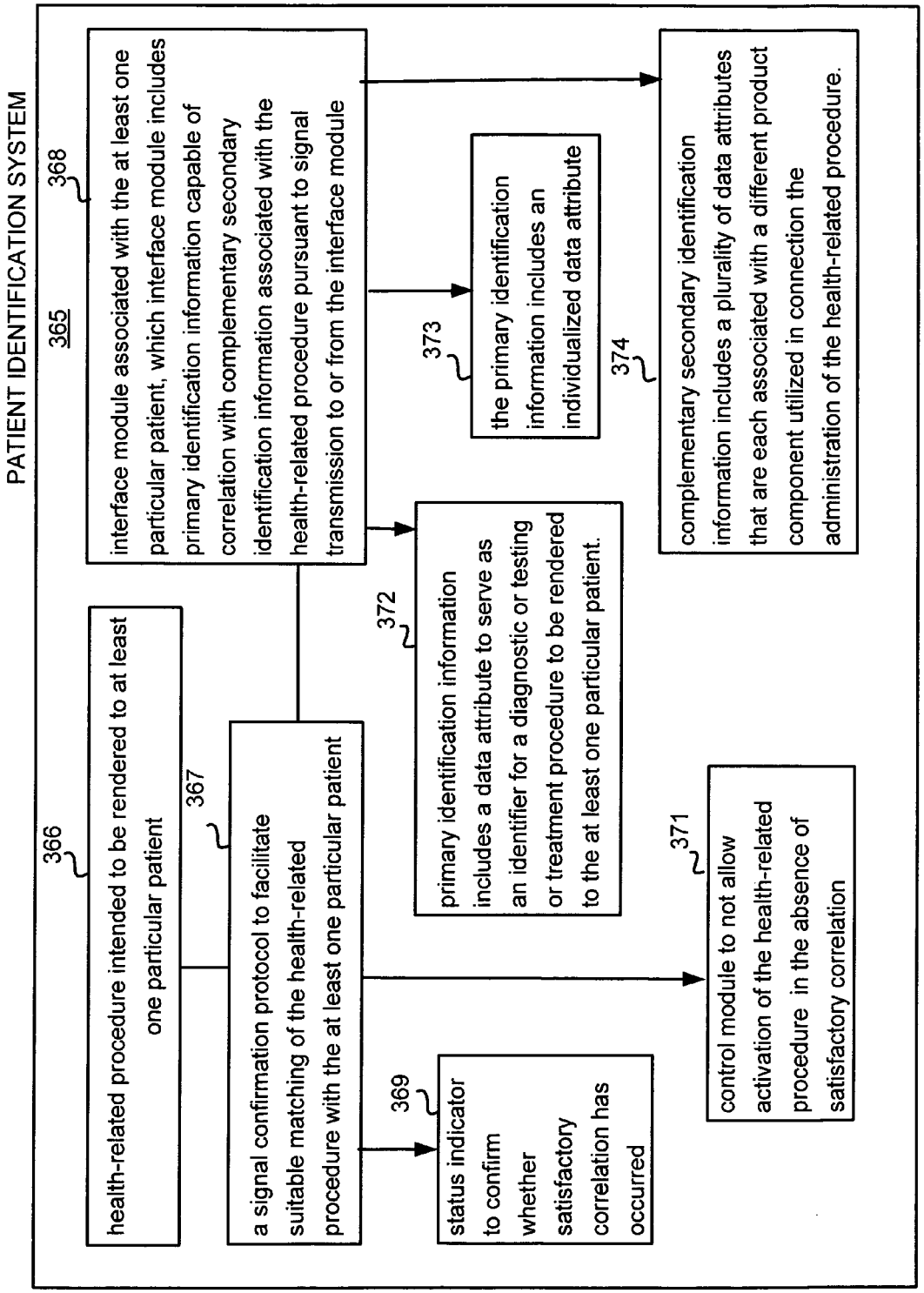
FIGS. 16-19 schematically illustrate additional patient identification system embodiments.

The exemplary patient identification system embodiment 365 of FIG. 16 includes a health-related procedure that is intended to be rendered to at least one particular patient (block 366); a signal confirmation protocol to facilitate suitable matching of the health-related procedure with the at least one particular patient (block 367); and an interface module associated with the at least one particular patient, which interface module includes primary identification information capable of correlation with complementary secondary identification information associated with the health-related procedure pursuant to signal transmission to or from the interface module (block 368).

Further system aspects may include a status indicator to confirm whether satisfactory correlation has occurred (block 369) between a particular patient and a health-related procedure. In some instances an exemplary control module may be configured to not allow activation of the health-related procedure in the absence of satisfactory correlation (block 371).

Another system aspect may provide primary identification information that includes a data attribute to serve as an identifier for a diagnostic or testing or treatment procedure to be rendered to at least one particular patient (block 372).

Additional possible system aspects may provide primary identification information including an individualized data attribute (block 373) that may serve as a customized identifier for at least one particular patient. A further exemplary system aspect may provide complementary secondary identification information including a plurality of data attributes that are each associated with a different product component utilized in connection with the administration of the health-related procedure (block 374).

Figure 17:
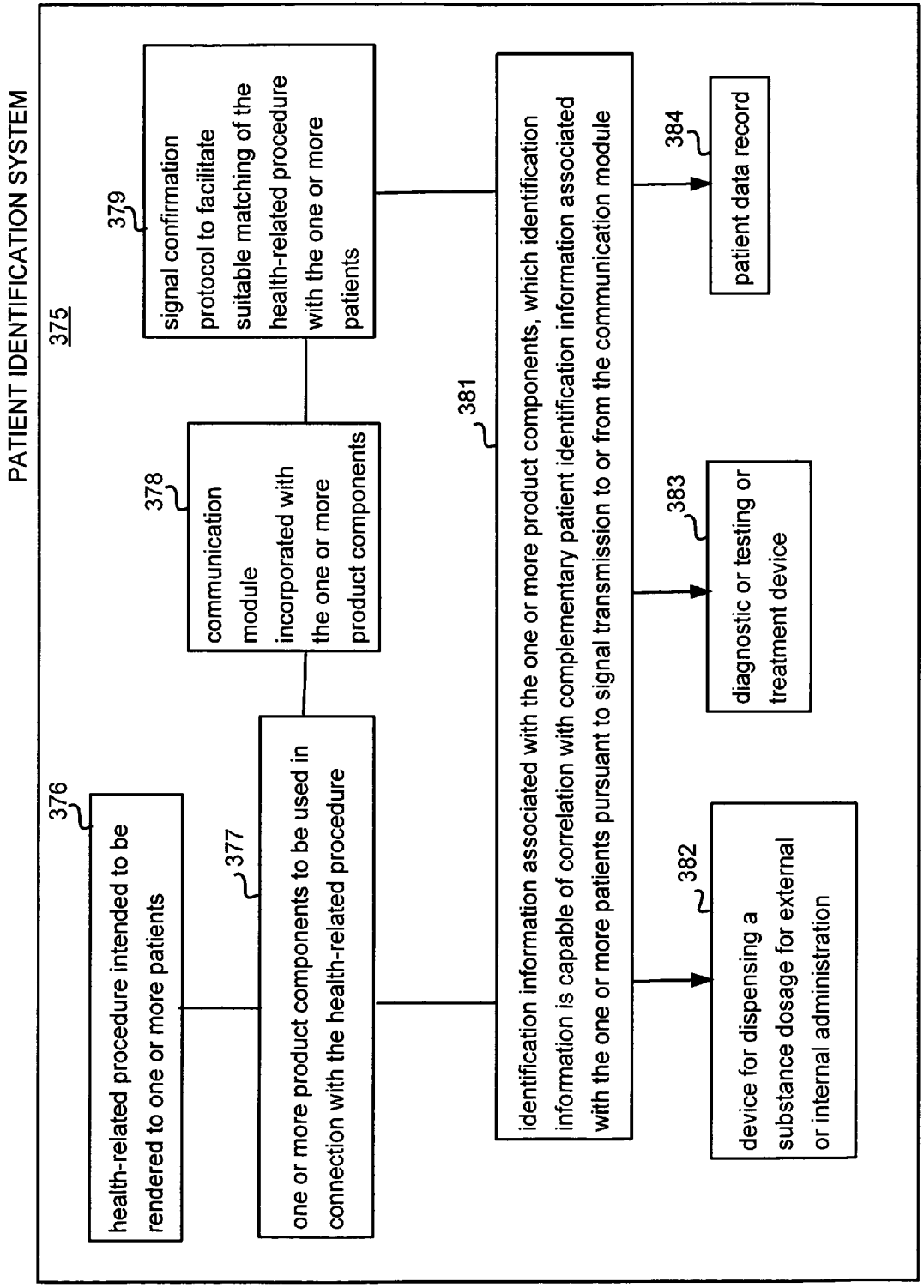

Referring to the schematic diagram of FIG. 17, an exemplary patient identification system embodiment 375 may include a health-related procedure that is intended to be rendered to one or more patients (block 376); one or more product components to be used in connection with the health-related procedure (block 377); a communication module incorporated with the one or more product components (block 378); a signal confirmation protocol to facilitate suitable matching of the health-related procedure with the one or more patients (block 379); and identification information associated with the one or more product components, which identification information is capable of correlation with complementary patient identification information associated with the one or more patients pursuant to signal transmission to or from the communication module (block 381).

It will be understood that additional system components such as a status indicator may be operably coupled with identification information to confirm compliance with a signal confirmation protocol for establishing suitable matching of a health-related procedure with one or more patients.

It will be further understood that a control module may be configured to either allow or prevent activation of a health-related procedure base on a determination of suitable matching of a health-related procedure with one or more patients.

Other possible system aspects may provide various product components associated with patient identification information. For example such product components may include a device for dispensing a substance dosage for external or internal administration to the particular patient (block 382), a diagnostic or testing or treatment device (block 383), and a patient data record (block 384).

Figure 18:
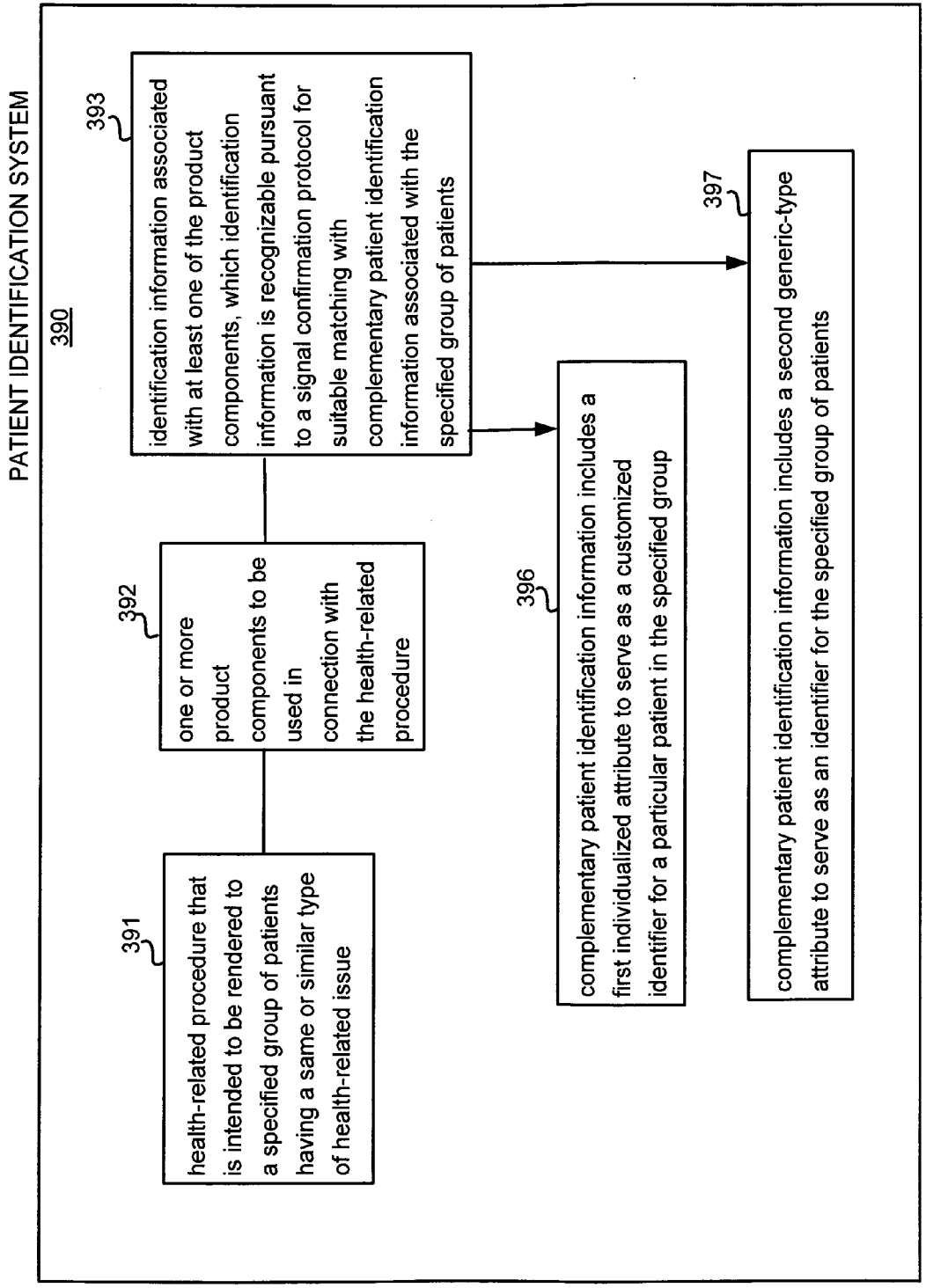

Referring to the schematic diagram of FIG. 18, an exemplary patient identification system embodiment 390 may include a health-related procedure that is intended to be rendered to a specified group of patients having a same or similar type of health-related issue (block 391); one or more product components to be used in connection with the health-related procedure (block 392); and identification information associated with at least one of the product components, which identification information is recognizable pursuant to a signal confirmation protocol for suitable matching with complementary patient identification information associated with the specified group of patients (block 393). It will be understood that such complementary patient identification may include an attribute to serve as an identifier for a diagnostic or testing or treatment procedure.

Additional possible system aspects may provide complementary patient identification information that includes a first individualized attribute to serve as a customized identifier for a particular patient in the specified group (block 396), and that may include a second generic-type attribute to serve as an identifier for the specified group of patients (block 397).

Figure 19:
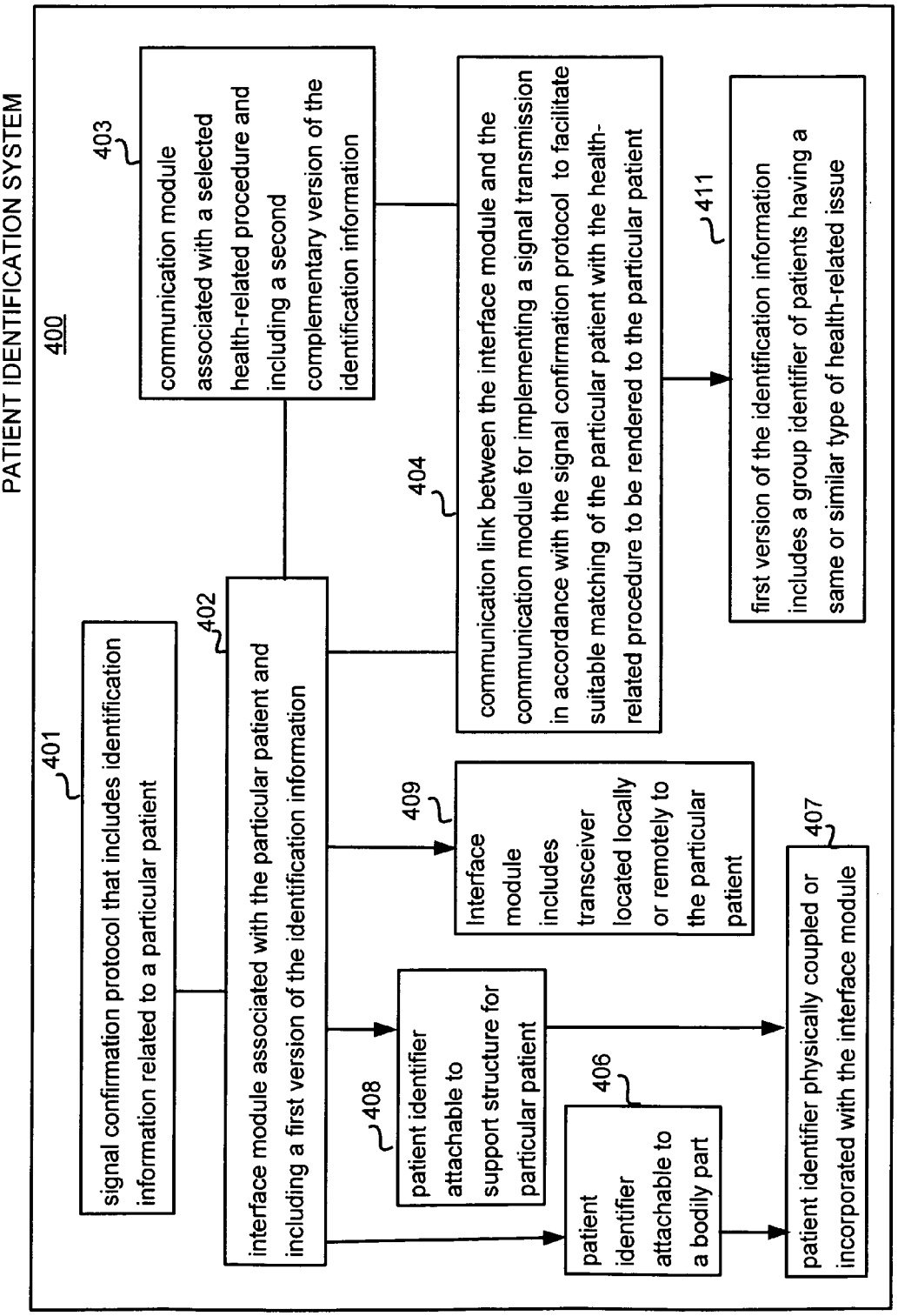

A further exemplary system embodiment 400 for patient identification shown in FIG. 19 provides a signal confirmation protocol that includes identification information related to a particular patient (block 401); an interface module associated with the particular patient and including a first version of the identification information (block 402); and a communication module associated with a selected health-related procedure and that includes a second complementary version of the identification information (block 403). An additional possible component includes a communication link between the interface module and the communication module for implementing a signal transmission in accordance with the signal confirmation protocol to facilitate suitable matching of the particular patient with the health-related procedure to be rendered to the particular patient (block 404).

Other possible implementation features may provide a first version of identification information that includes an individual identifier for a particular patient. A system implementation may include a computer program product having instructions encoded on storage or transmission media, which instructions implement a process for verification of correlation between the first version of the identification information associated with the particular patient and the second version of the identification information associated with a health-related procedure to be rendered to the particular patient.

Various types of additional system aspects that may be provided are shown in FIG. 19. For example, an exemplary system embodiment may provide patient identifier components that are physically coupled or incorporated with an interface module (block 407). A possible patient identifier may be attachable to a bodily part (block 406), and a possible patient identifier may be attachable to support structure for a particular patient (block 408).

Some system implementations may provide an interface module that includes a transceiver located locally (e.g., in proximity to the particular patient) or remotely to the particular patient (block 409). Another possible system implementation may provide a first version of the identification information that includes a group identifier of patients having a same or similar type of health-related issue (block 411).

Figure 20:
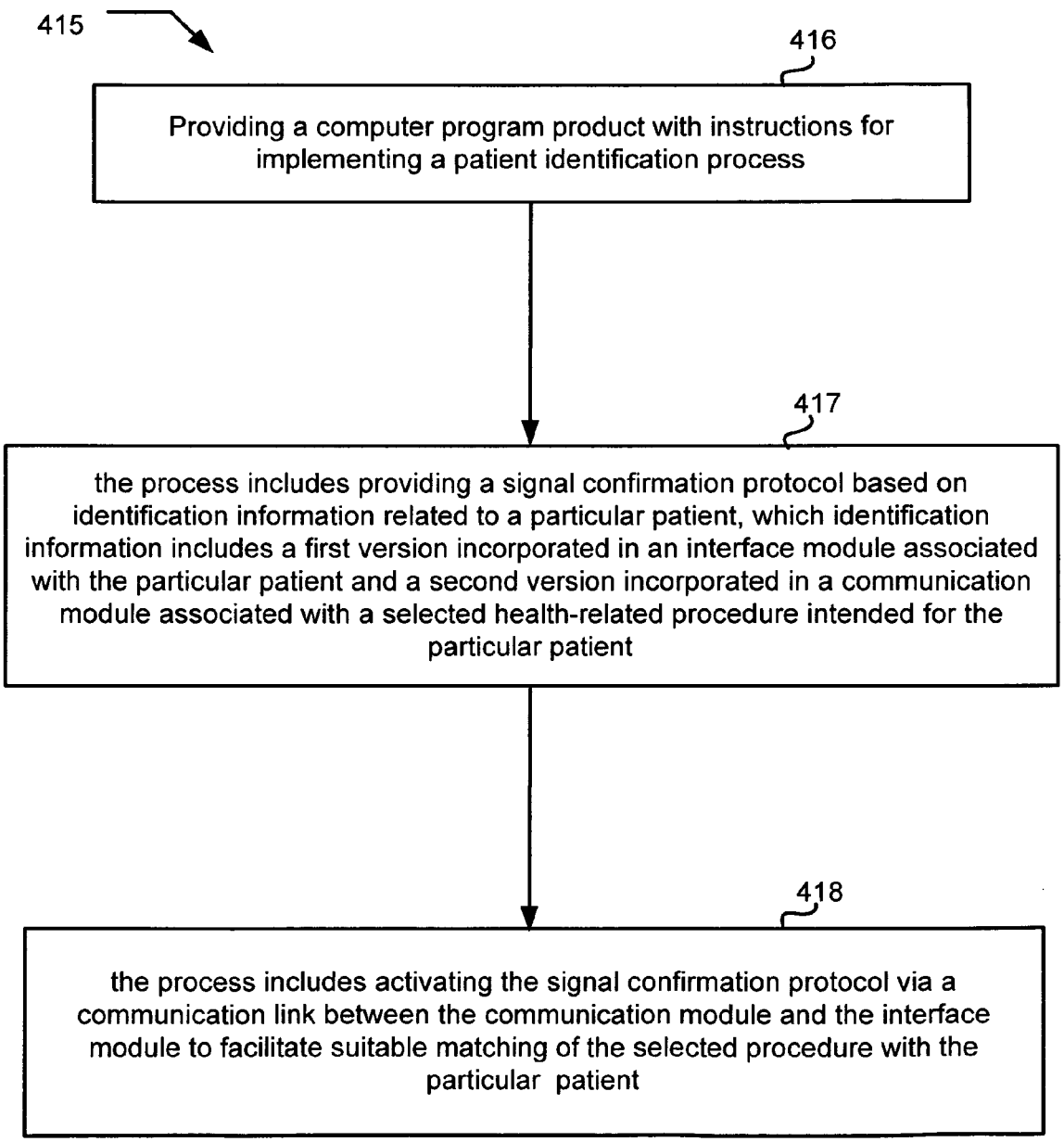
FIG. 20 shows an exemplary computer program product for encoding an exemplary process embodiment.

It will be understood that various process components may be incorporated in a computer program product 415 as shown in FIG. 20. For example, some embodiments may provide a computer program product having instructions for implementing a patient identification process (block 416), wherein the process may provide a signal confirmation protocol based on identification information related to a particular patient, which identification information includes a first version incorporated in an interface module associated with the particular patient and a second version incorporated in a communication module associated with a selected health-related procedure intended for the particular patient (block 417). The exemplary process may further activate the signal confirmation protocol via a communication link between the communication module and the interface module to facilitate suitable matching of the selected procedure with the particular patient (block 418).

Other exemplary computer program product features may be incorporated in a process embodiment that allowing activation of the selected health-related procedure in the event the signal confirmation protocol establishes satisfactory correlation between the first and second versions of the identification information. A related exemplary computer program product features may be incorporated in a process embodiment that prevents activation of the selected health-related procedure in the event the signal confirmation protocol fails to establish satisfactory correlation between the first and second versions of the identification information.

Figure 21:
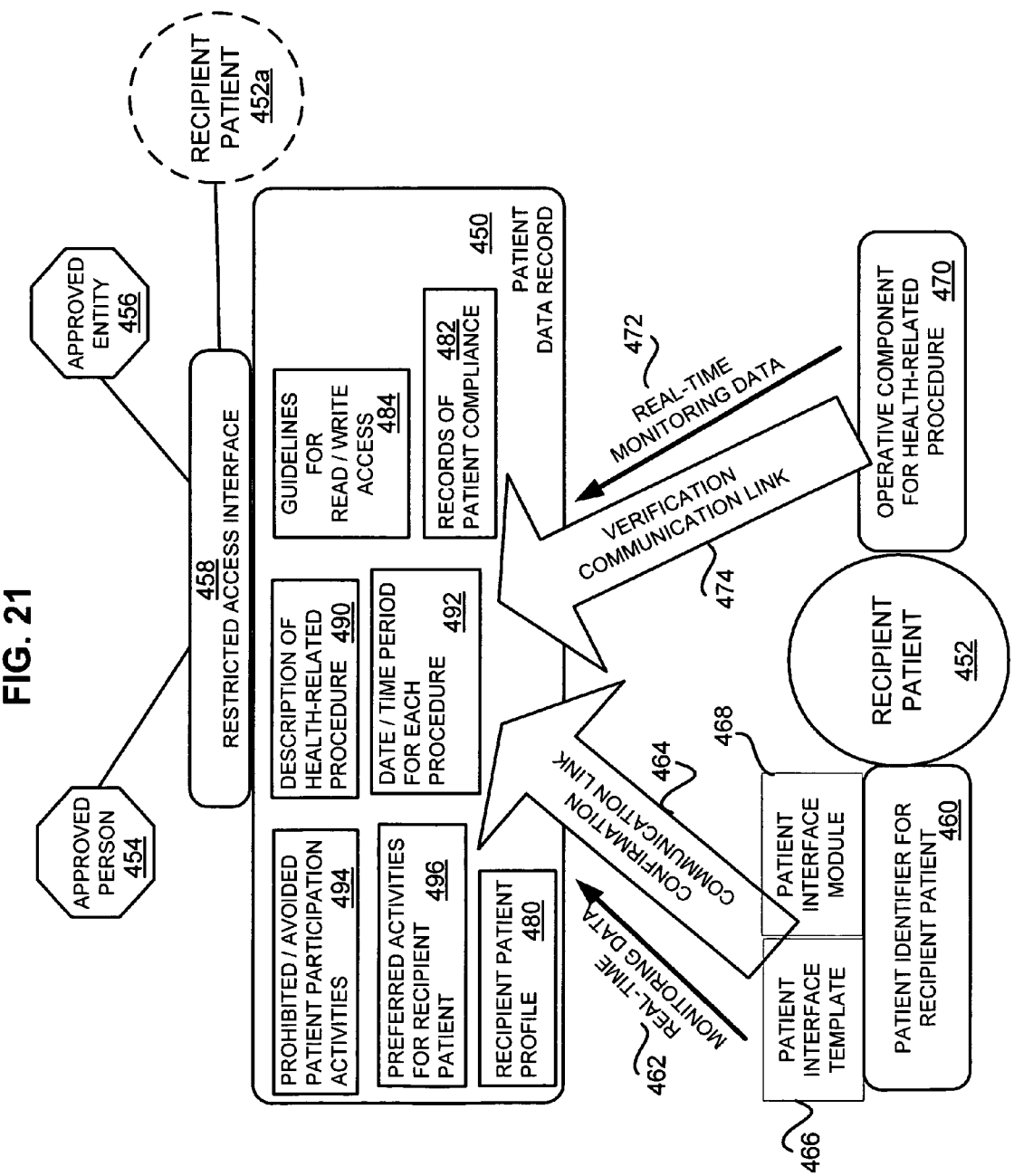
FIG. 21 is a schematic system diagram that illustrates various exemplary monitoring techniques for patient data maintenance.

Referring to the schematic diagram of FIG. 21, an exemplary embodiment illustrates features for maintaining a patient data record 750 associated with a recipient patient 452. The embodiment features may include a restricted access interface 458 to provide security for the various types of data maintained and updated in the patient data record 750. Approved read and/or write access may be granted in accordance with appropriate privacy guidelines, such as to an approved person 454, an approved entity 456, and directly or indirectly to the recipient patient 452a.

As further illustrated in FIG. 21, a recipient patient 452 may be scheduled for administration of a selected health-related procedure. Updated patient data regarding administration of the selected health-related procedure to the recipient patient 452 is obtained in real-time for transmission to the patient data record 750. Various techniques may be provided to assure a high level of data integrity.

Such updated data integrity regarding confirmation of the actual person targeted for the selected health-related procedure may be implemented by using a patient identifier 460 that is associated with the recipient patient 452 and communicated through a confirmation communication link 464 to the patient data record 750. The patient identifier 460 may be configured to be incorporated in a patient interface template 466 that is operationally coupled to the confirmation communication link 464. In some instances the patient identifier 460 may be configured to be incorporated in a patient interface module (e.g., as part of a signal protocol) that is operationally coupled to the confirmation communication link 464. It will be understood that transmitting real-time monitoring data 462 that includes a confirmation of the patient identifier 460 at or about the time of administering the health-related procedure to the recipient patient helps to assure a desirable level of data integrity for the patient data record 750.

Such updated data integrity regarding confirmation of the actual health-related procedure being administered to the targeted recipient patient 452 may be implemented by using an operative component 470 that is associated with the health-related procedure. In that regard, the operative component 470 may be coupled to a verification communication link 474 for transmitting real-time monitoring data 472 to the patient data record 450. It will be understood that transmitting such real-time monitoring data 472 that includes a verification of administration of the selected health-related procedure helps to further assure a desirable level of data integrity for the patient data record 750.

Exemplary records that may be incorporated in the patient data record 450 may include a recipient patient profile 480, records of patient compliance 482, and guidelines for read and/or write access 484 to the patient data record 450. Additional exemplary records may further include a description of one or more selected health-related procedures 490, and date/time period for each procedure 492 involving the recipient patient 452.

Additional exemplary records may include prohibited and/or avoided patient participation activities 494 and preferred activities for recipient patient 496.

It will be understood that the particular records shown are for purposes of illustration only, and other types of records may in some circumstances be desirable. Of course some categories of records may not be deemed necessary for certain recipient patents.

Figure 22:
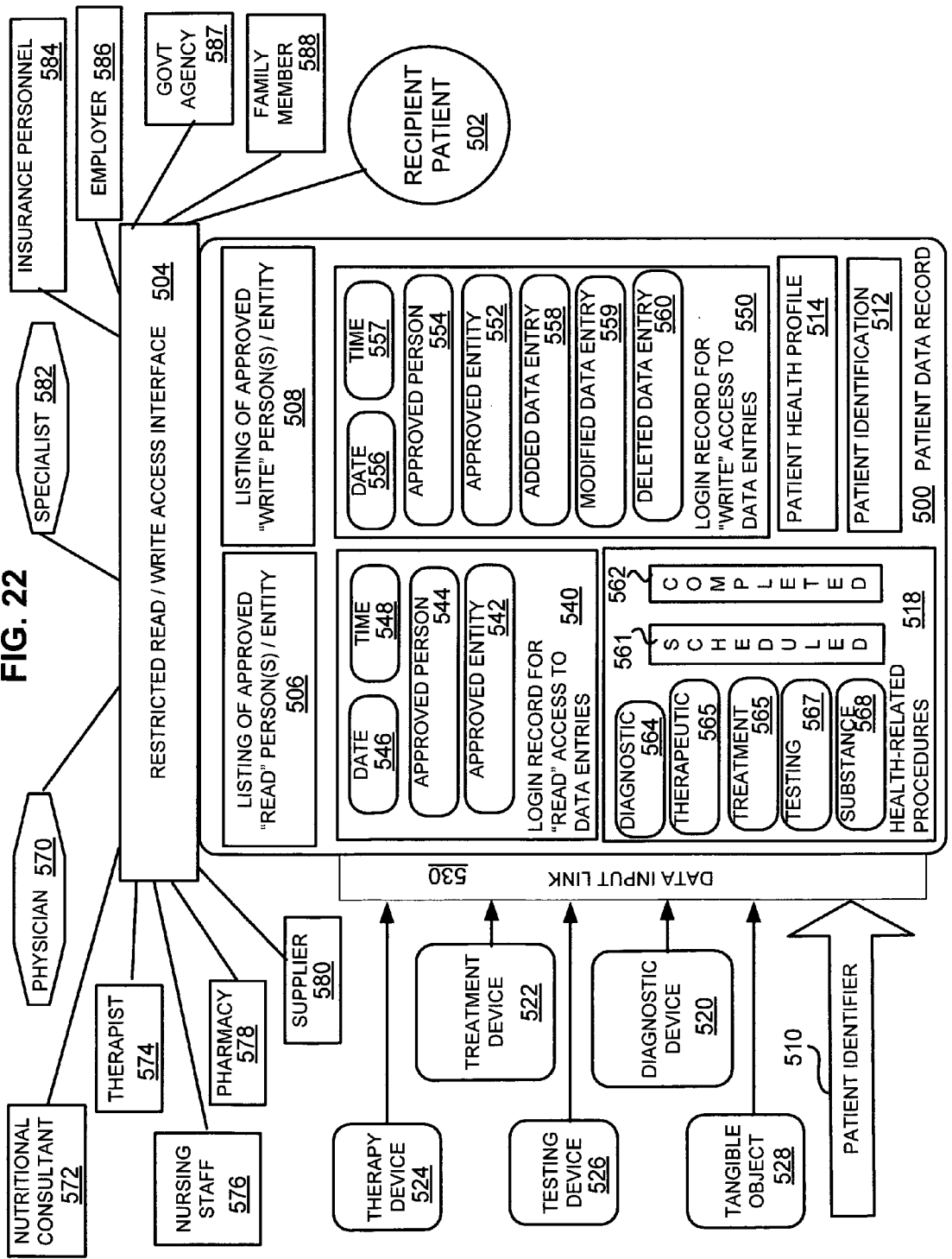
FIG. 22 is a schematic block diagram of further exemplary embodiment features that may be implemented.

Referring to the schematic block diagram of FIG. 22, an exemplary embodiment for maintenance of a patient data record 500 having a restricted read/write access interface 504 is illustrated for a recipient patient 502. Basic types of records to correlate and update ongoing patient activities may include a patient identification 512, a patient health profile 514, and a listing of selected health-related procedures 518 involving the recipient patient 502.

A data input link 530 to the patient data record 500 is configured to receive real-time monitoring data including a patient identifier 510 that is associated with the targeted recipient patient 502. Additional real-time monitoring data regarding a selected health-related procedure may be received via the data input link 530 to provide verification associated with a diagnostic device 520, treatment device 522, therapy device 524, testing device 526 and tangible object 528.

It will be understood that preliminary data for selected health-related procedures that are scheduled 561 may be maintained in the patient data record 500. Additional updated data for such health-related procedures that are completed 562 may also be maintained in the patient data record 500. Appropriate overall monitored activities for a particular recipient patient 502 may involve maintaining exemplary records for activities that include diagnostic 564, therapeutic 565, and testing 567 procedures as well as exemplary records for one or more substances 568 to be monitored.

The patient record 500 may include a listing of approved "read" persons and/or entities 506. Exemplary related records that are to be maintained and updated may include a login record for "read" access to data entries 540 that keeps track of each access by an approved entity 542 or by an approved person 544 along with the date 546 and time 548 for each "read" access.

Another possible category of records may include a listing of approved "write" persons and/or entities 508. Exemplary related records that are to be maintained and updated may include a login record for "write" access to data entries 500 that keeps track of each access by an approved entity 552 or by and approved person 554 along with the date 556 and time 557 for each "write" access, as well as tracking data identifying and indicating what occurred: an added data entry 558, a modified data entry 559, a deleted data entry 560.

Some exemplary embodiments may provide approved "read" and/or "write" access to the patient data record 500 for many different types of persons and/or entities. Such an approved access may in some instances be given to a physician 570, nutritional consultant 572, therapist 574, nursing staff 576, pharmacy 578, supplier 580, and specialist 582. In some embodiments an approval for access to the patient data record 500 may be given to insurance personnel 584, employer 586, government agency 587 and family member 588.

Figure 23:
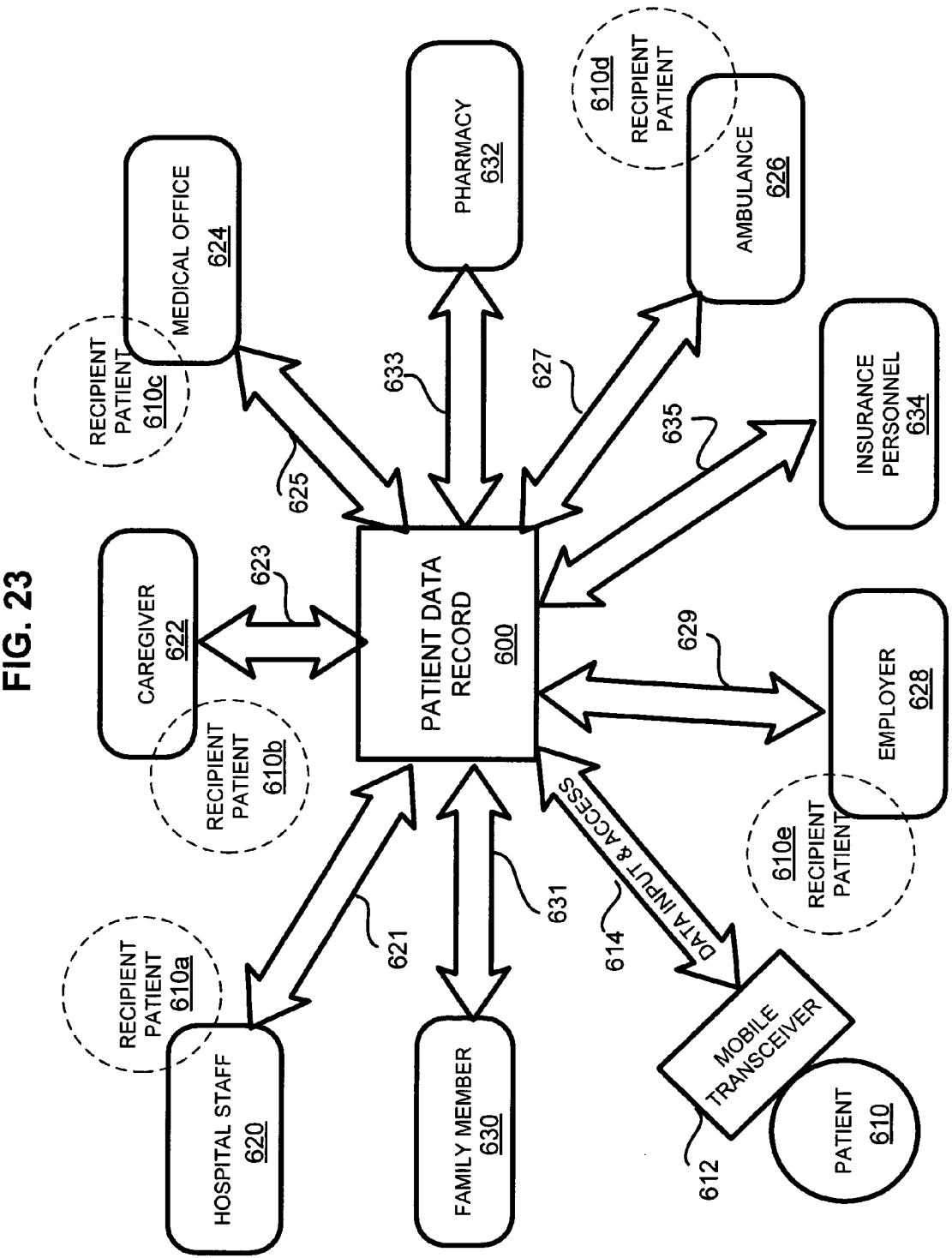
FIGS. 23-25 are schematic representations of possible communication links that may be used in patient data maintenance embodiments.

The schematic representation of FIG. 23 illustrates an exemplary patient data record 600 associated with patient 610 having a mobile transceiver 612 that enables bidirectional data input and access (e.g., "read" access and/or "write" access) through communication link 614 to the patient data record 600. Other approved persons or entities may also have such data input and access to the patient data record 600. Some of the illustrated examples include hospital staff 620 through communication link 621, caregiver 622 through communication link 622, medical office 624 through communication link 625, ambulance 626 through communication link 626, and employer 628 through communication link 629.

In some instances the patient 610 may be a participant in a selected health-related procedure that involves the approved person or entity at a particular situs or locale. For example, the hospital staff 620 may be providing tests or treatment to recipient patient 610a, the caregiver 622 may be supervising a medication dosage or diet regimen for recipient patient 610b, and the medical office 624 may be performing a diagnostic examination on recipient patient 610c. In other circumstances an ambulance 626 may be transporting recipient patient 610d to an emergency care facility, and recipient patient 610e may be doing restricted work activities at employer 628. It will be understood that periodic real-time monitoring data (e.g., patient identity confirmation, selected procedure verification) transferred to the patient data record 450 may be initiated from the particular situs or locale by the recipient patient or by the approved person/entity or by an object or component involved in the selected health-related procedure.

Other illustrated examples of an approved person or entity having data input and access to the patient data record 600 may include a family member 630 through communication link 631, pharmacy 632 through communication link 633, and insurance personnel 634 through communication link 635. Although the patient 610 may not be at the particular situs or locale of the approved person or entity, some embodiment implementations may nevertheless provide periodic real-time monitoring data transferred to the patient data record from the particular situs or locale by the approved person/entity or by an object or component involved in the selected health-related procedure.

It will be understood that the transmission of real-time monitoring data may occur automatically as part of a selected health-related procedure (e.g., patient release processed by computerized system of hospital staff 620, patient use of C-PAP machine during nighttime sleeping) or may be user-activated at or about the time of administration of a selected health-related procedure (e.g., coverage authorization by insurance personnel 634, filling a prescription by pharmacy 632).

It will be further understood that the various communication links (614, 621, 623, 625, 627, 629, 631, 633, 635) may be implemented with a network connection, a wireless transmission, a dedicated line, etc. as deemed to be appropriate based on the condition of the patient, the technical capability of the approved person/entity, and the type of object or component used in connection with administration of the selected health-related procedure.

Figure 24:
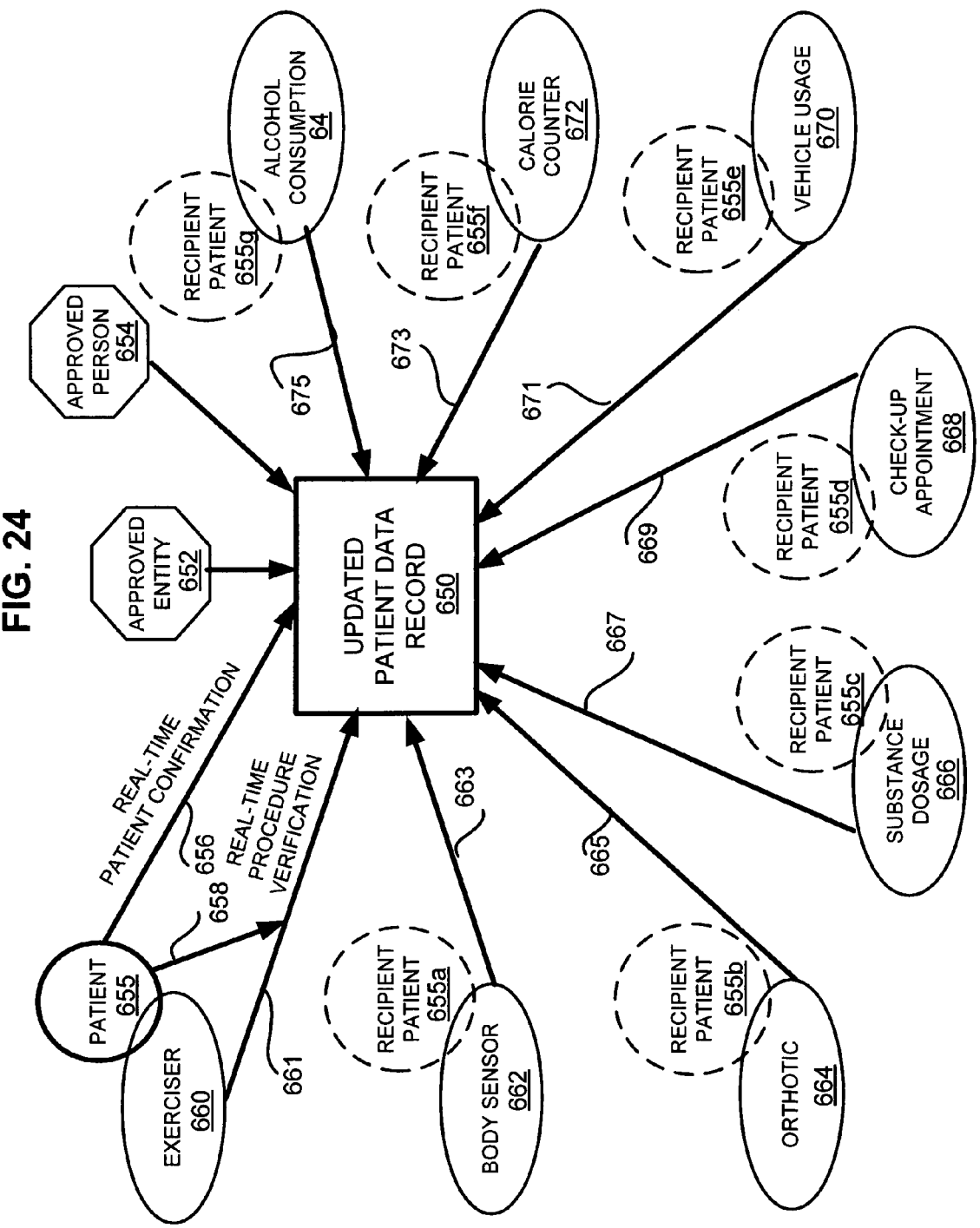

Referring to the schematic representation of an exemplary embodiment shown in FIG. 24, a patient 655 is associated with an updated patient data record 650 that may receive real-time monitoring data from an approved entity 652 and from an approved person 654. Another illustrated example shows a health-related procedure involving use by patient 655 of a device such as exerciser 660. A real-time patient confirmation 656 may be initiated from the patient 655 to the updated patient data record 650, and real-time procedure verification 658 of actual use of the exerciser 660 procedure may also be initiated by the patient 655. In some circumstances real-time procedure verification 661 may come directly from an operative component of the exerciser 660.

Other illustrated examples of inputs provided to the updated patient data record 650 include real-time monitoring data 663 from a body sensor 662 of recipient patient 655a, real-time monitoring data 665 from an orthotic 664 worn by recipient patient 655b, and real-time monitoring data 667 for a substance dosage 666 given to recipient patient 655c. Further illustrated examples of inputs provided to the updated patient data record 650 include real-time monitoring data for attendance by recipient patient 655d at check-up appointment 668, real-time monitoring data for vehicle usage 670 by recipient patient 655e, real-time monitoring data from calorie counter 672 that keeps track of dietary intake by recipient patient 655f, and real-time monitoring data for alcohol consumption 674 of recipient patient 655g.

Figure 25:
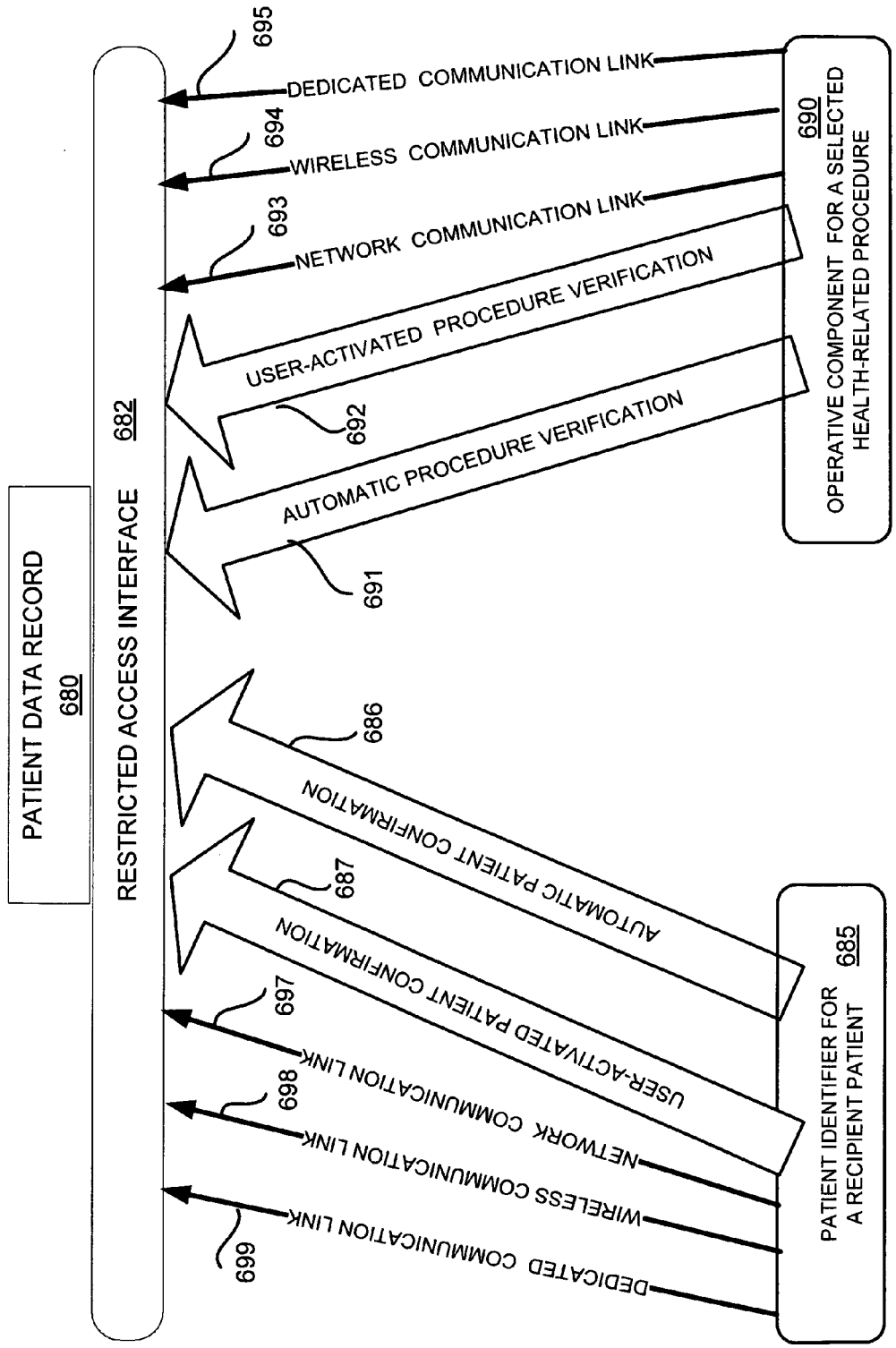

FIG. 25 schematically illustrates different possible embodiment features for obtaining real-time monitoring data provided to an exemplary patient data record 680 having a restricted access interface 682 (e.g., preventing unauthorized "read" access or unauthorized "write" access). Such monitoring data that includes real-time confirmation of a patient identifier for a recipient patient 685 may be transmitted to the patient data record 680 through a network communication link 697, a wireless communication link 698, or a dedicated communication link 699. It will be understood that real-time confirmation of the patient identifier may be a transmission that includes a user-activated patient confirmation 687 or an automatic patient confirmation 686.

Such monitoring data that includes real-time verification of an actual administration procedure may be initiated by an operative component for a selected health-related procedure 690. The monitoring data that provides real-time verification of the actual administration procedure may be transmitted to the patient data record 680 through a network communication link 693, a wireless communication link 694, or a dedicated communication link 695. It will be understood that real-time verification of the actual administration procedure may be a transmission that includes user-activated procedure verification 692 or an automatic procedure verification 691.

Although separate communication links are shown for purposes of illustration, transmission of real-time monitoring data may be accomplished by a combination of different types of communication channels and communication media. For example, a shared communication link may in some instances be used for both types of real-time monitoring data (e.g., patient identifier & procedure verification) depending on the circumstances.

Figure 26:
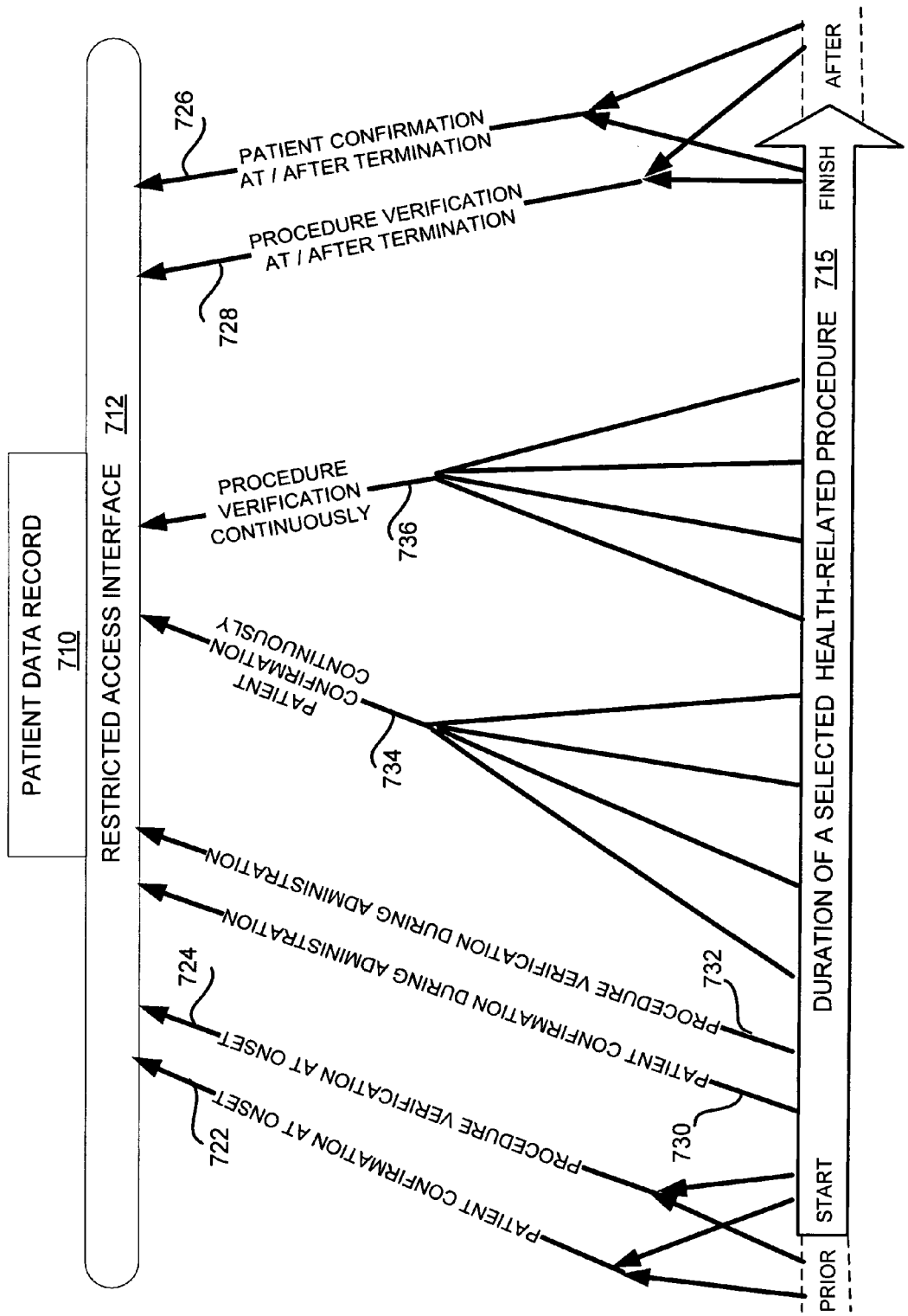
FIG. 26 is a further schematic representation that illustrates exemplary techniques that may be implemented in connection with monitoring a health-related procedure.

Referring to the schematic representation of FIG. 26, different exemplary time period possibilities are illustrated for providing real-time monitoring data to a patient data record 710 having a restricted access interface 712. For example, duration of a selected health-related procedure may extend from a start to a finish. Some embodiments may provide a transmission that includes patient confirmation at onset 722 (e.g., prior to starting, at start, or shortly after starting), and may further include procedure verification at onset 724 (e.g., prior to starting, at start, or shortly after starting). Other embodiments may provide a transmission that includes patient confirmation during administration 730 of the selected health-related procedure, and may further include procedure verification during administration 732. In some implementations a transmission may include patient confirmation at or soon after termination 726 of the selected health-related procedure, and may further include procedure verification at or soon after termination 728.

It will be understood that various timing combinations may be chosen depending on the circumstances, and the illustrated timing examples are not intended to be limiting. For example, some embodiments may provide patient confirmation continuously 734 during the duration of a selected health-related procedure 715. Some embodiments may further provide procedure verification continuously 736 during the duration of a selected health-related procedure 715.

It will be appreciated from the exemplary embodiments disclosed herein that a patient data maintenance system may include a data input link capable of receiving updated information based on real-time monitoring data regarding administration of a selected health-related procedure to the recipient patient, wherein the real-time monitoring data includes a patient identifier for the recipient patient. An additional possible system feature may include one or more data entries in the patient data record indicating verification of a health-related procedure scheduled or completed for the recipient patient.

Further possible system features may provide a data entry that includes verification of one of more of the following types of health-related procedure scheduled or completed by the recipient patient: diagnosis, test, treatment, malady, ailment, surgical procedure, anesthetic, medication, diet, therapy, and nutritional regimen.

Some system embodiments may include one or more of the following types of output access (e.g., "read" access) to the patient data record: hardcopy view, hardcopy printout, display monitor, remote access, text access, audio access, image access, fax access, hyperlinked access, and cross-reference link.

Additional system embodiments may include one of more of the following type of input access ("write" access) to the patient data record: handwritten, keyboarded, scanned, oral, faxed, remote transmittal, wireless transmittal, data modification, data deletion, hyperlinked data entry, and cross-reference link.

In some instances a system embodiment may include a set of guidelines regarding restricted read and/or write access to the patient data record. Other possible records included in the patient data record may include a logon record for "read" access to the patient data record, and may further include a logon record for "write" access to the patient data record.

It will be further understood that a data maintenance system embodiment may further include a computer program product with instructions encoded on storage or transmission media, which instructions implement a process for confirmation of the patient identifier included with real-time monitoring data received by the patient data record. In some instances a data maintenance system embodiment may further include a computer program product with instructions encoded on storage or transmission media, which instructions implement a process for processing the real-time monitoring data that includes a verification of completion of the health-related procedure for the recipient patient.

Figure 27:
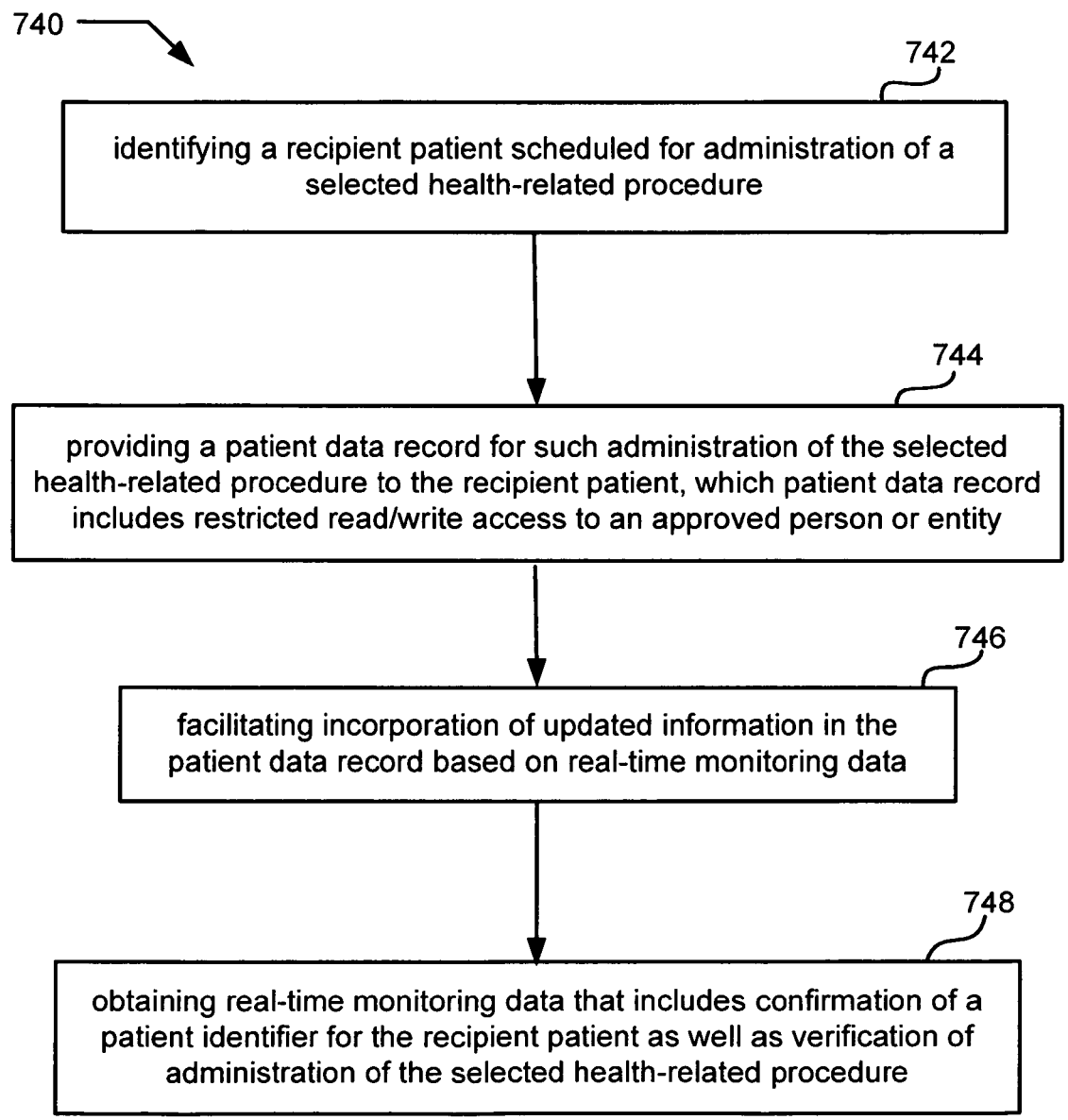
FIG. 27 is a high level flow chart for a further exemplary process embodiment.

Referring to the exemplary embodiment 740 illustrated in the flow chart of FIG. 27, a patient data maintenance process may include identifying a recipient patient scheduled for administration of a selected health-related procedure (block 742); providing a patient data record for such administration of the selected health-related procedure to the recipient patient, which patient data record includes restricted read and/or write access to an approved person or entity (block 744); and facilitating incorporation of updated information in the patient data record based on real-time monitoring data (block 746). Further possible process features may include obtaining real-time monitoring data that includes confirmation of a patient identifier for the recipient patient as well as verification of administration of the selected health-related procedure (block 748).

Figure 28:
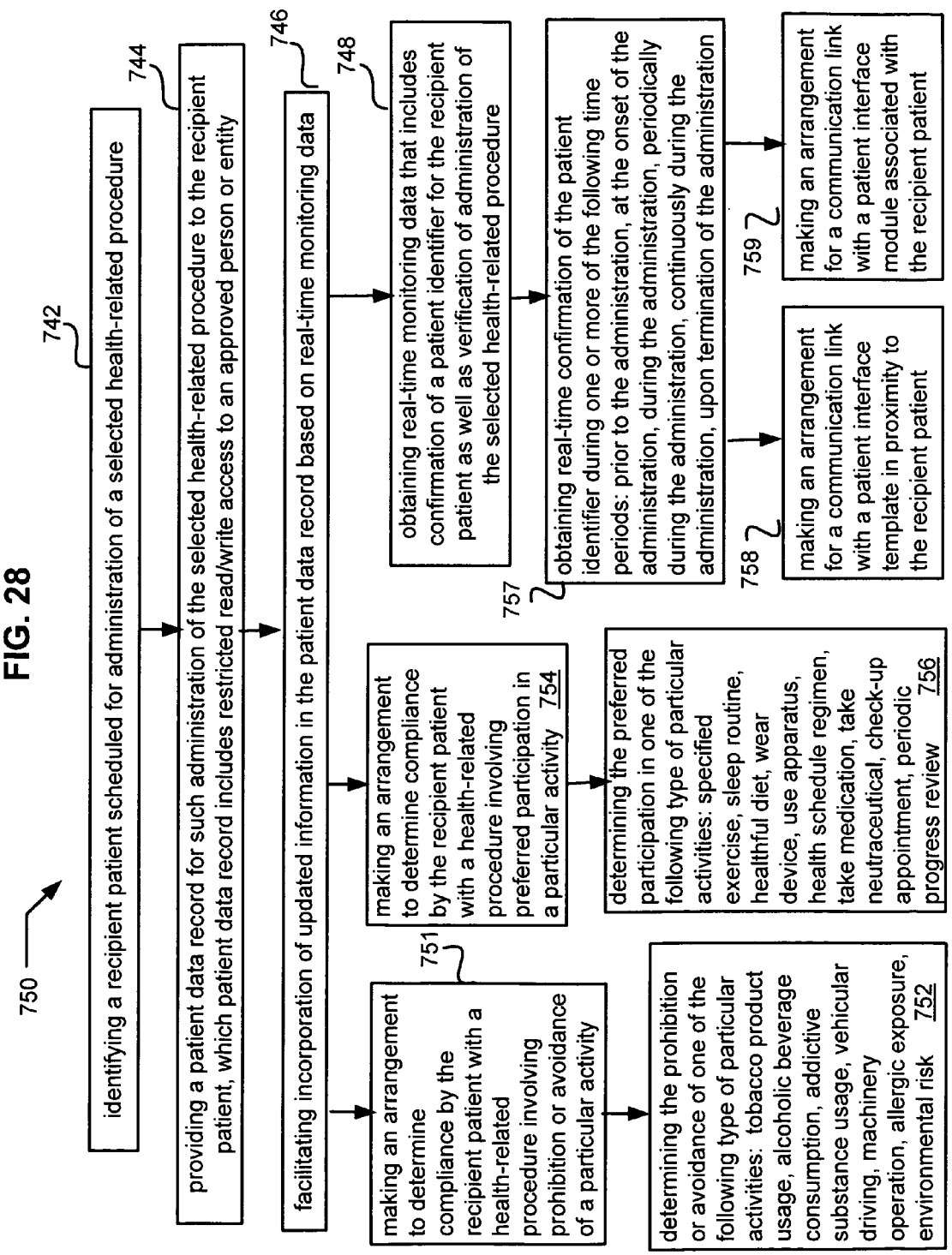
FIGS. 28-31 are flow charts showing additional detailed aspects of exemplary process embodiments.

Additional exemplary process embodiment implementations 750 are depicted in FIG. 28, including previously described features 742, 744, 746, 748 along with making an arrangement to determine compliance by the recipient patient with a health-related procedure involving prohibition or avoidance of a particular activity (block 750). A related operation may include determining the prohibition or avoidance of one of the following type of particular activities: tobacco product usage, alcoholic beverage consumption, addictive substance usage, vehicular driving, machinery operation, allergic exposure, environmental risk (block 752).

Other exemplary implementation features may include making an arrangement to determine compliance by the recipient patient with a health-related procedure involving preferred participation in a particular activity (block 754). A related operation may include determining the preferred participation in one of the following type of particular activities: specified exercise, sleep routine, healthful diet, wear device, use apparatus, health schedule regimen, take medication, take neutraceutical, check-up appointment, periodic progress review (block 756).

Additional possible embodiment operations shown in FIG. 28 include obtaining real-time confirmation of the patient identifier during one or more of the following time periods: prior to the administration, at the onset of the administration, during the administration, periodically during the administration, continuously during the administration, and upon termination of the administration (block 757). Further process features for patient data maintenance may include making an arrangement for a communication link with a patient interface template in proximity to the recipient patient (block 758), and making an arrangement for a communication link with a patient interface module associated with the recipient patient (block 759).

Figure 29:
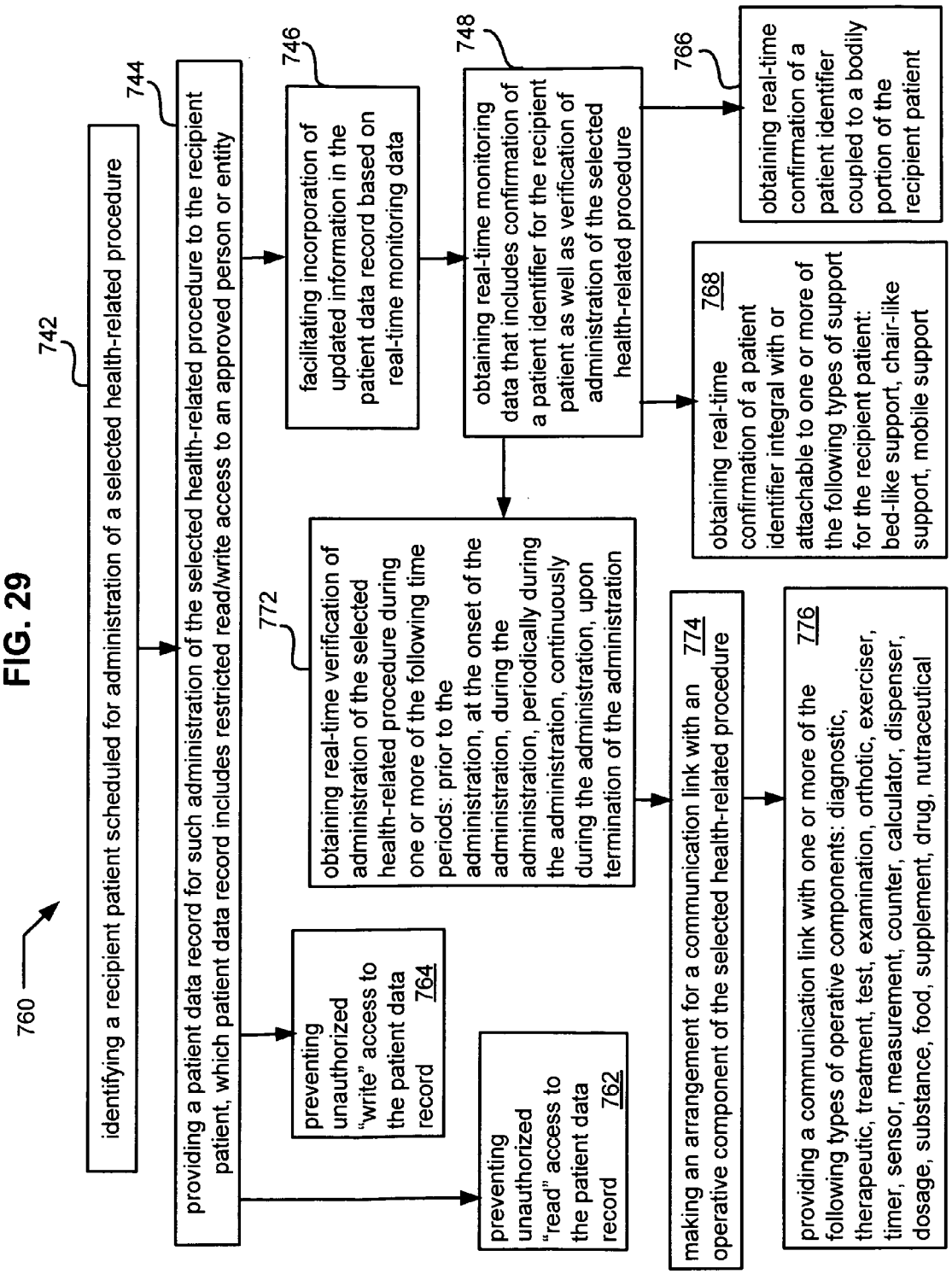

The flow chart embodiments 760 of FIG. 29 include previously described process operations 742, 744, 746, 748 in combination with obtaining real-time confirmation of a patient identifier coupled to a bodily portion of the recipient patient (block 766). Other possible process features may include obtaining real-time confirmation of a patient identifier integral with or attachable to one or more of the following types of support for the recipient patient: bed-like support, chair-like support, mobile support (block 768). Additional implementation operations may include preventing unauthorized "read" access to the patient data record (block 762) and/or preventing unauthorized "write" access to the patient data record (block 764).

Other exemplary process features may include obtaining real-time verification of administration of the selected health-related procedure during one or more of the following time periods: prior to the administration, at the onset of the administration, during the administration, periodically during the administration, continuously during the administration, and upon termination of the administration (block 772). A further possible operation may include making an arrangement for a communication link with an operative component of the selected health-related procedure (block 774). Additional possible operation features may include providing a communication link with one or more of the following types of operative components: diagnostic, therapeutic, treatment, test, examination, orthotic, exerciser, timer, sensor, measurement, counter, calculator, dispenser, dosage, substance, food, supplement, drug, nutraceutical (block 776).

Figure 30:
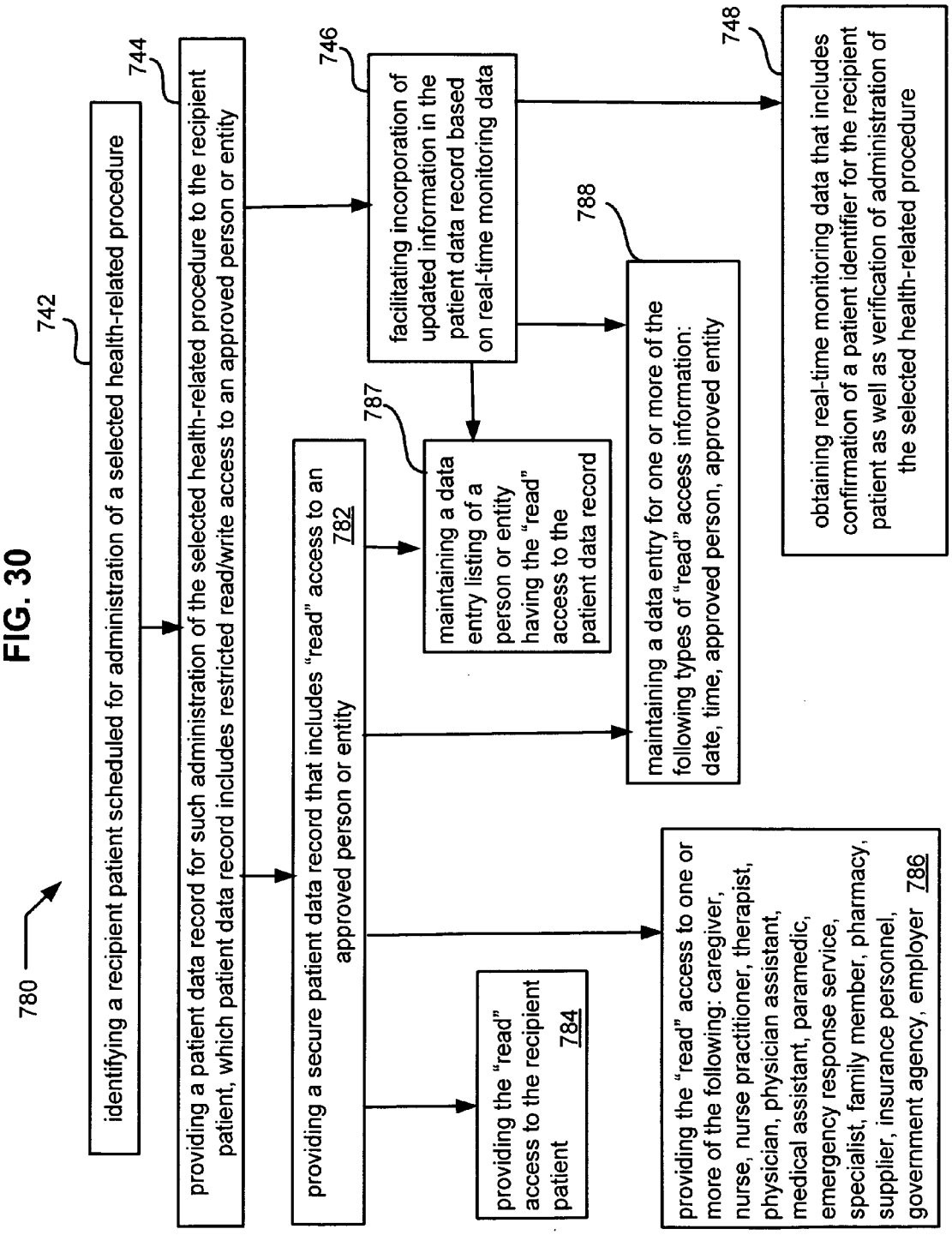

The detailed flow chart of FIG. 30 illustrates previously described process operations 742, 744, 746, 748 as well as providing a secure patient data record that includes "read" access to an approved person or entity (block 782). A further possible operation may include providing "read" access to the recipient patient (block 784). Other possible process features may include providing the "read" access to one or more of the following: caregiver, nurse, nurse practitioner, therapist, physician, physician assistant, medical assistant, paramedic, emergency response service, specialist, family member, pharmacy, supplier, insurance personnel, government agency, employer (block 786).

Further exemplary implementation features may include maintaining a data entry listing of a person or entity having the "read" access to the patient data record (block 787), and maintaining a data entry for one or more of the following types of "read" access information: date, time, approved person, and approved entity (block 748).

Figure 31:
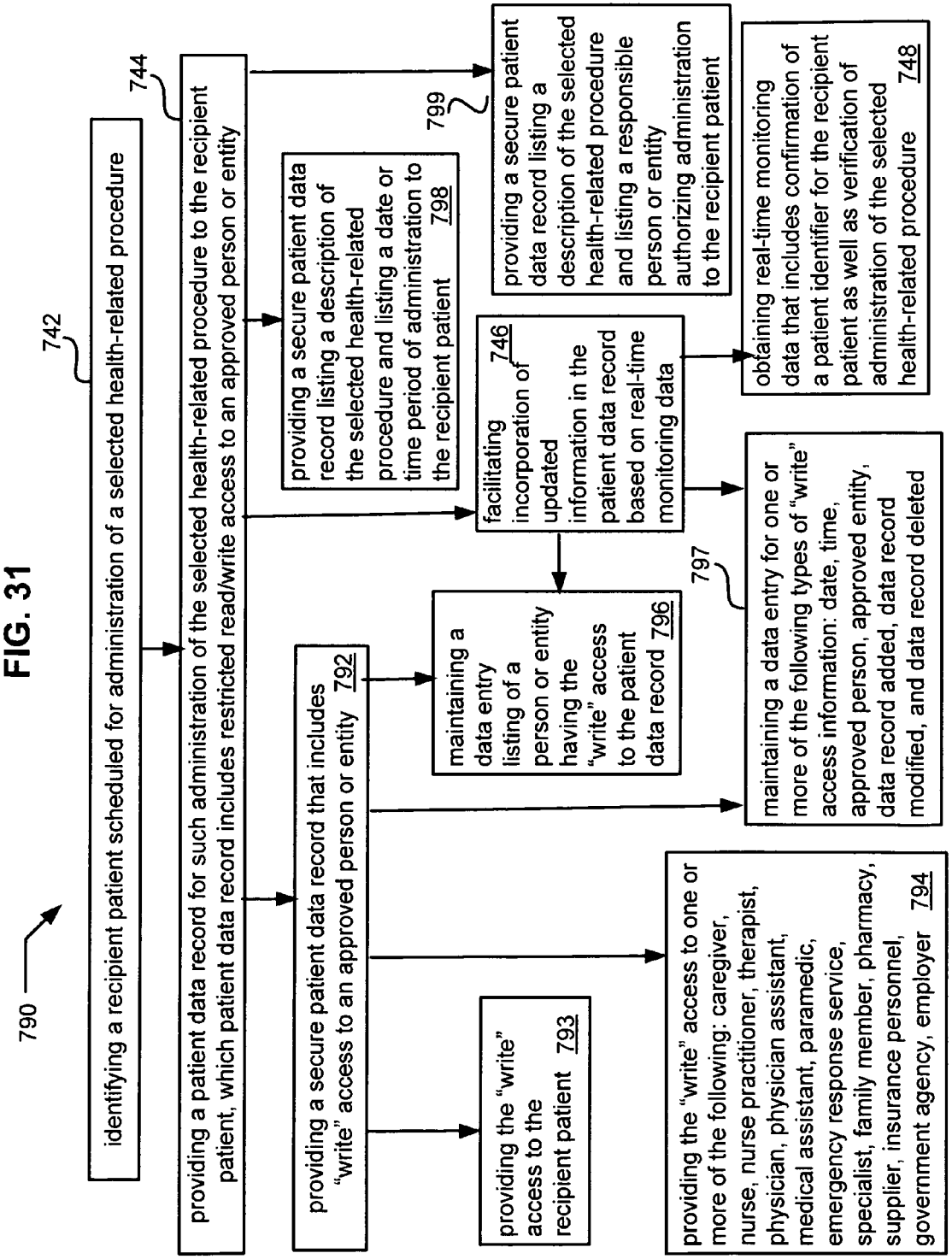

Referring to the embodiment features 790 illustrated in the flow chart of FIG. 31, previously described operations 742, 744, 746, 768 are depicted in combination with other exemplary operations such as providing a secure patient data record that includes "write" access to an approved person or entity (block 792), and providing "write" access to the recipient patient (block 793). Other possible process features may include providing the "write" access to one or more of the following: caregiver, nurse, nurse practitioner, therapist, physician, physician assistant, medical assistant, paramedic, emergency response service, specialist, family member, pharmacy, supplier, insurance personnel, government agency, employer (block 794).

Additional operations may include maintaining a data entry listing of a person or entity having the "write" access to the patient data record (block 796), and maintaining a data entry for one or more of the following types of "write" access information: date, time, approved person, approved entity, data record added, data record modified, and a data record deleted (block 797).

Further exemplary process features depicted in FIG. 31 include providing a secure patient data record listing a description of the selected health-related procedure and listing a date or time period of administration to the recipient patient (block 798). Other possible process features may include providing a secure patient data record listing a description of the selected health-related procedure and listing a responsible person or entity authorizing administration to the recipient patient (block 799).

As disclosed herein, various exemplary process components for maintaining an updated patient data record may be incorporated in a computer program product wherein process instructions are encoded on media. An exemplary programmed process for maintaining an updated patient data record may include identifying a recipient patient scheduled for administration of a selected health-related procedure;

maintaining a patient data record for such administration of the selected health-related procedure to the recipient patient, which patient data record includes restricted read/write access to an approved person or entity; and processing and storing real-time monitoring data that includes confirmation of a patient identifier for the recipient patient as well as verification of administration of the selected health-related procedure.

Figure 32:
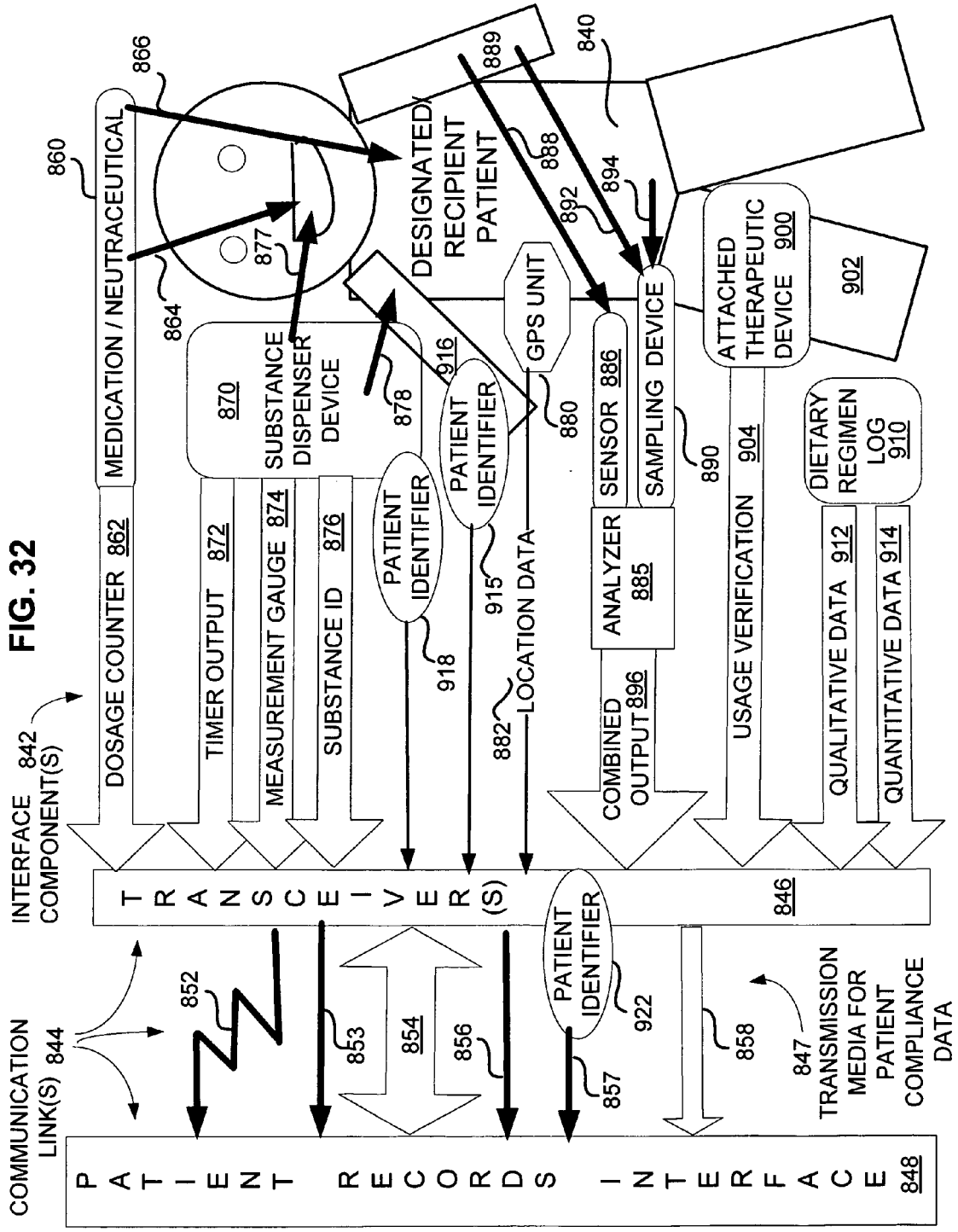
FIG. 32 is a schematic block diagram for various embodiment features that may be implemented regarding compliance data for health-related procedures.

The schematic block diagram of FIG. 32 depicts various exemplary embodiment features regarding compliance data for health-related procedures involving a designated/recipient patient 840. Such compliance data may be provided by one or more interface components 842 that are operably coupled to devices configured to collect real-time patient monitoring data. In order to create and maintain a cumulative summary of the real-time patient monitoring data for processing and accessibility, an exemplary system may include communication links 844 such as transceivers 846, transmission media 847 and patient records interface 848.

For purposes of illustration, FIG. 32 shows various types of exemplary transmission media 847 including wireless communication channel 852, network connection 853, bi-directional shared broadband connection 854, dedicated cable connector 856, and dedicated narrowband channel 858. In some instances the specific transmission media may carry a data stream that includes both a patient identifier (e.g., 915, 918) associated with the designated/recipient patient 840 as well as monitoring data for a particular health-related procedure administered to that patient 840 associated with the patient identifier. Other implementations may include a patient identifier 922 generated by transceiver 846 to be transmitted separately over transmission media 847. Whatever system embodiment is chosen will preferably include sufficient monitoring data to provide a confirmation that correlates the designated/recipient patient 840 with the health-related procedure being administered to such designated/recipient patient 840.

An exemplary health-related procedure shown in FIG. 32 may include administration of a medication and/or neutraceutical 860 wherein a dosage counter 862 generates updated compliance monitoring data based on inhalation or ingestion 864 of a dosage. In some instances such updated compliance monitoring data may be based on external application 866 of a dosage of the medication and/or neutraceutical 860 to a skin portion.

Another exemplary health-related procedure may involve a substance dispenser device 870 wherein updated compliance monitoring data is provided by timer output 872, by measurement gauge 874, and by substance identification 876 based on delivery 877 of a substance to a body orifice via a body fluid (e.g., saliva, inhaled air). In some instances such updated compliance monitoring data may be based on delivery 878 of a substance to a targeted body portion (e.g., arm) or via a body fluid (e.g., blood). The patient identifier 918 associated with substance dispenser device 870 may be separately provided to establish correlation with the monitoring data generated by the interface components 872, 874, 876.

A further exemplary health-related procedure may involve a global positioning device (GPS) unit 880 wherein patient location data is generated based on attachment of the GPS unit 880 to a body portion of such designated/recipient patient 840.

Yet another exemplary health-related procedure may include sensor 886 that obtains patient monitoring data (e.g., blood pressure) 888 from a body portion (e.g., arm), and a sampling device 890 that obtains a blood sample 892 from a patient's blood vessel. The sampling device 890 may also include capability for obtaining another body fluid sample (e.g., urine) 894 from the designated/recipient patient 840. The health-related procedure may also include analyzer 880 coupled to sensor 886 and sampling device 890 in order to generate updated compliance monitoring data such as combined output data 896.

Another possible health-related procedure may include an attached therapeutic device 900 such as a knee brace which is configured to generate updated compliance monitoring data such as usage verification 904.

An additional exemplary health-related procedure may include dietary regimen log 910 wherein a data entry input by the designated/recipient patient 840 and/or by a caregiver (not shown) may include updated qualitative data 912 (e.g., food description, beverage ingredients) as well as updated quantitative data 914 (e.g., serving size, calorie amount).

It will be understood that in some instances a patient identifier 916 may be separately generated from an interface component 842 such as a bracelet or the like attached to a body portion (e.g., arm) 916. However in some instances a patient identifier may be integrated as part of the updated monitoring data collected by one or more procedure interface components 842.

A variety of exemplary embodiments of software/hardware types of monitoring devices may be implemented or configured as a separate component and/or as an integrated element associated with the particular health-related procedure, wherein some embodiments may provide for the updated monitoring data to be based on automatic procedure verification and/or based on user-activated procedure verification.

Figure 33:
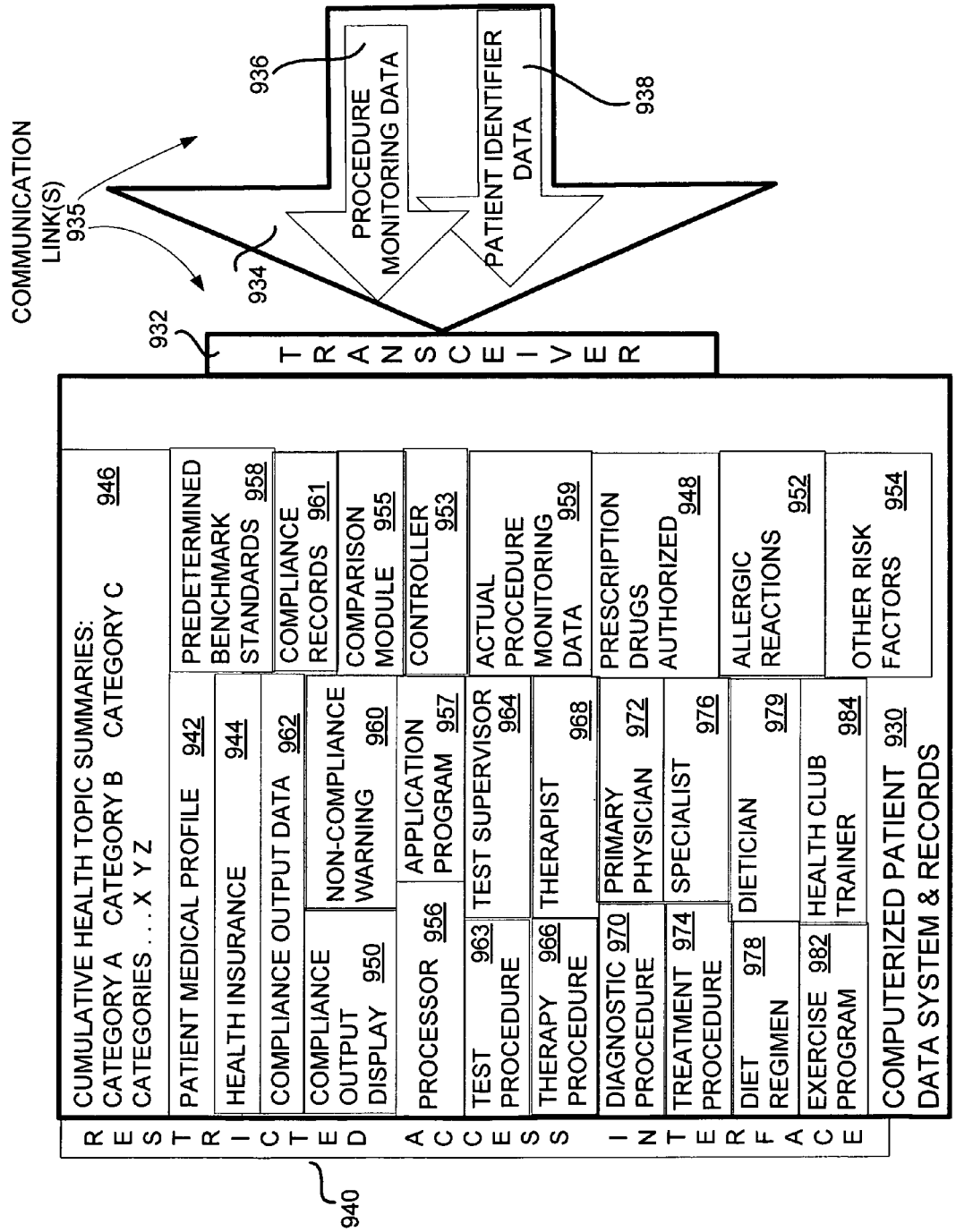
FIG. 33 is a schematic representation of a further embodiment features for a computerized patient data system.

The schematic representation of FIG. 33 depicts an exemplary embodiment for a computerized patient data system & records 930 for a particular patient. A restricted access interface 940 may be included to provide restricted "read" and/or "write" access to an approved person or entity. Updated patient monitoring data may be received via communication link(s) 935 that include transceiver 932 and communication media 934 for transmitting procedure monitoring data 936 and patient identifier data 938.

The exemplary embodiment of FIG. 33 may include various data records including patient medical profile 942, health insurance 944, cumulative health topic summaries for different categories 946. Other possible patient data records may include prescription drugs authorized 948, allergic reactions 952, other patient risk factors 954, and predetermined benchmark standards 958.

Operation components may include controller 953, comparison module 955, processor 956, and application program 957 for collection and processing of actual procedure monitoring data 959 correlated with the particular patient. Additional functional components to facilitate appropriate patient supervision, oversight and feedback may include a non-compliance warning 960, compliance records 961, compliance output data 962 and compliance output display 950 (e.g., see FIG. 35).

Additional exemplary records relating to the cumulative health topic summaries for different categories 946 may include an identification of a health-related procedure and an associated responsible party. Illustrative examples shown in the embodiment of FIG. 33 include test procedure 963 and test supervisor 964, therapy procedure 966 and therapist 968, diagnostic procedure 970 and primary physician 972, treatment procedure 974 and specialist 976, diet regimen 978 and dietician 979, as well as exercise program 982 and health club trainer 984. It will be understood that other health categories and responsible parties may be included, and some health categories and responsible parties may be omitted, depending on the specific needs and circumstances of the particular patient.

Figure 34:
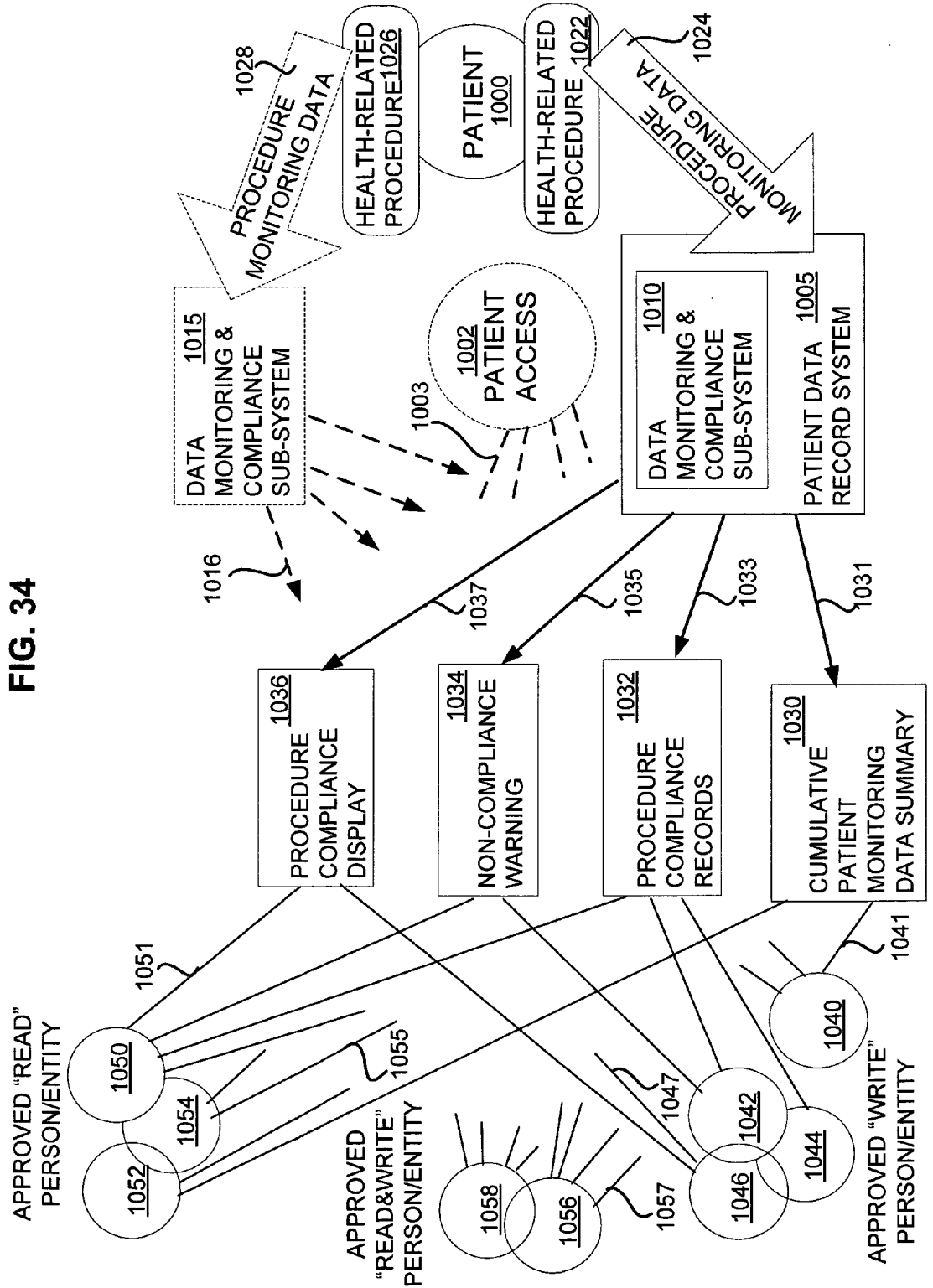
FIG. 34 is a schematic representation showing further exemplary embodiment features that may be implemented.

Additional possible embodiment features are depicted in the schematic representation of FIG. 34 in connection with a patient 1000. For example, a patient data record system 1005 may include a data monitoring & compliance sub-system 1010 for collecting and processing procedure monitoring data 1024 involving a health-related procedure for patient 1000. An exemplary data output 1031 may be utilized to provide a cumulative patient monitoring data summary 1030. Another exemplary data output 1033 may be utilized to provide procedure compliance records 1032. A further exemplary data output 1035 may be utilized to provide a non-compliance warning 1034. An additional exemplary data output 1036 may be utilized to provide a procedure compliance display 1036.

In some instances a separate data monitoring & compliance sub-system 1015 may be respectively provided for collecting and processing procedure monitoring data 1028 involving another health-related procedure 1026 for patient 1000. Various exemplary data outputs 1016 may be generated in suitable formats (e.g., components 1030, 1032, 1034, 1036) for immediate as well as ongoing accessibility to an approved person or entity.

It will be understood that patient access 1002 to the informational data of components 1030, 1032, 1034, 1036 may be available through one or more communication links 1003.

Accessibility to the informational data of components 1030, 1032, 1034, 1036 may be available to an approved person or entity in accordance with applicable privacy and legal guidelines. For example, one or more approved "write" persons/entities 1040, 1042, 1044, 1046 may have the same and/or different specified access privileges 1041, 1047. As a further example, one or more approved "read" persons/entities 1050, 1052, 1054 may have the same and/or different specified access privileges 1051, 1055. As another example, one or more approved "read & write" persons/entities 1056, 1058 may have the same and/or different specified access privileges 1057.

Figure 35:
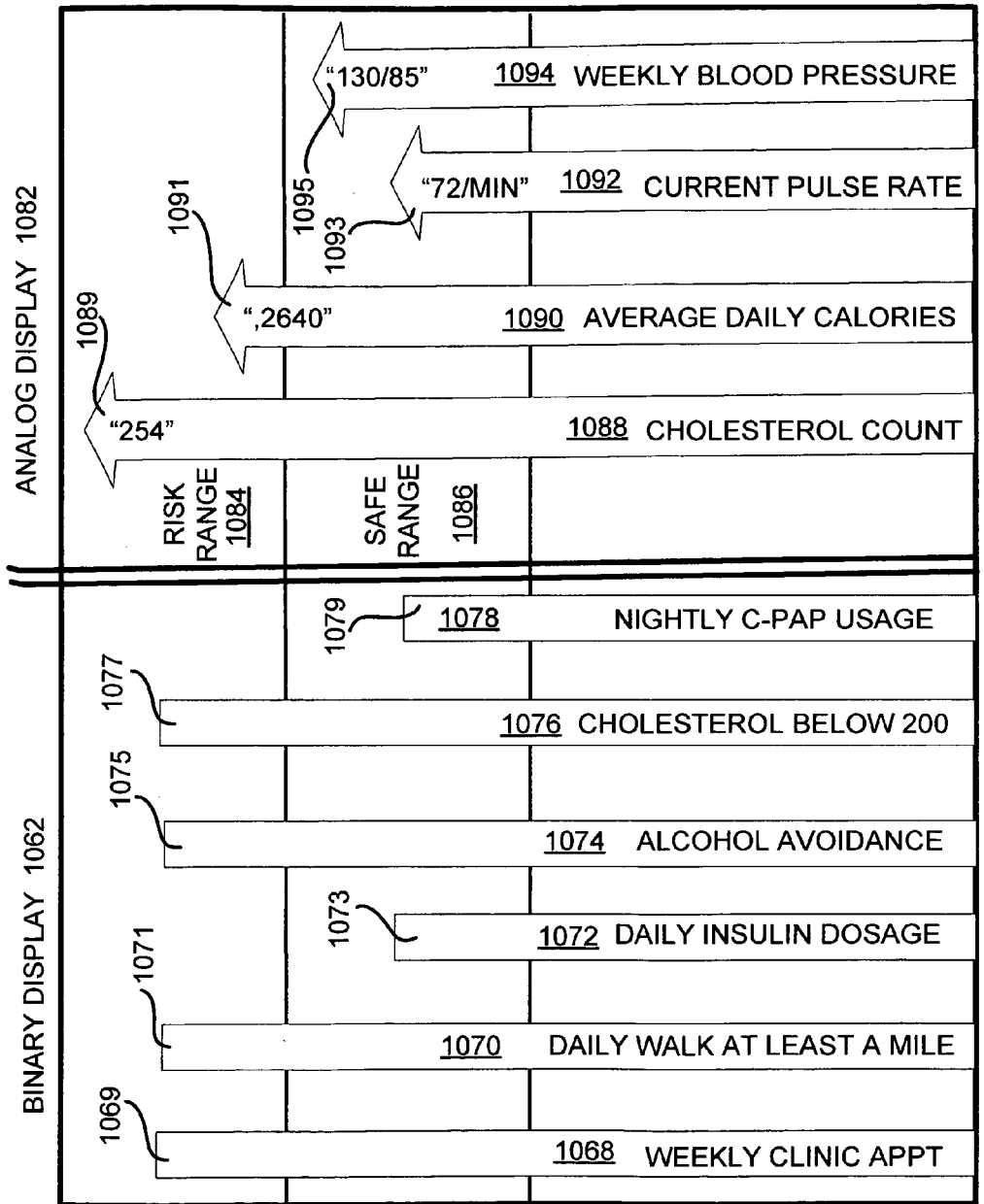
FIG. 35 is a schematic depiction of an exemplary embodiment for a patient compliance output display.

An exemplary embodiment of a patient compliance output display 1060 is illustrated in the schematic representation of FIG. 35. In some implementations a binary display 1062 may be utilized for health-related procedures of a specified health-related category 1065. A representation of patient compliance for one or more health-related procedures may be graphically indicated in a bar graph format under a heading called "satisfactory action" 1066. A representation of patient non-compliance for one or more health-related procedures may be graphically indicated in a bar graph format under another heading called "unsatisfactory action" 1067.

A listing for a weekly clinic appointment 1068 for a required medical checkup is shown on the output display to be satisfactory 1069 based on monitored feedback data. A listing for a daily walk at least a mile 1070 regarding an exercise regimen is shown on the output display to be satisfactory 1071 based on monitored feedback data. In contrast, a listing for daily insulin dosage 1072 in connection with diabetes treatment is shown on the output display to be unsatisfactory 1073 based on monitored feedback data or in some instances an absence of monitored feedback data.

A listing for alcohol avoidance 1074 in connection with alcoholism or a DUI (driving under the influence) probation is shown on the output display to be satisfactory 1075 based on monitored feedback data. A listing for "cholesterol below 200" for hypertension is shown on the output display to be satisfactory 1077 based on monitored feedback data. In contrast, a listing for nightly C-PAP (continuous positive airway pressure) usage 1078 regarding sleep apnea treatment is shown on the output display to be unsatisfactory 1079 based on monitored feedback data or in some instances an absence of monitored feedback data.

As further illustrated in FIG. 35, an exemplary implementation of a patient compliance output display 1060 may include an analog display 1082 for health-related procedures of a specified health-related category 1065. A representation of patient compliance as well as a quantitative monitored data value for one or more health-related procedures may be graphically indicated in a bar graph format under a heading called "safe range" 1086. A representation of patient non-compliance as well as a quantitative monitored data value for one or more health-related procedures may be graphically indicated in a bar graph format under another heading called "risk range" 1084.

A listing for a cholesterol count 1088 for a recent or periodic blood test is shown on the output display to be at risk 1089 based on an updated empirical cholesterol reading of "254". A listing for average daily calories 1090 for obesity prevention or treatment is shown on the output display to be at risk 1091 based on an updated empirical calorie calculation showing "1640 calories per day". In contrast, a listing for current pulse rate 1092 of a recovering heart attack patient is shown on the output display to be considered as safe based on an updated empirical value of "72 beats per minute". As a further contrast, a listing for weekly blood pressure 1094 for a hypertension patient under medication is shown on the output display to be considered as possibly safe but in a pre-hypertension range approaching a danger threshold based on an updated empirical reading of "systolic/diastolic 130 over 85".

It will be understood from the graphical representation of FIG. 35 that a quantitative value for an analog quantitative graphical indication may be displayed numerically and/or visually (length of bar, color highlight, etc.) in order to provide as much readable/recognizable trends, danger indicators, etc. depending on the seriousness and urgency of the patient's condition and/or the health parameter being monitored.

It will be understood that the various exemplary system embodiment features disclosed herein may be implemented in a patient data system that includes a patient data record associated with a designated patient, and a data input link coupled to the patient data record and configured to receive updated information based on real-time monitoring data regarding administration of a selected health-related procedure to the designated patient. Further possible system implementation features may include computerized apparatus configured to process a patient identifier for correlation with the selected health-related procedure, and a comparison module operably coupled to the patient data record and the computer apparatus, wherein the comparison module is configured to determine compliance of the real-time monitoring data with a predetermined benchmark standard.

Some system embodiments may also include a patient data record having one or more data entries indicating verification of a health-related procedure scheduled or completed for the designated patient. Other possible patient data records may include one or more data entries indicating verification of one of more of the following types of health-related procedure scheduled or completed by the recipient patient: diagnosis, test, treatment, malady, ailment, surgical procedure, anesthetic, medication, diet, therapy, and nutritional regimen.

Other system embodiments may provide a patient data record that includes patient compliance records accessible via one or more of the following techniques: hardcopy view, hardcopy printout, display monitor, remote access, text access, audio access, image access, fax access, hyperlinked access, and cross-reference link.

Additional possible system features may provide an application program having instructions encoded on computer-readable media for executing a process for confirmation of the patient identifier. Other possible system implementations may provide an application program having instructions encoded on computer-readable media for executing a process for verification of completion of the health-related procedure for the designated patient.

Figure 36:
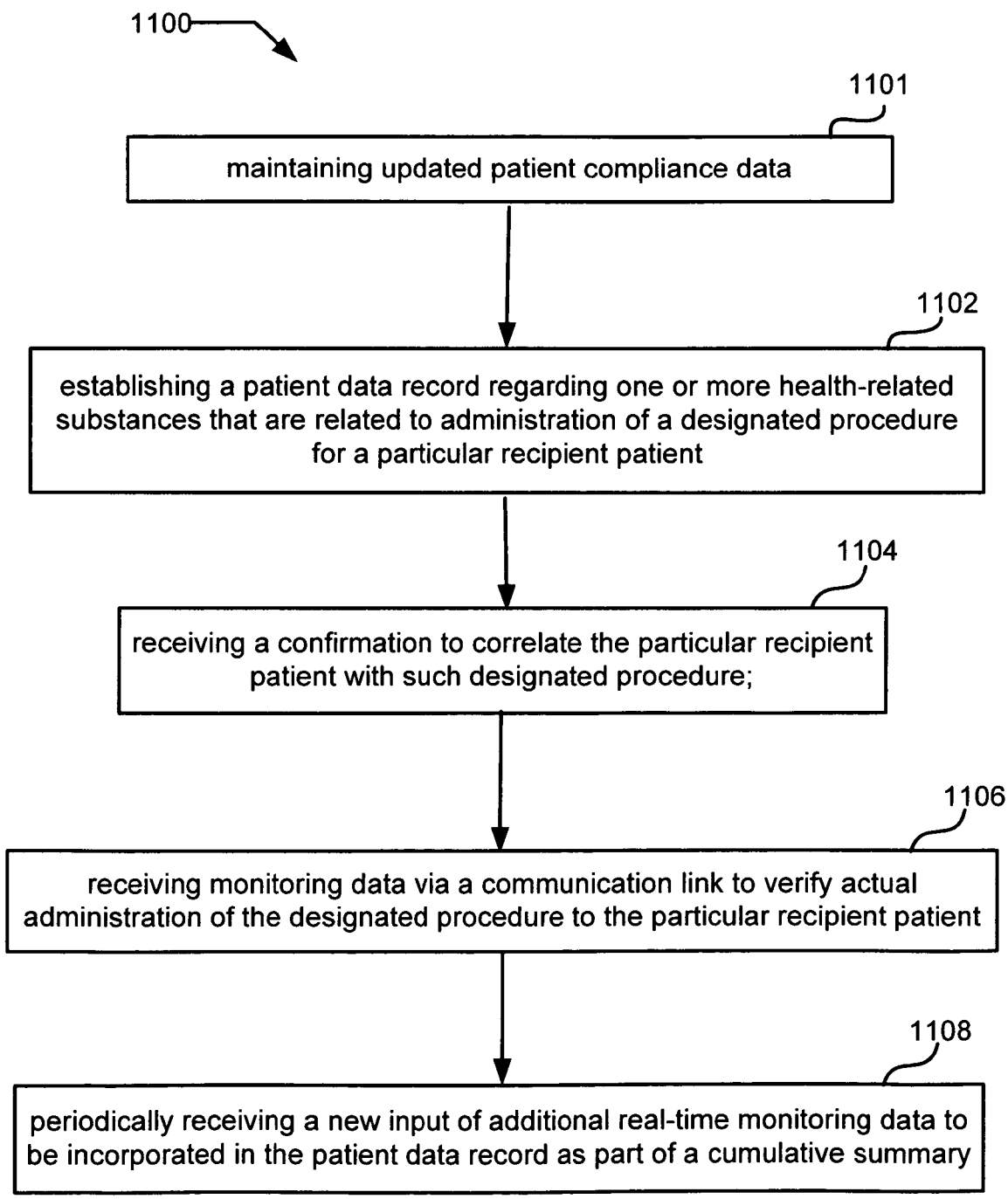
FIG. 36 is a high level flow chart for an exemplary process embodiment.

Referring to the embodiment features 1100 illustrated in FIG. 36, an exemplary process implementation may include maintaining updated patient compliance data (block 1101), establishing a patient data record regarding one or more health-related substances that are related to administration of a designated procedure for a particular recipient patient (block 1102), and receiving a confirmation to correlate the particular recipient patient with such designated procedure (block 1104). Additional process components may include receiving monitoring data via a communication link to verify actual administration of the designated procedure to the particular recipient patient (block 1106), and periodically receiving a new input of additional real-time monitoring data to be incorporated in the patient data record as part of a cumulative summary (block 1108).

Figure 37:
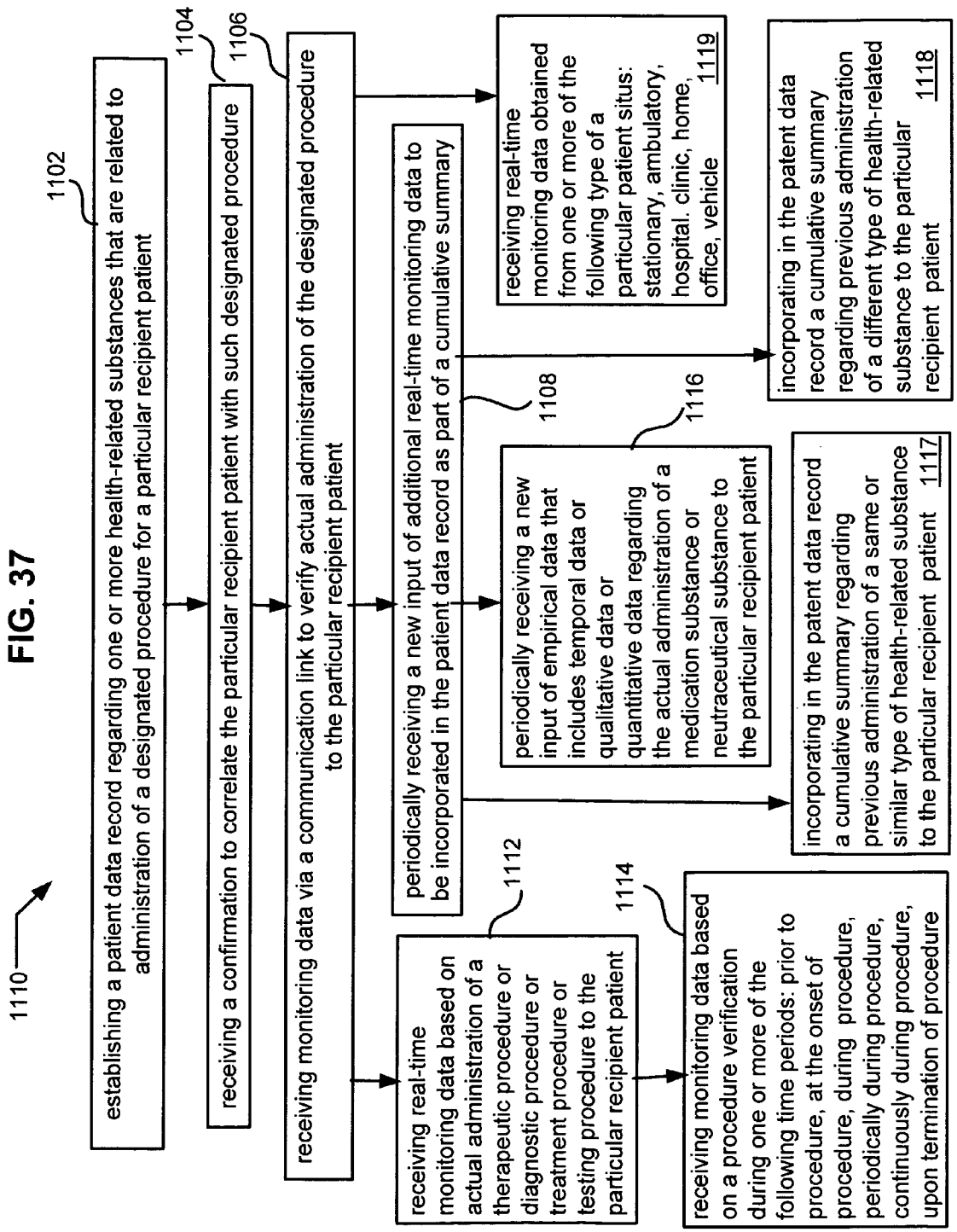

Additional possible embodiments 1110 are depicted in the flow chart of FIG. 37, wherein previously described process components 1102, 1104, 1106, 1108 may be implemented in combination with receiving real-time monitoring data based on actual administration of a therapeutic procedure or diagnostic procedure or treatment procedure or testing procedure to the particular recipient patient (block 1112). Further possible aspects may include receiving monitoring data based on a procedure verification during one or more of the following time periods: prior to procedure, at the onset of procedure, during procedure, periodically during procedure, continuously during procedure, upon termination of procedure (block 1114).

In some instances an embodiment may further include periodically receiving a new input of empirical data that includes temporal data or qualitative data or quantitative data regarding the actual administration of a medication substance or neutraceutical substance to the particular recipient patient (block 1116). Other exemplary aspects may include incorporating in the patent data record a cumulative summary regarding previous administration of a same or similar type of health-related substance to the particular recipient patient (block 1117). Another possible implementation may include incorporating in the patent data record a cumulative summary regarding previous administration of a different type of health-related substance to the particular recipient patient (block 1118).

Another exemplary embodiment may include receiving real-time monitoring data obtained from one or more of the following type of a particular patient situs: stationary, ambulatory, hospital, clinic, home, office, vehicle (block 1119).

Figure 38:
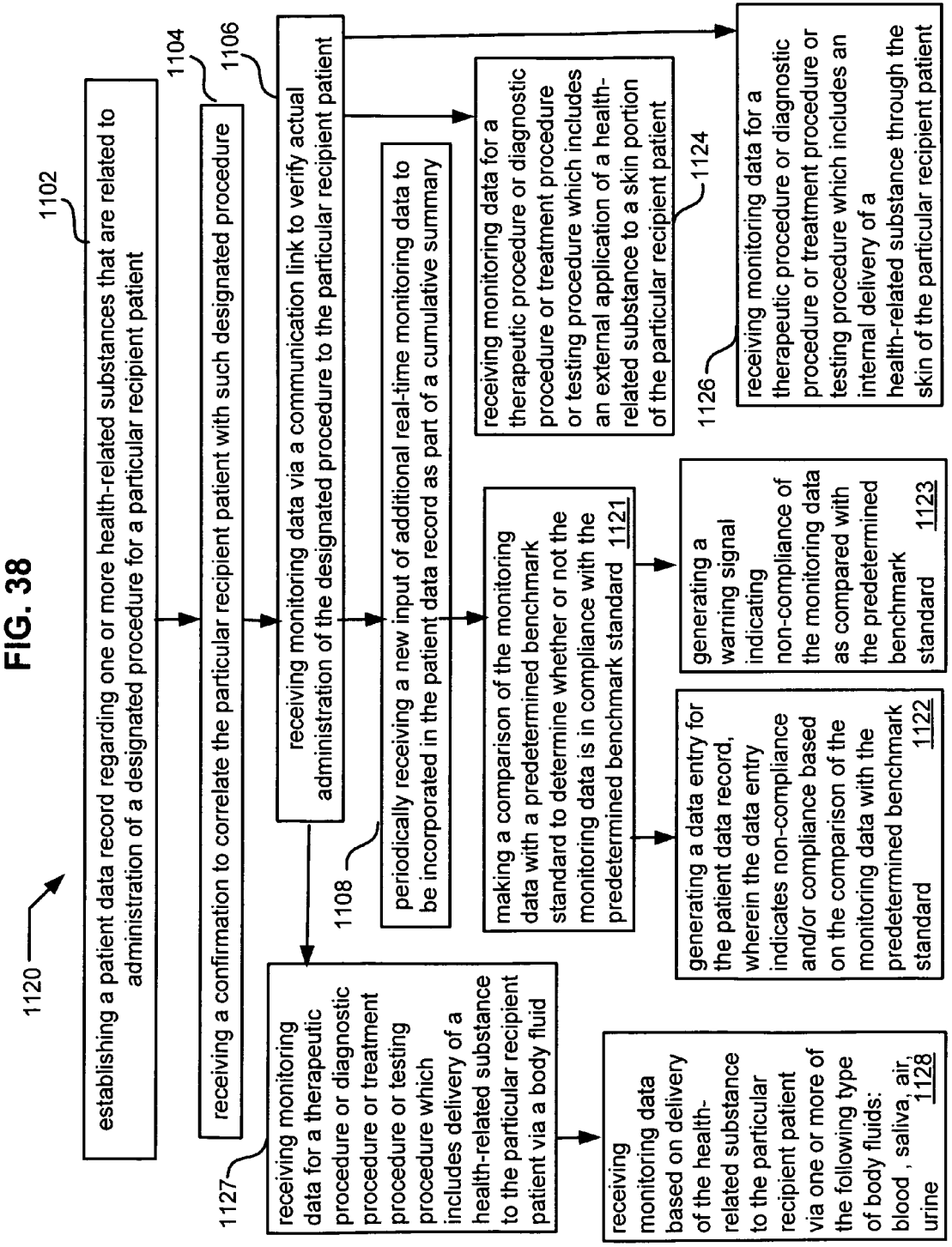

The detailed flow chart of FIG. 38 illustrates further process embodiment features 1120 that include previously described operations 1102, 1104, 1106, 1108 along with making a comparison of the monitoring data with a predetermined benchmark standard to determine whether or not the monitoring data is in compliance with the predetermined benchmark standard (block 1121). Additional related aspects may include generating a data entry for the patient data record, wherein the data entry indicates non-compliance and/or compliance based on the comparison of the monitoring data with the predetermined benchmark standard (block 1122), and may further include generating a warning signal indicating non-compliance of the monitoring data as compared with the predetermined benchmark standard (block 1123).

In some circumstances, an exemplary embodiment may include receiving monitoring data for a therapeutic procedure or diagnostic procedure or treatment procedure or testing procedure which includes an external application of a health-related substance to a skin portion of the particular recipient patient (block 1124). Another process aspect may include receiving monitoring data for a therapeutic procedure or diagnostic procedure or treatment procedure or testing procedure which includes an internal delivery of a health-related substance through the skin of the particular recipient patient (block 1126).

Other process possibilities illustrated in FIG. 38 include receiving monitoring data for a therapeutic procedure or diagnostic procedure or treatment procedure or testing procedure which includes delivery of a health-related substance to the particular recipient patient via a body fluid (block 1127). Additional possibilities include receiving monitoring data based on delivery of the health-related substance to the particular recipient patient via one or more of the following type of body fluids: blood, saliva, air, urine (block 1128).

Figure 39:
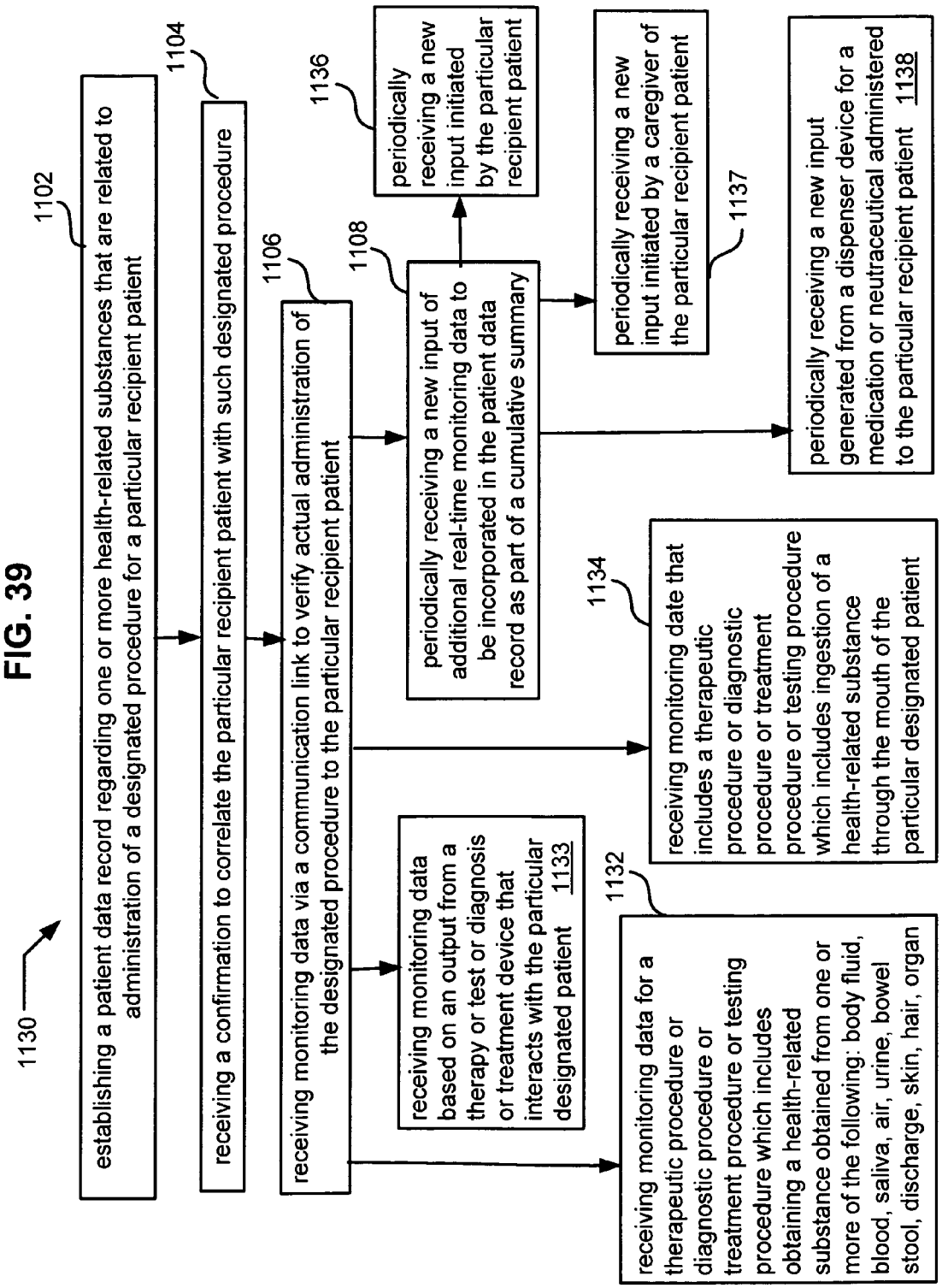

Referring now to the exemplary features 1130 depicted in FIG. 39, the previously described operations 1102, 1104, 1106, 1108 may be implemented in combination with receiving monitoring data for a therapeutic procedure or diagnostic procedure or treatment procedure or testing procedure which includes obtaining a health-related substance obtained from one or more of the following: body fluid, blood, saliva, air, urine, bowel stool, discharge, skin, hair, organ (block 1132). Other implementation features may include receiving monitoring data based on an output from a therapy or test or diagnosis or treatment device that interacts with the particular designated patient (block 1133). Such monitoring data in some instances may include receiving monitoring data for a therapeutic procedure or diagnostic procedure or treatment procedure or testing procedure which includes ingestion of a health-related substance through the mouth of the particular designated patient (block 1134).

Other process components may include periodically receiving a new input initiated by the particular recipient patient (block 1136), as well as periodically receiving a new input initiated by a caregiver of the particular recipient patient (block 1137). Some exemplary implementations may include periodically receiving a new input generated from a dispenser device for a medication or neutraceutical administered to the particular recipient patient (block 1138).

Figure 40:
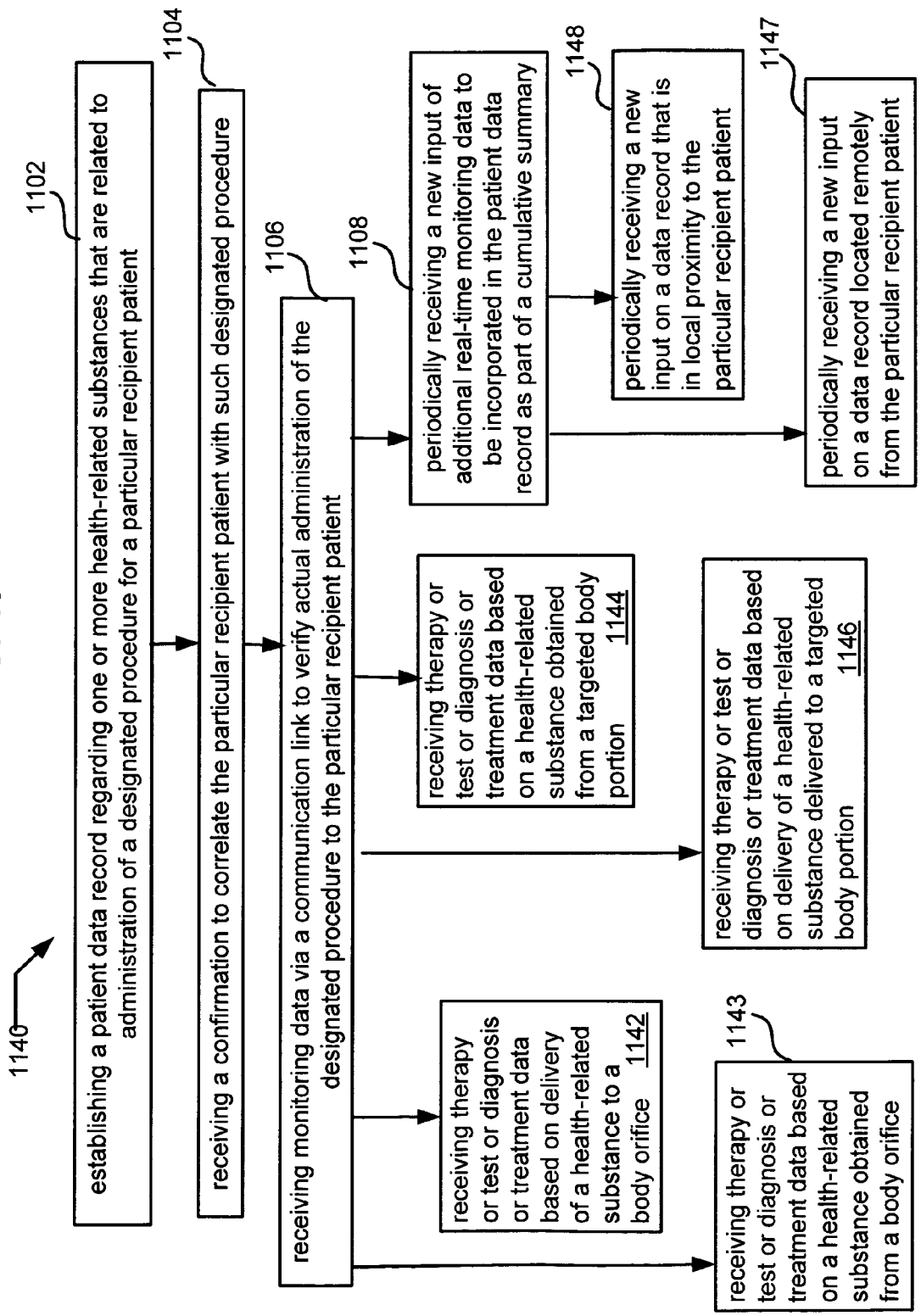

The detailed flow chart of FIG. 40 illustrates further possible embodiment features 1140, including previously described operations 1102, 1104, 1106, 1108 along with receiving therapy or test or diagnosis or treatment data based on delivery of a health-related substance to a body orifice (block 1142). Further possible process features may include receiving therapy or test or diagnosis or treatment data based on a health-related substance obtained from a body orifice (block 1143).

In some instances a process component may include receiving therapy or test or diagnosis or treatment data based on delivery of a health-related substance delivered to a targeted body portion (block 1144). Other possible process components may include receiving therapy or test or diagnosis or treatment data based on a health-related substance obtained from a targeted body portion (block 1146). Some embodiments may include periodically receiving a new input on a data record located remotely from the particular recipient patient (block 1147). Another possible embodiment feature may include periodically receiving a new input on a data record that is in local proximity to the particular recipient patient (block 1148).

Figure 41:
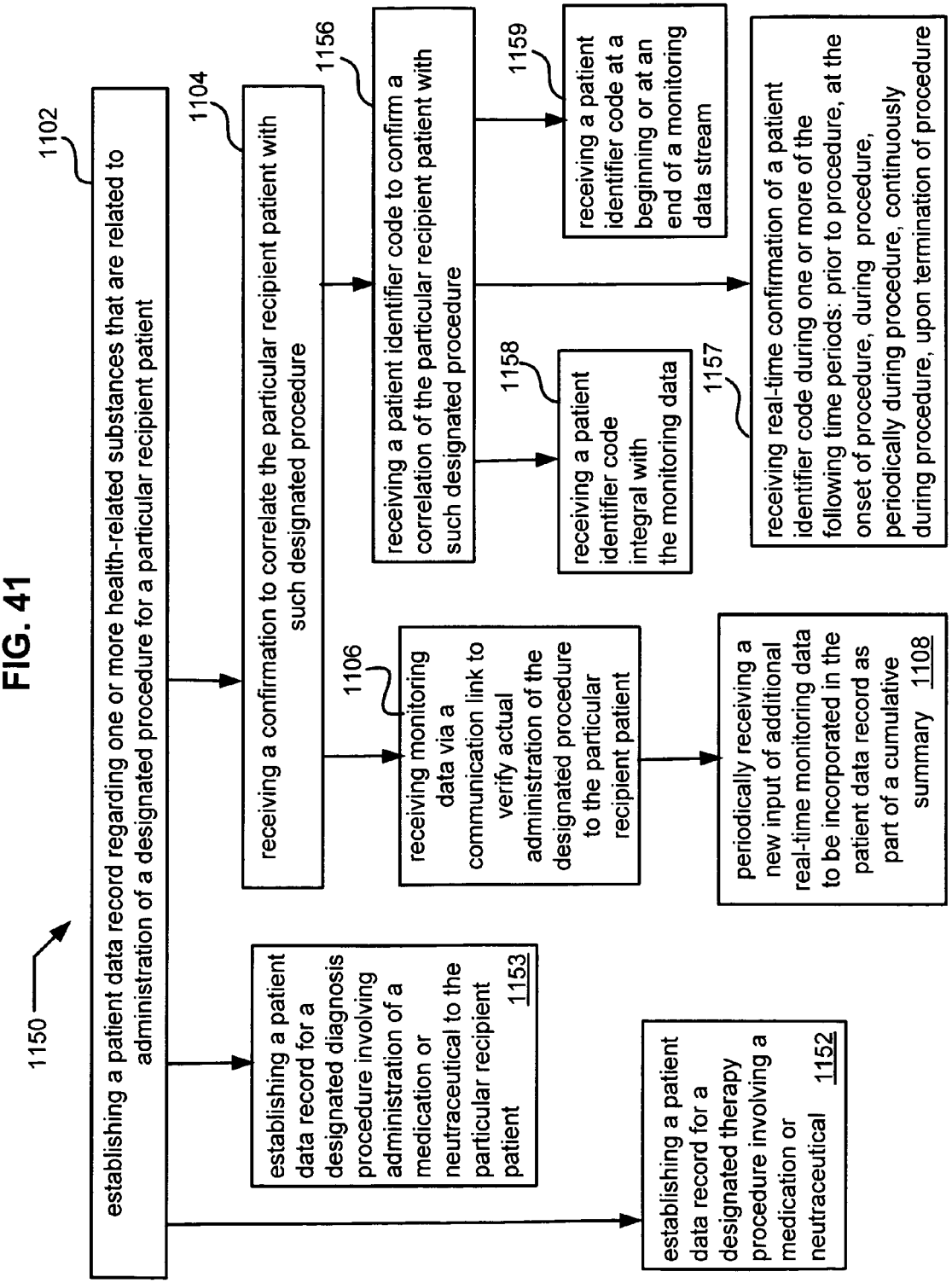

Referring to exemplary features 1150 depicted in the detailed flow chart of FIG. 41, some embodiments may include previously described operations 1102, 1104, 1106, 1108 in combination with establishing a patient data record for a designated health-related procedures involving the medication or neutraceutical. Some possible implementations may include establishing a patient data record for a designated therapy procedure involving the medication or neutraceutical (block 1152). Another possible implementation may include establishing a patient data record for a designated diagnosis procedure involving administration of a medication or neutraceutical to the particular recipient patient (block 1153).

Additional implementation features related to a patient identifier may include receiving a patient identifier code to confirm a correlation of the particular recipient patient with such designated procedure (block 1156), and receiving real-time confirmation of a patient identifier code during one or more of the following time periods: prior to procedure, at the onset of procedure, during procedure, periodically during procedure, continuously during procedure, upon termination of procedure (block 1157).

Other possible process features illustrated in FIG. 41 include receiving a patient identifier code integral with the monitoring data (block 1158), and receiving a patient identifier code at a beginning or at an end of a monitoring data stream (block 1159).

The detailed flow chart of FIG. 42 illustrates further possible process operations 1160 that include previously described process features 1102, 1104, 1106, 1108 as well as periodically receiving a new input of additional monitoring data based on an automatic procedure verification (block 1162). Another possible process operation may include periodically receiving a new input of additional monitoring data based on a user-activated procedure verification (block 1164).

Additional exemplary features depicted include establishing a patient data record for a designated test procedure involving administration of a medication or neutraceutical to the particular recipient (block 1166), and establishing a patient data record for a designated treatment procedure involving administration of a medication or neutraceutical to the particular recipient patient (block 1167). Another possible process feature may include receiving a confirmation from the particular recipient patient or from a caregiver of the particular recipient patient to confirm a correlation of the particular recipient patient with one or more such designated procedures (block 1168).

It will be understood that the specified health-related procedures described herein are by way of example only and are not intended to be limiting, and may be scheduled and administered for many separate as well as combined purposes (e.g., diagnosis, therapy, testing, treatment, prevention, research, causal investigation, and the like). In some circumstances it may be desirable to monitor only one or a few health-related procedures administered to a particular recipient patient; in other circumstances such monitoring may occur only during predetermined time periods or at selected locations; and some patients may nevertheless be subject to simultaneous as well as continuous monitoring of many ongoing health-related procedures.

It will be understood by those skilled in the art that the various components and elements disclosed in the block diagrams herein as well as the various steps and sub-steps disclosed in the flow charts herein may be incorporated together in different claimed combinations in order to enhance possible benefits and advantages.

It is to be further understood that various aspects of the methods and processes disclosed in FIGS. 4-8 and FIGS. 10-14 and FIG. 20 and FIGS. 27-31 and FIGS. 36-42 can be incorporated in one or more different types of computer program products with a carrier medium having program instructions encoded thereon. Some exemplary computer program products may be implemented in storage carrier media having program instructions encoded thereon. In some instances exemplary computer program products may be implemented in communication signal carrier media having program instructions encoded thereon.

Some computer program product embodiments may include computer-readable media bearing instructions for executing a process that includes identifying a recipient patient scheduled for administration of a selected health-related procedure, maintaining a patient data record for such administration of the selected health-related procedure to the recipient patient, and processing and/or storing real-time monitoring data that includes confirmation of a patient identifier for the recipient patient as well as real-time verification of administration of the selected health-related procedure. An additional process feature may include making a comparison regarding a health-related procedure administered to a recipient patient to determine compliance with a predetermined benchmark standard.

Another process feature that may be encoded as instructions on computer-readable media may include maintaining updated patient compliance records accessible via one or more of the following techniques: hardcopy view, hardcopy printout, display monitor, remote access, text access, audio access, image access, fax access, hyperlinked access, and cross-reference link.

The exemplary system, apparatus, and computer program product embodiments disclosed herein including FIGS. 1-3 and FIG. 9 and FIGS. 15-19 and FIGS. 21-26 and FIGS. 32-35 along with other components, devices, know-how, skill and techniques that are known in the art have the capability of implementing and practicing the methods and processes shown in FIGS. 4-8 and FIGS. 10-14 and FIG. 20 and FIGS. 27-31 and FIGS. 36-42. However it is to be further understood by those skilled in the art that other systems, apparatus and technology may be used to implement and practice such methods and processes. Those skilled in the art will also recognize that the various aspects of the embodiments for methods, processes, products, and systems as described herein can be implemented individually and/or collectively by a wide range of hardware, software, firmware, or any combination thereof.

Exemplary embodiments disclosed herein provide a verification technique that facilitates administration of a health-related procedure to an intended recipient patient or group of patients. An interface template or signal protocol may be configured to establish suitable matching between the patient and various types of objects used to administer the health-related procedure. In some embodiments real-time monitoring data regarding administration of a health-related procedure to a recipient patient is posted to a patient data record that has restricted read/write access. In some instances the monitoring data is processed to determine compliance or non-compliance based on comparison of the health-related procedure with a predetermined benchmark standard.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A system comprising:
   circuitry configured for receiving monitoring data of at least one health-related parameter and at least one patient identifier determined from at least one patient interface template having identifying surface indicia;
   circuitry configured for associating the monitoring data of the at least one health-related parameter with the at least one patient identifier; and
   circuitry configured for communicating the monitoring data of the at least one health-related parameter for incorporation with at least one patient data record associated with the at least one patient identifier.

2. The system of claim 1, wherein the circuitry configured for receiving monitoring data of at least one health-related parameter and at least one patient identifier determined from at least one patient interface template having identifying surface indicia comprises:
   circuitry configured for receiving monitoring data substantiating administration of at least one health-related procedure and at least one patient identifier determined from at least one patient interface template having identifying surface indicia.

3. The system of claim 1, wherein the circuitry configured for receiving monitoring data of at least one health-related parameter and at least one patient identifier determined from at least one patient interface template having identifying surface indicia comprises:
   circuitry configured for receiving monitoring data of at least one health-related parameter comparable with at least one benchmark standard and receiving at least one patient identifier determined from at least one patient interface template having identifying surface indicia.

4. The system of claim 1, wherein the circuitry configured for receiving monitoring data of at least one health-related parameter and at least one patient identifier determined from at least one patient interface template having identifying surface indicia comprises:
   circuitry configured for receiving monitoring data of at least one health-related parameter associated with one or more substances and at least one patient identifier determined from at least one patient interface template having identifying surface indicia.

5. The system of claim 1, wherein the circuitry configured for receiving monitoring data of at least one health-related parameter and at least one patient identifier determined from at least one patient interface template having identifying surface indicia comprises:
   circuitry configured for receiving monitoring data of at least one health-related parameter associated with one or more treatments and at least one patient identifier determined from at least one patient interface template having identifying surface indicia.

6. The system of claim 1, wherein the circuitry configured for receiving monitoring data of at least one health-related parameter and at least one patient identifier determined from at least one patient interface template having identifying surface indicia comprises:
   circuitry configured for receiving monitoring data of at least one health-related parameter associated with one or more tests and at least one patient identifier determined from at least one patient interface template having identifying surface indicia.

7. The system of claim 1, wherein the circuitry configured for receiving monitoring data of at least one health-related parameter and at least one patient identifier determined from at least one patient interface template having identifying surface indicia comprises:
   circuitry configured for receiving monitoring data of at least one health-related parameter associated with one or more physical activities and at least one patient identifier determined from at least one patient interface template having identifying surface indicia.

8. The system of claim 1, wherein the circuitry configured for receiving monitoring data of at least one health-related parameter and at least one patient identifier determined from at least one patient interface template having identifying surface indicia comprises:
   circuitry configured for receiving monitoring data of at least one health-related parameter associated with one or more bodily samples and at least one patient identifier determined from at least one patient interface template having identifying surface indicia.

9. The system of claim 1, wherein the circuitry configured for receiving monitoring data of at least one health-related parameter and at least one patient identifier determined from at least one patient interface template having identifying surface indicia comprises:
   circuitry configured for receiving monitoring data of at least one health-related parameter generated from one or more sensors and at least one patient identifier determined from at least one patient interface template having identifying surface indicia.

10. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter generated from at least one health-related device and at least one patient identifier determined from at least one patient interface template having identifying surface indicia.

11. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter generated from one or more exercise devices and at least one patient identifier determined from at least one patient interface template having identifying surface indicia.

12. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter generated from one or more body associated devices and at least one patient identifier determined from at least one patient interface template having identifying surface indicia.

13. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter generated from one or more vehicles and at least one patient identifier determined from at least one patient interface template having identifying surface indicia.

14. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter generated from one or more dispensers and at least one patient identifier determined from at least one patient interface template having identifying surface indicia.

15. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter and at least one patient identifier determined from at least one ambulatory patient interface template having identifying surface indicia.

16. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter and at least one patient identifier determined from physical engagement with at least one patient interface template having identifying surface indicia.

17. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter and at least one patient identifier determined from complementary engagement with at least one patient interface template having identifying surface indicia.

18. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter and at least one patient identifier determined from engagement of at least one patient interface template having identifying surface indicia with at least one other device.

19. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter and at least one patient identifier determined from at least one signal protocol associated with at least one patient interface template having identifying surface indicia.

20. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter and at least one patient identifier determined from at least one patient interface template having one or more geometric shapes.

21. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter and at least one patient identifier determined from at least one patient interface template having identifying surface indicia formed from one or more physical protrusions and/or recesses.

22. The system of claim 1, wherein the circuitry configured for receiving monitoring data of at least one health-related parameter and at least one patient identifier determined from at least one patient interface template having identifying surface indicia comprises:
circuitry configured for receiving real-time monitoring data of at least one health-related parameter and at least one patient identifier determined from at least one patient interface template having identifying surface indicia.

23. The system of claim 1, wherein the circuitry configured for receiving monitoring data of at least one health-related parameter and at least one patient identifier determined from at least one patient interface template having identifying surface indicia comprises:
circuitry configured for receiving qualitative monitoring data of at least one health-related parameter and at least one patient identifier determined from at least one patient interface template having identifying surface indicia.

24. The system of claim 1, wherein the circuitry configured for receiving monitoring data of at least one health-related parameter and at least one patient identifier determined from at least one patient interface template having identifying surface indicia comprises:
circuitry configured for receiving at least one determined location and at least one patient identifier determined from at least one patient interface template having identifying surface indicia.

25. The system of claim 1, wherein the circuitry configured for receiving monitoring data of at least one health-related parameter and at least one patient identifier determined from at least one patient interface template having identifying surface indicia comprises:
circuitry configured for receiving monitoring data of at least one health-related parameter along with at least one patient identifier determined from at least one patient interface template having identifying surface indicia.

26. The system of claim 1, wherein the circuitry configured for receiving monitoring data of at least one health-related parameter and at least one patient identifier determined from at least one patient interface template having identifying surface indicia comprises:
circuitry configured for receiving upon user indication monitoring data of at least one health-related parameter and at least one patient identifier determined from at least one patient interface template having identifying surface indicia.

27. The system of claim 1, wherein the circuitry configured for communicating the monitoring data of the at least one health-related parameter for incorporation with at least one patient data record associated with the at least one patient identifier comprises:
circuitry configured for incorporating the monitoring data of the at least one health-related parameter in at least one patient data record associated with the at least one patient identifier.

28. The system of claim 1, wherein the circuitry configured for communicating the monitoring data of the at least one health-related parameter for incorporation with at least one patient data record associated with the at least one patient identifier comprises:
circuitry configured for communicating the monitoring data of the at least one health-related parameter for incorporation with at least one patient data record associated with the at least one patient identifier and communicating at least one warning.

29. The system of claim 1, further comprising:
circuitry configured for enabling at least one health-related device based at least in part on the at least one patient identifier.

30. The system of claim 1, further comprising:
circuitry configured for enabling at least one health-related procedure based at least in part on the at least one patient identifier.

31. The system of claim 1, further comprising:
circuitry configured for at least partially enabling access to the at least one patient data record based at least in part on the at least one patient identifier.

32. A system comprising:
means for receiving monitoring data of at least one health-related parameter and at least one patient identifier determined from at least one patient interface template having identifying surface indicia;
means for associating the monitoring data of the at least one health-related parameter with the at least one patient identifier; and
means for communicating the monitoring data of the at least one health-related parameter for incorporation with at least one patient data record associated with the at least one patient identifier.

33. A method at least partially implemented using one or more processing components comprising:
receiving monitoring data of at least one health-related parameter and at least one patient identifier determined from at least one patient interface template having identifying surface indicia;
associating the monitoring data of the at least one health-related parameter with the at least one patient identifier; and
communicating the monitoring data of the at least one health-related parameter for incorporation with at least one patient data record associated with the at least one patient identifier.

34. A system comprising
at least one signal bearing medium having one or more instructions for facilitating operations comprising:
receiving monitoring data of at least one health-related parameter and at least one patient identifier determined from at least one patient interface template having identifying surface indicia;
associating the monitoring data of the at least one health-related parameter with the at least one patient identifier; and
communicating the monitoring data of the at least one health-related parameter for incorporation with at least one patient data record associated with the at least one patient identifier.

35. One or more non-transitory computer readable media bearing one or more instructions for facilitating operations comprising:
receiving monitoring data of at least one health-related parameter and at least one patient identifier determined from at least one patient interface template having identifying surface indicia;
associating the monitoring data of the at least one health-related parameter with the at least one patient identifier; and
communicating the monitoring data of the at least one health-related parameter for incorporation with at least one patient data record associated with the at least one patient identifier.

* * * * *